US006538108B1

(12) United States Patent
Liskay et al.

(10) Patent No.: US 6,538,108 B1
(45) Date of Patent: Mar. 25, 2003

(54) COMPOSITIONS AND METHODS RELATING TO DNA MISMATCH REPAIR GENES

(75) Inventors: Robert M. Liskay, Lake Oswego, OR (US); C. Eric Bronner, Portland, OR (US); Sean M. Baker, Berkeley, CA (US); Roni J. Bollag, Martinez, GA (US); Richard D. Kolodner, San Diego, CA (US)

(73) Assignees: Dana-Farber Cancer Institute, Boston, MA (US); Oregon Health Sciences University, Portland, OR (US)

( * ) Notice: Subject to any disclaimer, the term of this patent is extended or adjusted under 35 U.S.C. 154(b) by 0 days.

(21) Appl. No.: 09/265,503

(22) Filed: Mar. 10, 1999

Related U.S. Application Data

(63) Continuation of application No. 08/352,902, filed on Dec. 4, 1994, now Pat. No. 6,191,268, which is a continuation-in-part of application No. 08/209,521, filed on Mar. 8, 1994, now Pat. No. 5,922,855, which is a continuation-in-part of application No. 08/168,877, filed on Dec. 17, 1993, now abandoned.

(51) Int. Cl.$^7$ ........................ C07K 16/00; C07K 16/18; C07K 16/32

(52) U.S. Cl. ............................... 530/387.1; 530/388.1; 530/388.2; 530/389.1; 530/389.7; 530/391.3

(58) Field of Search ........................... 530/387.1, 389.1, 530/388.1, 388.2, 389.7, 391.3

(56) References Cited

U.S. PATENT DOCUMENTS

| 4,683,195 A | 7/1987 | Mullis et al. |
| 5,043,272 A | 8/1991 | Hartley |
| 5,750,335 A * | 5/1998 | Gifford |

FOREIGN PATENT DOCUMENTS

| WO | WO95/15381 | 6/1995 |
| WO | WO95/20678 | 8/1995 |

OTHER PUBLICATIONS

Accession No. A33589, Feb. 1990.*
Marsha S. Williamson et al., "Meiotic Gene Conversion Mutants in *Saccharomyces cerevisiae* I. Isolation and Characterization of PMS1–1 and PMS1–2," *Genetics*, Aug., 1985, pp. 609–646.
Gene Levinson et al., "High Frequencies of Short Frameshifts in Poly–CA/TG Tandem Repeats Borne by Bacteriophage M13 in *Escherichia coli* K–12," *Nucleic Acids Research*, Jun. 2, 1987, pp. 5323–5337.
S. L. Naylor et al., "Loss of Heterozygosity of Chromosome 3p Markers in Small–Cell Lung Cancer," *Nature*, Oct. 1, 1987, pp. 451–454.

Klaas Kok et al., "Deletion of a DNA Sequence at the Chromosomal Region 3p21 in all Major Types of Lung Cancer," *Nature*, Dec. 10, 1987, pp. 578–581.
Douglas K. Bishop et al., "Specificity of Mismatch Repair Following Transformation of *Saccharomyces cerevisiae* with Heteroduplex Plasmid DNA," *Proc. Natl. Acad. Sci. USA*, May 1989, pp. 3713–3717.
Stanley Fields et al., "A Novel Genetic System to Detect Protein–Protein Interactions," *Nature*, Jul. 20, 1989, pp. 245–246.
Barbara Kramer et al., "Heteroduplex DNA Correction in *Saccharomyces cerevisiae* Is Mismatch Specific and Requires Functional PMS Genes," *Molecular and Cellular Biology*, Oct. 1989, pp. 4432–4440.
John A. Mankovich et al., "Nucleotide Sequence of the *Salmonella typhimurium* mutL Gene Required for Mismatch Repair: Homology of MutL to HexB of *Streptococcus pneumoniae* and to PMS1 of the Yeast *Saccharomyces cerevisiae*," *Journal of Bacteriology*, Oct. 1989, pp. 5325–5331.
Marc Prudhomme et al., "Nucleotide Sequence of the *Streptococcus pneumoniae* hexB Mismatch Repair Gene: Homology of HexB to MutL of *Salmonella typhimurium* and to PMS1 of *Saccharomyces cerevisiae*," *Journal of Bacteriology*, Oct. 1989, pp. 5332–5338.
Wilfried Kramer et al., "Cloning and Nucleotide Sequence of DNA Mismatch Repair Gene PMS1 from *Saccharomyces cerevisiae*: Homology of PMS1 to Procaryotic MutL and HexB," *Journal of Bacteriology*, Oct. 1989, pp. 5339–5346.
Iqbal Unnisa Ali et al., "Presence of Two Members of c–erbA Receptor Gene Family (c–erbAβ and c–erbA2) in Smallest Region of Somatic Homozygosity on Chromosome 3p21–p25 in Human Breast Carcinoma," *Journal of the National Cancer Institute*, Dec. 6, 1989, pp. 1815–1820.
Peter Lichter et al., "High–Resolution Mapping of Human Chromosome 11 by in Situ Hybridization with Cosmid Clones," *Science*, Jan. 5, 1990, pp. 64–69.
Rhona Borts et al., "Mismatch Repair–Induced Meiotic Recombination Requires the PMS1 Gene Product," *Genetics*, Mar. 1990, 124:573–584.
Paul Modrich, "Mechanisms and Biological Effects of Mismatch Repair," *Annu. Rev. Genet.*, 1991, pp. 229–253.

(List continued on next page.)

Primary Examiner—Anthony C. Caputa
Assistant Examiner—Karen A. Canella
(74) *Attorney, Agent, or Firm*—Kolisch Hartwell, P.C.

(57) ABSTRACT

Genomic sequences of human mismatch repair genes and gene products are described, as are methods of detecting mutations and/or polymorphisms in those genes. Also described are methods of diagnosing cancer susceptibility in a subject, and methods of identifying and classifying mismatch-repair-defective tumors. In particular, sequences and methods relating to human mutL homologs, hMLH1 and hPMS1 genes and gene products are provided.

6 Claims, 25 Drawing Sheets

OTHER PUBLICATIONS

Stephen J. Elledge et al., "λYes: A Multifunctional cDNA Expression Vector for the Isolation of Genes by Complementation of Yeast and *Escherichia coli* Mutations," *Proc. Natl. Acad. Sci. USA*, Mar. 1991, pp. 1731–1735.

Ann L. Boyle et al., "Rapid Physical Mapping of Cloned DNA on Banded Mouse Chromosomes by Fluorescence in Situ Hybridization," *Genomics*, Aug. 19, 1991, pp. 106–115.

Farida Latif et al., "Chromosome 3p Deletions in Head and Neck Carcinomas: Statistical Ascertainment of Allelic Loss[1]," Jan. 8, 1992, pp. 1451–1456.

Robert A. G. Reenan et al., "Isolation and Characterization of Two *Saccharomyces cerevisiae* Genes Encoding Homologs of the Bacterial HexA and MutS Mismatch Repair Proteins," *Genetics*, Dec. 1992, pp. 963–973.

Robert A. G. Reenan et al., "Characterization of Insertion Mutations in the *Saccharomyces cerevisiae* MSH1 and MSH2 Genes: Evidence for Separate Mitochondrial and Nuclear Functions," *Genetics*, Dec. 1992, pp. 975–985.

M. F. Lyon et al., "Mouse Chromosome Atlas," Jan. 20, 1993.

Henry T. Lynch et al., "Genetics, Natural History, Tumor Spectrum, and Pathology of Hereditary Nonpolyposis Colorectal Cancer: An Updated Review," *Gastroenterology*, May 1993, pp. 1535–1549.

Jean Marx, "New Colon Cancer Gene Discovered," *Science*, May 7, 1993, pp. 751–752.

Päivi Peltomäki et al., "Genetic Mapping of a Locus Predisposing to Human Colorectal Cancer," *Science*, May 7, 1993, pp. 810–812.

Lauri A. Aaltonen et al., "Clues to the Pathogenesis of Familial Colorectal Cancer," *Science*, May 7, 1993, pp. 812–816.

S. N. Thibodeau et al., "Microsatellite Instability in Cancer of the Proximal Colon," *Science*, May 7, 1993, pp. 816–819.

Yurij Ioniv et al., "Ubiquitous Somatic Mutations in Simple Repeated Sequences Reveal a New Mechanism for Colonic Carcinogenesis," *Nature*, Jun. 10, 1993, pp. 558–561.

Thomas A. Kunkel, "Slippery DNA and Diseases," *Nature*, Sep. 16, 1993, pp. 207–208.

Micheline Strand et al., "Destabilization of Tracts of Simple Repetitive DNA in Yeast by Mutations Affecting DNA Mismatch Repair," *Nature*, Sep. 16, 1993, pp. 274–276.

Hye–Jung Han et al., "Genetic Instability in Pancreatic Cancer and Poorly Differentiated Type of Gastric Cancer," *Cancer Research*, Nov. 1, 1993, pp. 5087–5089.

John I. Risinger et al., "Genetic Instability of Microsatellites in Endometrial Carcinoma," *Cancer Research*, Nov. 1, 1993, pp. 5100–5103.

Annika Lindblom et al., "Genetic Mapping of a Second Locus Predisposing to Hereditary Non–Polyposis Colon Cancer," *Nature Genetics*, Nov. 1993, pp. 279–282.

Richard Fishel et al., "The Human Mutator Gene Homolog MSH2 and Its Association with Hereditary Nonpolyposis Colon Cancer," *Cell*, Dec. 3, 1993, pp. 1027–1038.

Fredrick S. Leach et al., "Mutations of a mutS Homolog in Hereditary Nonpolyposis Colorectal Cancer," *Cell*, Dec. 17, 1993, pp. 1215–1225.

Ramon Parsons et al., "Hypermutability and Mismatch Repair Deficiency in RER+ Tumor Cells," *Cell*, Dec. 17, 1993, pp. 1227–1236.

Steven M. Powell et al., "Molecular Diagnosis of Familial Adenomatous Polyposis," *The New England Journal of Medicine*, Dec. 30, 1993, pp. 1982–1987.

Rebecca Kolbero, "Linking DNA Mismatch Repair to Carcinogenesis," *The Journal of NIH Research*, Dec. 1993, vol. 5, pp. 22–24.

Tomas A. Prolla et al., "Dual Requirement in Yeast DNA Mismatch Repair for MLH1 and PMS1, Two Homologs of the Bacterial mutL Gene," *Molecular and Cellular Biology*, Jan. 1994, pp. 407–415.

C. Eric Bronner et al., "Mutation in the DNA Mismatch Repair Gene Homologue hMLH1 is Associated with Hereditary Non–Polyposis Colon Cancer," *Nature*, Mar. 17, 1994, pp. 258–261.

Nickolas Papadopoulos et al., "Mutation of a mutL Homolog in Hereditary Colon Cancer," *Science*, Mar. 18, 1994, vol. 263, pp. 1625–1629.

Sean Baker et al., "Male Mice Defective in the DNA Mismatch Repair Gene PMS2 Exhibit Abnormal Chromosome Synapsis in Meiosis," *Cell*, Jul. 28, 1995, vol. 82, No. 2, pp. 309–319.

Sean Baker et al., "Involvement of Mouse Mlh1 in DNA Mismatch Repair and Meiotic Crossing Over," *Nature Genetics*, Jul. 13, 1996, pp. 336–342.

\* cited by examiner

```
                                              1         10        20
MutL                                          MPIQVLPPQLANQIAAGEVVERPASVVK  - SEQ ID NO:1
                                              *  **  ************ ******  *
HexB                                          MSHIIELPEMLANQIAAGEVIERPASVCK - SEQ ID NO:2
                                                              *    *  ****
Pms1   MFHHIENLLIETEKRCKQKEQRYIPVKYLFSHTQIHQINDIDVHRITSGQVITDLTTAVK - SEQ ID NO:3
       1         10        20        30        40        50       60

40        50        60        70        80
MutL   ELVENSLDAGATRVDIDIERGGAKLIRIRDNGCGIKKEELALALARHATSKIASLDDLEA
       *****  ***   *  **  *   *  *** **    *** *********      **
HexB   ELVENAIDAGSSQIIIEIEEAGLKKVQITDNGHGIAHDEVELALRRHATSKIKNQADLFR
       *** *  ***    *   *         **   *         * ****    *
Pms1   ELVDNSIDANANQIEIIFKDYGLESIECSDNGDGIDPSHYEFLALKHYTSKIAKFQDVAK
              70        80        90       100       110       120

100       110       120       130       140
MutL   IISLGFRGEALASISSVSRLTLTSRTAEQAEAWQAYAEGRDMDVTVKPAAHPVGTTLEVL
       *  ********  ** *** ***                **    * **  ****    *
HexB   IRTLGFRGEALPSIASVSVLTLLTAVDGASHGTKLVARGGEVE.EVIPATSPVGTKVCVE
       **********   *   *     *                         **  **  *
Pms1   VQTLGFRGEALSSLCGIAKLSVITTTSPPKADKELYDMVGHIT.SKTTTSRNKGTTVLVS
              130       140       150       160       170

160       170       180       190       200
MutL   DLFYNTPARRK.FMRTEKTEFNHIDEIIRRIALARFDVTLNLSHNGKLVRQYRAVAKDGQ
       ***  *****  *       *   *  *  **      *         **        **
HexB   DLFFNTPARLK.YMKSQQAELSHIIDIVNRLGLAHPEISFSLISDGKEMTR...TAGTGQ
                                                     **  *
Pms1   QLFHNLPVRQKEFSKTFKRQFTKCLTVIQGYAIINAAIKFSVWNITPKGKKNLILSTMRN
              190       200       210       220       230

220       230       240       250       260
MutL   KERRLGAICGTPFLEQALAIEWQHGDLTLRGWVADPNHTTTALTEIQYCYVNGRMMRDRL
        * *       **              **   *   *    *   *       ***   *
HexB   LRQAIAGIYGLVSAKKMIEIENSDLDFEISGFVSLPELTRANRNYISL.FINGRYIKNFL
         *  *  *    **        *    *                         *
Pms1   SSMRKN.ISSVFGAGGMRGELEVDLVLDLNPFXNRMLGKYTDDPDFLDLDYKIRVKGYIS
              250       260        270       280       290

280                                       290       300
MutL   INHAIRQACEDKLGA........................DQQPAFVLYLEIDPMHQVDV
        * **                                      *   * ***   **
HexB   LHRAILDGFCSKLMV........................GRFPLAVIHIHIDPYLADV
        *                                          **         * **
Pms1   QNSFGCGRNSKDRQFIYVNKRPVEYSTLLKCCNEVYKTFNNVQFPAVFLNLELPMSLIDV
              310       320       330       340       350

310       320       330       340       350       360
MutL   NVHPAKHEVRFHQSRLVHDFIYQGVLSVLQQQTETALPLEEIAPAPRHVQENRIAAGRNH
       ****  *  ***                  *  **   ***           *
HexB   NVHPTKQEVRISKEKELMTLVSEAIANSLKEQTLIPDALENLAKSTVRNREKVEQTILPL
       ** *  *                *                                *
Pms1   NVTPDKRVILLHNERAVID.IFKTTLSDYYNRQELALPKRMCSQSEQQAQKRLKTEVFDD
              370        380       390       400       410

450       460       470       480       490       500
HexB   SFPELEFFGQMHGTYLFA....QGRDGLYIIDQHAAQERVKYEEYRESIGNVDQSQQQLL
         *   **                *  ****   *    *                **
Pms1   DFKKMEVVGQFNLGFIIVTRKVDNKSDLFIVDQHASDEKYNFETLQAVTVF...KSQKLI
              710       720       730       740       750

510       520       530       540       550       560
HexB   VPYIFEFPADDALRLKERMPLLEEVGVFLAEYGENQFILREHPIWMAEEEIESGIYEMCD
         *     *    * *       *      **    *  *   *      *
Pms1   IPQPVELSVIDELVVLDNLPVFEKNGFKLKIDEEEEFGSRVKLLSLPTSKQTLFDLGDFN
              760       770       780       790       800       810

570       580       590       600       610
HexB   MLLLTKEVSIKKYRAELA........IMMSCKRSIKANHRIDDHSARQLLYQLSQCDNPY
         *            *          *   **  *               ** *
Pms1   ELIHLIKEDGGLRRDNIRCSKIRSMFAMRACRSSIMIGKPLNKKTMTRVVVHNLSELDKPW
              820       830       840       850       860       870

620
HexB   NCPHGRPVLVHFT
       *******  *
Pms1   NCPHGRPTMRHLM
              880       890
```

Figure 2

Human MLH1 cDNA Nucleotide Sequence

```
CTTGGCTCTTCTGGCGCCAAAATGTCGTTCGTGGCAGGGGTTATTCGGCGGCTGGACGAG    60  - SEQ ID NO:4
                 M   S   F   V   A   G   V   I   R   R   L   D   E       - SEQ ID NO:5
ACAGTGGTGAACCGCATCGCGGCGGGGGAAGTTATCCAGCGGCCAGCTAATGCTATCAAA   120
  T   V   V   N   R   I   A   A   G   E   V   I   Q   R   P   A   N   A   I   K
GAGATGATTGAGAACTGTTTAGATGCAAAATCCACAAGTATTCAAGTGATTGTTAAAGAG   180
  E   M   I   E   N   C   L   D   A   K   S   T   S   I   Q   V   I   V   K   E
GGAGGCCTGAAGTTGATTCAGATCCAAGACAATGGCACCGGGATCAGGAAAGAAGATCTG   240
  G   G   L   K   L   I   Q   I   Q   D   N   G   T   G   I   R   K   E   D   L
GATATTGTATGTGAAAGGTTCACTACTAGTAAACTGCAGTCCTTTGAGGATTTAGCCAGT   300
  D   I   V   C   E   R   F   T   T   S   K   L   Q   S   F   E   D   L   A   S
ATTTCTACCTATGGCTTTCGAGGTGAGGCTTTGGCCAGCATAAGCCATGTGGCTCATGTT   360
  I   S   T   Y   G   F   R   G   E   A   L   A   S   I   S   H   V   A   H   V
ACTATTACAACGAAAACAGCTGATGGAAAGTGTGCATACAGAGCAAGTTACTCAGATGGA   420
  T   I   T   T   K   T   A   D   G   K   C   A   Y   R   A   S   Y   S   D   G
AAACTGAAAGCCCCTCCTAAACCATGTGCTGGCAATCAAGGGACCCAGATCACGGTGGAG   480
  K   L   K   A   P   P   K   P   C   A   G   N   Q   G   T   Q   I   T   V   E
GACCTTTTTTACAACATAGCCACGAGGAGAAAAGCTTTAAAAAATCCAAGTGAAGAATAT   540
  D   L   F   Y   N   I   A   T   R   R   K   A   L   K   N   P   S   E   E   Y
GGGAAAATTTTGGAAGTTGTTGGCAGGTATTCAGTACACAATGCAGGCATTAGTTTCTCA   600
  G   K   I   L   E   V   V   G   R   Y   S   V   H   N   A   G   I   S   F   S
GTTAAAAAACAAGGAGAGACAGTAGCTGATGTTAGGACACTACCCAATGCCTCAACCGTG   660
  V   K   K   Q   G   E   T   V   A   D   V   R   T   L   P   N   A   S   T   V
GACAATATTCGCTCCATCTTTGGAAATGCTGTTAGTCGAGAACTGATAGAAATTGGATGT   720
  D   N   I   R   S   I   F   G   N   A   V   S   R   E   L   I   E   I   G   C
GAGGATAAAACCCTAGCCTTCAAAATGAATGGTTACATATCCAATGCAAACTACTCAGTG   780
  E   D   K   T   L   A   F   K   M   N   G   Y   I   S   N   A   N   Y   S   V
AAGAAGTGCATCTTCTTACTCTTCATCAACCATCGTCTGGTAGAATCAACTTCCTTGAGA   840
  K   K   C   I   F   L   L   F   I   N   H   R   L   V   E   S   T   S   L   R
AAAGCCATAGAAACAGTGTATGCAGCCTATTTGCCCAAAAACACACACCCATTCCTGTAC   900
  K   A   I   E   T   V   Y   A   A   Y   L   P   K   N   T   H   P   F   L   Y
CTCAGTTTAGAAATCAGTCCCCAGAATGTGGATGTTAATGTGCACCCCACAAAGCATGAA   960
  L   S   L   E   I   S   P   Q   N   V   D   V   N   V   H   P   T   K   H   E
GTTCACTTCCTGCACGAGGAGAGCATCCTGGAGCGGGTGCAGCAGCACATCGAGAGCAAG  1020
  V   H   F   L   H   E   E   S   I   L   E   R   V   Q   Q   H   I   E   S   K
CTCCTGGGCTCCAATTCCTCCAGGATGTACTTCACCCAGACTTTGCTACCAGGACTTGCT  1080
  L   L   G   S   N   S   S   R   M   Y   F   T   Q   T   L   L   P   G   L   A
GGCCCCTCTGGGGAGATGGTTAAATCCACAACAAGTCTGACCTCGTCTTCTACTTCTGGA  1140
  G   P   S   G   E   M   V   K   S   T   T   S   L   T   S   S   S   T   S   G
AGTAGTGATAAGGTCTATGCCCACCAGATGGTTCGTACAGATTCCCGGGAACAGAAGCTT  1200
  S   S   D   K   V   Y   A   H   Q   M   V   R   T   D   S   R   E   Q   K   L
GATGCATTTCTGCAGCCTCTGAGCAAACCCCTGTCCAGTCAGCCCCAGGCCATTGTCACA  1260
  D   A   F   L   Q   P   L   S   K   P   L   S   S   Q   P   Q   A   I   V   T
```

Figure 3

Human MLH1 cDNA Nucleotide Sequence (cont'd)

```
GAGGATAAGACAGATATTTCTAGTGGCAGGGCTAGGCAGCAAGATGAGGAGATGCTTGAA      1320
E  D  K  T  D  I  S  S  G  R  A  R  Q  Q  D  E  E  M  L  E
CTCCCAGCCCCTGCTGAAGTGGCTGCCAAAAATCAGAGCTTGGAGGGGGATACAACAAAG      1380
L  P  A  P  A  E  V  A  A  K  N  Q  S  L  E  G  D  T  T  K
GGGACTTCAGAAATGTCAGAGAAGAGAGGACCTACTTCCAGCAACCCCAGAAAGAGACAT      1440
G  T  S  E  M  S  E  K  R  G  P  T  S  S  N  P  R  K  R  H
CGGGAAGATTCTGATGTGGAAATGGTGGAAGATGATTCCCGAAAGGAAATGACTGCAGCT      1500
R  E  D  S  D  V  E  M  V  E  D  D  S  R  K  E  M  T  A  A
TGTACCCCCCGGAGAAGGATCATTAACCTCACTAGTGTTTTGAGTCTCCAGGAAGAAATT      1560
C  T  P  R  R  R  I  I  N  L  T  S  V  L  S  L  Q  E  E  I
AATGAGCAGGGACATGAGGTTCTCCGGGAGATGTTGCATAACCACTCCTTCGTGGGCTGT      1620
N  E  Q  G  H  E  V  L  R  E  M  L  H  N  H  S  F  V  G  C
GTGAATCCTCAGTGGGCCTTGGCACAGCATCAAACCAAGTTATACCTTCTCAACACCACC      1680
V  N  P  Q  W  A  L  A  Q  H  Q  T  K  L  Y  L  L  N  T  T
AAGCTTAGTGAAGAACTGTTCTACCAGATACTCATTTATGATTTTGCCAATTTTGGTGTT      1740
K  L  S  E  E  L  F  Y  Q  I  L  I  Y  D  F  A  N  F  G  V
CTCAGGTTATCGGAGCCAGCACCGCTCTTTGACCTTGCCATGCTTGCCTTAGATAGTCCA      1800
L  R  L  S  E  P  A  P  L  F  D  L  A  M  L  A  L  D  S  P
GAGAGTGGCTGGACAGAGGAAGATGGTCCCAAAGAAGGACTTGCTGAATACATTGTTGAG      1860
E  S  G  W  T  E  E  D  G  P  K  E  G  L  A  E  Y  I  V  E
TTTCTGAAGAAGAAGGCTGAGATGCTTGCAGACTATTTCTCTTTGGAAATTGATGAGGAA      1920
F  L  K  K  K  A  E  M  L  A  D  Y  F  S  L  E  I  D  E  E
GGGAACCTGATTGGATTACCCCTTCTGATTGACAACTATGTGCCCCCTTTGGAGGGACTG      1980
G  N  L  I  G  L  P  L  L  I  D  N  Y  V  P  P  L  E  G  L
CCTATCTTCATTCTTCGACTAGCCACTGAGGTGAATTGGGACGAAGAAAAGGAATGTTTT      2040
P  I  F  I  L  R  L  A  T  E  V  N  W  D  E  E  K  E  C  F
GAAAGCCTCAGTAAAGAATGCGCTATGTTCTATTCCATCCGGAAGCAGTACATATCTGAG      2100
E  S  L  S  K  E  C  A  M  F  Y  S  I  R  K  Q  Y  I  S  E
GAGTCGACCCTCTCAGGCCAGCAGAGTGAAGTGCCTGGCTCCATTCCAAACTCCTGGAAG      2160
E  S  T  L  S  G  Q  Q  S  E  V  P  G  S  I  P  N  S  W  K
TGGACTGTGGAACACATTGTCTATAAAGCCTTGCGCTCACACATTCTGCCTCCTAAACAT      2220
W  T  V  E  H  I  V  Y  K  A  L  R  S  H  I  L  P  P  K  H
TTCACAGAAGATGGAAATATCCTGCAGCTTGCTAACCTGCCTGATCTATACAAAGTCTTT      2280
F  T  E  D  G  N  I  L  Q  L  A  N  L  P  D  L  Y  K  V  F
GAGAGGTGTTAAATATGGTTATTTATGCACTGTGGGATGTGTTCTTCTTTCTCTGTATTC      2340
E  R  C
CGATACAAAGTGTTGTATCAAAGTGTGATATACAAAGTGTACCAACATAAGTGTTGGTAG      2400
CACTTAAGACTTATACTTGCCTTCTGATAGTATTCCTTTATACACAGTGGATTGATTATA      2460
AATAAATAGATGTGTCTTAACATA                                          2484
```

TGGCTGGATGCTAAGCTACAGCTGAAGGAAGAACGTGAGCACGaggcactgaggt
gattggcTGAAGGCACTTCCGTTGAGCATCTAGACGTTTCcttggctcttctggc
gccaaaatgtcgttcgtggcagggg ttattcggcggctggacgagacagtggtga
accgcatcgcggcgggggaagtta tccagcggccagctaatgctatcaaagagat
gattgagaactgGTACGGAGGGAG TCGAGCCGGgctcacttaagggctacgaCTT
AACGGGCCGCGTCACTCAATGGCG CGGACACGCCTCTTTCCCGGGCAGAGGCAT
GTACAGCGCATGCCCACAACGGCG GAGGCCGCCGGGTTCCCTACGTGCCATAAGC
CTTCTCCTTTTC

SEQ. ID NO: 25

SEQ. ID NO: 6

2: 19689 to 19688    (117 to 207)

AAACACGTTAATGAGGCACTATTGTTTGTATTTGGAGTTTGTTATCATTGCTTGG
CTCATATTAAaatatgtacattagagtagttgCAGACTGATAAATTATTTTCTGT
TGATTTGCCAGtttagatgcaaaatccacaagtattcaagtgattgttaaagag
ggaggcctgaagttgattcagatc aagacaatggcaccgggatcagggGTAAGTA
AAACCTCAAAGTAGCAGGATGTT TGTGCGCTTCATGGAAgagtcaggacctttct
ctgTTCTGGAAACTAGGCTTTTGC AGATGGATTTTTTCACTGAAAAATTCAACA
CCAACAATAAATATTTATTGAGTA CCTATTATTTGCGGGGCACTGTTCAGGGGAT
GTGTCAGT

SEQ. ID NO: 26

SEQ. ID NO: 7

3: 19687 to 19786    (208 to 306)

TTTCCTGGATTAATCAAGAAATGGAATTCAAagagatttggaaaatgagtaacAT
GATTATTTACTCATCTTTTGGTATCTAACAGaaagaagatctggatattgtatg
tgaaaggttcactactagtaaact gcagtcctttgaggatttagccagtatttct
acctatggctttcgaggtgagGTA AGCTAAAGATTCAAGAAATGTGTAAAATATc
ctcctgtgatgacattgtCTGTCA TTTGTTAGTATGTATTTCTAACATAGATAA
ATAAGGTTTGGTACCTTTTACTTG TTAAATGTATGCAAATCTGAGCAAACTTAAT
GAACTTTAACTTTCAAAGACTG

SEQ. ID NO: 27

SEQ. ID NO: 8

4  18492 to 18421    (307 to 380)

TGGAAGCAGCAGNCAGATaacctttcccttggtgaggTGACAGTGGGTGACCCA
GCAGTGAGTTTTTCTTTCAGTCTATTTTCTTTTCTTCCTTAGgctttggccagca
taagccatgtggctcatgttacta ttacaacgaaaacagctgatggaaagtgtgc
atacagGTATAGTGCTGACTTCTT TTACTCATATATATTCATTCTGAAATGTATT
TTGGgcctaggtctcagagtaatc CTGTCTCAACACCAGTGTTATCTTTNNNGGC
AGAGATCTTGAGTACG

SEQ. ID NO: 28

SEQ. ID NO: 9

```
TTGATATgattttctcttttcccctttgggATTAGTATCTATCTCTCTACTGGATA
TTAATTTGTTATATTTTCTCATTAGagcaagttactcagatggaaaactgaaagc
ccctcctaaaccatgtgctggcaatcaagggacccagatcacgGTAAGAATGGTA
CATGGGAGAgtaaattgttgaagctttgtttgTATAAATATTGGAATAAAAAATA
AAATTGCTTCTAAGTTTTCAGGGTAATAATAAAATGAATTTGCACTAGTTAATGG
AGGTCCCAAGATATCCTCTAAGCAAGATAAATGACTATTGGCTTTTNNTGGCATG
GCAGCCTG
```
SEQ. ID NO: 10

SEQ. ID NO: 29

6: 18318 to 18317   (454 to 545)

```
GCTTTTGCCAGGACCATCTTgggtttatttcaagtacttctatgAATTTACAA
GAAAAATCAATCTTCTGTTCAGtggaggaccttttttacaacatagccacgagg
agaaaagctttaaaaaatccaagtgaagaatatgggaaaattttggaagttgttg
gcaggTACAGTCCAAAATCTGGGAGTGGGTCTCTGAGATTTGTCATCAAAGTAAT
GTGTTCTAGTgctcatacattgaacagttgctgagcTAGATGGTGAAAAGTAAAA
```
SEQ. ID NO: 11

SEQ. ID NO: 30

7: 19009 to 19135   (546 TO 588)

```
CAGCAACCTATAAAAGTAGAGAGGAGTCTGTGTTTTGACGCAGCACCTTTAGCAT
TTTTATTTGGATGAAGTTTCTGCTGGTTTATTTTTCTGTGGGTAAAATATTAATA
GGCTGTATGGAGATATTTTTCTTTATATGTACCTTTGTTTAGATTACTCAACTCC
ACTAATTTATTTAACTAAAAGGGGGCTCTGACATctagtgtgtgtttttggcAAC
TCTTTTCTTACTCTTTTGTTTTTCTTTTCCAGgtattcagtacacaatgcaggca
ttagtttctcagttaaaaaaGTAAGTTCTTGGTTTATGGGGATGGTTTTGTTTT
ATGAAAAGAAAAAGGGGATTTTTAATAGTTTGCTggtggagataaggttatgAT
GTTT
```
SEQ. ID NO: 12

SEQ. ID NO: 31

8: 18197 to 18924   (589 TO 677)

```
ATGTTTCAGTctcagccatgagacaataaatccTTGTGTCTTCTGCTGTTTGTTT
ATCAGcaaggagagacagtagctgatgttaggacactacccaatgcctcaaccgt
ggacaatattcgctccatctttggaaatgctgttagtcggTATGTCGATAACCTA
TATAAAAAATCTTTTACATTTATTATCTTGGTTTATCATTccatcacattattt
gggaaccTTTCAAGATATTATGTGTGTTAAGAGTTTGCTTTAGTCAAATACACAG
GCTTGTTTTATGCTTCAGATTTGTTAATGGAGTTCTTATTTCACGTAATCAACAC
TTTCTAGGTGTATGTAATCTCCTAGATTCTGTGGCGTGAATCATGTGTTCT
```
SEQ. ID NO: 13

SEQ. ID NO: 32

ACTGAGTAGGGTAGGTGGGTGAGTGGGTGGGTGGGTGGGTGGGTGGATGGATGGA
TGGGAGGATGGGTGGGTGAATGGGTGAACAGACAAATGGATGGATGAATGGACAG
GCACAGGAGGACCTCAAATGGACCAAGTCTTCGGGGCCCTCATTTCACAAAGTTA
GTTTATGGGAAGGAACCTTGTGTTTTTAAATTCTGATTCTTTTGTAATGTTTGAG
TTTTGAGTATTTTcaaaagcttcagaatctcTTTTCTAATAGagaactgatagaa
attggatgtgaggataaaaccctagccttcaaaatgaatggttacatatccaatg
caaactactcagtgaagaagtgcatcttcttactcttcatcaaccGTAAGTTAAA
AAGAACCACATGGAAATccactcacaggaaacacccacagGGAATTTTATGGGA
CCATGGAAAAATTTCTGAGTCCATAGGTTTGATTAAACATGGAGAAACCTCATGG
CAAAGTTTGGTTTTATTGGGAAGCATGTATA                              ⎤ SEQ. ID
                                                              ⎥ NO: 14

SEQ. ID NO: 33

10: 18305 to 18306   (791 TO 884)

ATAGTGGGCTGGAAAGTGGCCACAGGTAAAGGTGCACCTTTCTTCCTGGGGATGT
GATGTGCATATCACTACAGAAATGTCTTTCCTGAGGTGATGTcatgactttgtgt
gaatgtacaccTGTGACCTCACCCCTCAGGACAGTTTTGAACTGGTTGCTTTCTT
TTTATTGTTTAGatcgtctggtagaatcaactccttgagaaaagccatagaaac
agtgtatgcagcctatttgcccaaaacacacaccattcctgtacctcagGTAA      ⎤ SEQ. ID
TGTAGCACCAAACTCCTCAACCAAGACTCACAAGGAAcagatgttctatcaggct    ⎥ NO: 15
ctcctcTTTGAAAGAGATGAGCATGCTAATAGTACAATCAGAGTGAATCCCATAC
ACCACTGGCAAAAGGATGTTCTGTCCCTTCTTACAGGTACAAGGCACAG

SEQ. ID NO: 34

11: 18182 to 19041   (885 TO 1038)

CTTACGCAAAGCTACACAGCTCTTAAGTAGCAGTGCCAATATTTGAACACACTCA
GACTCGAGCCTGAGGTTTTGACCACTGTGTCATCTGGCCTCAAATCTTCTGGCCA
CCACATACACCATATGTgggcttttctcccccctcccACTATCTAAGGTAATTGT
TCTCTCTTATTTTCCTGACAGtttagaaatcagtcccagaatgtggatgttaat      ⎤ SEQ. ID
gtgcacccacaaagcatgaagttcacttcctgcacgaggagagcatcctggagc      ⎥ NO: 16
gggtgcagcagcacatcgagagcagctcctgggctccaattcctccaggatgta
cttcacccagGTCAGGGCGCTTCTCATCCAGCTACTTCTCTGGGGCCTTTGAAAT
GTGCCCGGCCAGAcgtgagagcccagattTTGCTGTTATTTAGGAACTTTTTTT
GAAGTATTACCTGGATAG

SEQ. ID NO: 35

```
GATaattatacctcatactagcTTCTTTCTTAGTACTGCTCCATTTGGGGACCTG
TATATCTATACTTCTTATTCTGAGTCTCTCCACTATATATATATATATATATA
TTTTTTTTTTTTTTTTTTTTAATACAGactttgctaccaggacttgctggcccc
tctggggagatggttaaatccacaacaagtctgacctcgtcttctacttctggaa
gtagtgataaggtctatgcccaccagatggttcgtacagattcccgggaacagaa
gcttgatgcatttctgcagcctctgagcaaaccccgtccagtcagccccaggcc
attgtcacagaggataagacagatatttctagtggcagggctaggcagcaagatg
aggagatgcttgaactcccagcccctgctgaagtggctgccaaaaatcagagctt
ggaggggatacaacaaaggggacttcagaaatgtcagagaagaggacctact
tccagcaaccccagGTATGGCCTTTTGGGAAAAGTACAGCCTAcctcctttattc
tgtaataaaacTGCCTTCTAACTTTGGCTTTTCATGAATCACTTGCATCTTCTCT
CTGCCGACTTCCC
```
] SEQ. ID NO: 17

SEQ. ID NO: 36

The splice acceptor site is believed to have 21 T's.

13: 18420* to 18443  (1410 TO 1558)

```
CTGTGCTCCAGCACAGGTCATCCAGCTCTGTAGACCAGCGCAGAGAAGTTGCTTG
CTCCCAAAtgcaacccacaaaatttggcTAAGTTTAAAAACAAGAATAATAATGA
TCTGCACTTCCTTTTCTTCATTGCAGaaagagagacatcgggaagattctgatgtgg
aaatggtggaagatgattcccgaaaggaaatgactgcagcttgtaccccccggag
aaggatcattaacctcactagtgttttgagtctccaggaagaaattaatgagcag
ggacatgaggGTACGTAAACGCTGTGGCCTGCCTGGGATGCATAGGGCCTCAACT
GCCAAggttttggaaatggagaaagCAGTCATGTTGTCAGAGTGGCACTACAGTT
TTGATGGGCAAGCTCCTCTTCCTTTACTAACCCACAATAGCATCAGCTTAAAGAC
AATTTTTGATTGGGAGAAAAGGGAGAAAATAATCTCTG
```
] SEQ. ID NO: 18

SEQ. ID NO: 37

14: 19028 TO 18897  (1559 TO 1667)

```
CAGTTTTCACCAGGAGGCTCAAATCAGGCNNCTTTGCTTACTtggtgtctctagt
tctggTGCCTGGTGCTTTGGTCAATGAAGTGGGGTTGGTAGGATTCTATTACTTA
CCTGTTTTTTGGTTTTATTTTTTGTTTTGCAGttctccggggagatgttgcataac
cactccttcgtgggctgtgtgaatcctcagtgggccttggcacagcatcaaacca
agttatacttctcaacaccaccagcttagGTAAATCAGCTGAGTGTGTGAACA
AgcagagctactacaacaatgGTCCAGGGAGCACAGGCACAAAAGCTAAGGAGAG
CAGCATGAAGGTAGTTGGGAAGGGCACAGGCTTTGGAGTCAGCACATGT
```
] SEQ. ID NO: 19

SEQ. ID NO: 38

CCCCTGGTTGAAGCGTTGGAATCCCACTCTTTGGANNNNNNNAGATTGTGTTAGA
CTGTTAACCAGATTCCACAGCCAGGCAGAACTATGTCTGTCTCATCCATGTGTCA
GGGATTACGTCTcccatttgtcccaactggTTGTATCTCAAGCATGAATTCAGCT
TTTCCTTAAAGTCACTTCATTTTTATTTTCAGtgaagaactgttctaccagatac
tcatttatgatttttgccaatttTggtgttctcaggttatcgGTAAGTTTAGATCC
TTTTCACTTctgacatttcaactgaccgCCCCGCAAACAGTAGCTCTCCACTAAA
TA

SEQ. ID NO: 20

SEQ. ID NO: 39

-19 of splice acceptor site is A in some people. Others
heterozygous for A and G. GTCACTTC or CTCGCTTC (Polymorphism)

16: 18184 to 18314  (1732 TO 1896)

CATTTATGGTTTCTCACCTGCCATTCTGATAGTGGATTCTTGGGAATTCAGGCTT
catttggatgctccgttaaagcTTGCTCCTTCATGTTCTTGCTTCTTCCTAGgag
ccagcaccgctcttTgaccttgccatgcttgccttagatagtccagagagtggct
ggacagaggaagatggtcccaaagaaggacttgctgaatacattgttgagtttct
gaagaagaaggctgagatgcttgcagaccatttctctttggaaattgatgagGTG
TGACAGCCATTCTTATACTTCTGTTGTATTCTCcaaataaaatttccagccgggt
gCATTGGCTCA

SEQ. ID NO: 21

SEQ. ID NO: 40

17: 18429 to 18315  (1897 TO 1989)

CAGATAGGAGGCACAAGGCCTGggaaaggcactggagaaatgggATTTGTTTAAA
CTATGACAGCATTATTTCTTGTTCCCTTGTCCTTTTTCCTGCAAGCAGgaaggga
acctgattggattacccCTTCTGATTGACAACTATGTGCCCCTTTGGAGGGACT
gcctatcttcattcttcgactagccactgagGTCAGTGATCAAGCAGATACTAAG
CATTTcggtacatgcatgtgtgctggagggAAAGGGCAAA

SEQ. ID NO: 22

SEQ. ID NO: 41

18: 18444 to 18581  (1990 TO 2103)

CTATATCTTCCCAGCAATATTCACAGTCCGTTTACAGTTTTAACGCCTAAAGTAT
CACATTTCGTTTTTTAGCTTtaagtagtctgtgatctccgTTTAGAATGAGAATG
TTTAAATTCGTACCTATTTTGAGGTATTGAATTTCTTTGGACCAGgtgaattggg
acgaagaaaaggaatgttttgaaagcctcagtaaagaatgcgctatgttctattc
catccggaagcagtacatatctgaggagtcgaccctctcaggccagcagGTACAG
TGGTGATGCACACTGGCACCCCAGGACTAggacaggacctcatacatCTTAGGAG
ATGAAACTTG

SEQ. ID NO: 23

SEQ. ID NO: 42

Figure 4A (cont'd)

19: 18638 to 18637    (2104 TO 2271).    2463 is end of cDNA.

AATCCTCTTGTGTTCAGGCCTGTGGATCCCTGAGAGGCTAGCCCACAAGATCCAC
TTCAAAAGCCCTAGATAACACCAAGTCTTTCCAGACCCAGTGCACATCCCATCAG
CCAGgacaccagtgtatgttggGATGCAAACAGGGAGGCTTATGACATCTAATGT
GTTTTCCAGagtgaagtgcctggctccattccaaactcctggaagtggactgtgg
aacacattgtctataaagccttgcgctcacacattctgcctcctaaacatttcac
agaagatggaaatatcctgcagcttgctaacctgcctgatctatacaaagtcttt
gagaggtgttaaatatggttattt atgcactgtgggatgtgttcttctttctctg
tattccgatacaaagtgttgtatc aaagtgtgatatacaaagtgtaccaacataa
gtgttggtagcacttaagactgtat acttgccttctgatagtattcctttatacac
agtggattgattataaataaatag atgtgtcttaacataAATTTCTTATTTAATTT
TATTATGTATATA

SEQ. ID NO: 24

SEQ. ID NO: 43

Figure 4A (cont'd)

hMLH1 EXON AMPLIFICATION PRIMERS

| | First Stage Amplification Primer | SEQ. ID NO: | Second Stage Amplification Primer | SEQ. ID NO: |
|---|---|---|---|---|
| Exon 1 | N-18442- 5'aggcactgaggtgattggc<br>C-19109- 5'tcgtagcccttaagtgagc | 44<br>45 | N-19295- 5'tgtaaaacgacggccagtcactgaggtgattggctgaa<br>C-19446- *5'tagcccttaagtgagcccg | 83<br>84 |
| Exon 2 | N-19689- 5'aatatgtacattagagtagttg<br>C-19688- 5'cagagaaaggtcctgactc | 46<br>47 | N-18685- 5'tgtaaaacgacggccagtacattagagtagttgcaga<br>C-19067- *5'aggtcctgactcttccatg | 85<br>86 |
| Exon 3 | N-19687- 5'agagatttggaaaatgagtaac<br>C-19786- 5'acaatgtcatcacaggagg | 48<br>49 | N-18687- 5'tgtaaaacgacggccagtttggaaaatgagtaacatgatt<br>C-19068- *5'tgtcatcacaggaggatat | 87<br>88 |
| Exon 4 | N-18492- 5'aacctttcctttggtgtgagg<br>C-18421- 5'gattactctgagacctaggc | 50<br>51 | N-19294- 5'tgtaaaacgacggccagtctttccctttggtgaggtga<br>C-19077- *5'tactctgagacctaggcca | 89<br>90 |
| Exon 5 | N-18313- 5'gattttctcttttcccttggg<br>C-18179- 5'caaacaaagcttcaacaattac | 52<br>53 | N-19301- 5'tgtaaaacgacggccagttctttttcccttgggattag<br>C-19046- *5'acaaagcttcaacaattactct | 91<br>92 |

Figure 4B

| First Stage Amplification Primer | SEQ. ID NO: | Second Stage Amplification Primer | SEQ ID NO: |
|---|---|---|---|
| Exon 6 | | | |
| N-18318- 5'gggttttatttcaagtactictatg<br>C-18317- 5'gctcagcaactgttcaatgtatgagc | 54<br>55 | N-19711- 5'tgtaaaacgacggccagtgttatttcaagtacttcatgaatt<br>C-19079- *5'cagcaactgttcaatgtatgagcact | 93<br>94 |
| Exon 7 | | | |
| N-19009- 5'ctagtgtgttttggc<br>C-19135- 5'cataacctatctccacc | 56<br>57 | N-19293- 5'tgtaaaacgacggccagtgtgtgtgttttggcaac<br>C-19435- *5'aaccttatctccaccagc | 95<br>96 |
| Exon 8 | | | |
| N-18197- 5'ctcagccatgagacaataaatcc<br>C-18924- 5'ggttcccaaataatgtgatgg | 58<br>59 | N-19329- 5'tgtaaaacgacggccagtagccatgagacaataatccttg<br>C-19450- *5'tcccaaataatgtgatggaatg | 97<br>98 |
| Exon 9 | | | |
| N-18765- 5'caaaagcttcagaatctc<br>C-18198- 5'ctgtgggtgtttcctgtgagtgg | 60<br>61 | N-19608- 5'-tgtaaaacgacggccagtaagcttcagaatctcttt<br>C-19449- *5'-tgggtgtttcctgtgagtggatt | 99<br>100 |
| Exon 10 | | | |
| N-18305- 5'catgactttgtgaatgtacacc<br>C-18306- 5'gaggagcctgatagaacatctg | 62<br>63 | N-19297- 5'tgtaaaacgacggccagtacttgtgaatgtacacctgtg<br>C-19081- *5'gagagcctgatagaacatctgttg | 101<br>102 |

Figure 4B (cont'd)

| First Stage Amplification Primer | SEQ. ID NO: | Second Stage Amplification Primer | SEQ. ID NO: |
|---|---|---|---|
| Exon 11 | | | |
| N-18182- 5'gggcttttctcccctccc | 64 | N-19486- 5'tgtaaaacgacggccagtcttttctcccctcccacta | 103 |
| C-19041- 5'aaaatctgggctctcacg | 65 | C-19455- *5'tctgggctctcacgtct | 104 |
| Exon 12 (See note at end) | | | |
| N-18579- 5'aattatacctcatactagc | 66 | N-20546- *5'cttattctgagtctctcc | 105 |
| C-18178- 5'gttttattacagaataaggagg | 67 | C-20002- 5'tgtaaaacgacggccagtgtttgctcagaggctgc | 106 |
| | | N-19829- *5'gatgttcgtacagattcccg | 107 |
| | | C-19385- 5'tgtaaaacgacggccagttattacagaataaggaggtag | 108 |
| Exon 13 | | | |
| N-18420- 5'tgcaacccacaaatttggc | 69 | N-19300- 5'tgtaaaacgacggccagtaaccccacaaaatttggctaag | 109 |
| C-18443- 5'cttttccatttccaaaacc | 70 | C-19078- *5'tctccatttccaaaaccttg | 110 |
| Exon 14 | | | |
| N-19028- 5'tggtgtctctagttctgg | 71 | N-19456- *5'tgtctctagttctggtgc | 111 |
| C-18897- 5'catgttgtagtagctctgc | 72 | C-19472- 5'tgtaaaacgacggccagtgttgtagtagctctgcttg | 112 |
| Exon 15 | | | |
| N-19025- 5'cccatttgtccaactgg | 73 | N-19697- *5'atttgtccaactgttgta | 113 |
| C-18575- 5'cggtcagttgaaatgtcag | 74 | C-19466- 5'tgtaaaacgacggccagtcagttgaaatgtcagaagtg | 114 |

Figure 4B (cont'd)

| First Stage Amplification Primer | SEQ. ID NO: | Second Stage Amplification Primer | SEQ. ID NO: |
|---|---|---|---|
| Exon 16 | | | |
| N-18184- 5'catttggatgctccgttaaagc | 75 | N-19269- 5'tgtaaaacgacggccagt | 115 |
| C-18314- 5'cacccggctggaaatttatttg | 76 | C-19047- *5'ccggctgaaatttatttggag | 116 |
| Exon 17 | | | |
| N-18429- 5'ggaaaggcactggagaatggg | 77 | N-19298- 5'tgtaaaacgacggccagtaggcactggagaaatgggatttg | 117 |
| C-18315- 5'ccctccagcacacatgtaccg | 78 | C-19080- *5'tccagcacacatgtaccgaaat | 118 |
| Exon 18 | | | |
| N-18444- 5'taagtagtctgtgatctccg | 79 | N-19436- *5'tagtctgtgatctccgttt | 119 |
| C-18581- 5'atgtatgaggtcctgtcc | 80 | C-19471- 5'tgtaaaacgacggccagttatgaggtcctgtcctag | 120 |
| Exon 19 | | | |
| N-18638- 5'gacaccagtgtattgg | 81 | N-19447- *5'accagtgtagttgggatg | 121 |
| C-18637- 5'gagaagagaacacatccc | 82 | C-19330- 5'tgtaaaacgacggccagtgaaagaagaacacatcccaca | 122 |

All sequence reads 5' to 3'. Primer identification numbers are listed before each primer sequence. N indicates the primer on the 5' side of the exon. C indicates the primer on the 3' side of the exon. * indicates that the 5' nucleotide is biotinylated.

Figure 4B (cont'd)

Note on Primer properties.

Exons 1-7, 10, 13, 16-19 can be specifically amplified in PCR reactions containing either 1.5 mM or 3 mM MgCl2. Exons 11, 14 can only be specifically amplified in PCR reactions containing 1.5 mM MgCl2 and exons 8, 9, 12, 15 can only be specifically amplified in PCR reactions containing 3 mM MgCl2.

Important comments.

Alternate primers.

| | SEQ. ID NO: |
|---|---|
| Exon 12 | |
| N-18178 alternate is 19070-5'aagccaaagttagaaggca | 68 |

SEQ ID NOS: 5 and 123

|  | SEQ ID NO: |
|---|---|
| human MLH1 affected | VNRIAAGEVIQRPANAIKEMIENCLDAKFTSIQVIVKEGGLKLIQIQDNGTGIRKEDLDIVCER — 124 |
| human MLH1 normal | VNRIAAGEVIQRPANAIKEMIENCLDAKSTSIQVIVKEGGLKLIQIQDNGTGIRKEDLDIVCER — 125 |
| mouse MLH1 | .......PANAIKEMIENCLDAKSTNIQVVVKEGGLKLIQIQDNGTGIRKEDLDIVCER — 126 |
| S. cerevisiae MLH1 | VNKIAAGEIIISPVNALKEMMENSIDANATMIDILVKEGGIKVLQITDNGSGINKADLPILCER — 127 |
| S. cerevisiae PMS1 | VHRITSGQVITDLTTAVKELVDNSIDANANQIEIIFKDYGLESIECSDNGDGIDPSNYEFLALK — 128 |
| E. coli MutL | ANQIAAGEVVERPASVVKELVENSLDAGATRIDIDIERGGAKLIRIRDNGCGIKKDELALALAR — 129 |
| S. typhimurium MutL | ANQIAAGEVVERPASVVKELVENSLDAGATRVDIDIERGGAKLIRIRDNGCGIKKEELALALAR — 130 |
| S. pneumoniae HexB | ANQIAAGEVIERPASVCKELVENAIDAGSSQIIIEIEEAGLKKVQITDNGHGIAHDEVELALRR — 131 |

Figure 9

SEQ ID NO: 132

Figure 10

Figure 11 human mlh1 cDNA

```
   1 GCACGAGCTC GTGCCGTTTA GATGCAAAAT CCACAAGTAT TCAAGTGATT GTTAAAGAGG GAGGCCTGAA GTTGATTCAG   80
  81 ATCCAAGACA ATGGCACCGG GATCAGGAAA GAAGATCTGG ATATTGTATG TGAAAGGTTC ACTACTAGTA AACTGCAGTC  160
 161 CTTTGAGGAT TTAGCCAGTA TTTCTACCTA TGGCTTTCGA GGTGAGCTT TGGCCAGCAT TCAGATGGAA AAGCCATGTG CCCTCCTAAA  240
 241 CTATTACAAC GAAAACAGCT GATGGAAAGT GTGCATACAG AGCAAGTTAC TCAGATAGCC ACGAGAGAA AACTGAAAGC AAGCTTTAAA  320
 321 CCATGTGCTG GCAATCAAGG GACCCAGATC ACGGTGGAGG ACCTTTTTA CAACATAGCC CAGCAGACAA AGTTTCTCAG  400
 401 AAATCCAAGT GAAGAATATG GGAAAATTTT GGAAGTTGTT GGCAGGTATT CAGGTCACAA TGCAGGCATT CTCCATCTTT  480
 481 TTAAAAACA AGGAGAGACA GTAGCTGATG TTAGGACACT ACCCAATGCC TCAACCGTGG ACAATATTCG GTTACATATC  560
 561 GGAAATGCTG TTAGTCGAGA ACTGATAGAA ATTGGATGTG AGGATAAAAC CCTAGCCTTC AAAATGAATG TCCTGAGAA  640
 641 CAATGCAAAC TACTCAGTGA AGAAGTGCAT CTTCTTACTC TGCCCAAAAA TTCATCAACC ATCGTCTGGT AGAATCAACT  720
 721 AAGCCATAGA AACAGTGTAT GCAGCCTATT TGCCCAAAAA CACACACCCA TTCACTTCCT CACGAGGAG AGCATCCTGG AATCAGTCCC  800
 801 CAGAATGTGG ATGTTAATGT GCACCCCACA AAGCATGAAG TTCACTTCCT CACCAGACAG TTTGCTACCA AGCGGGTGCA  880
 881 GCAGCACATC GAGAGCAAGC TCCTGGGCTC CAATTCCTCC AGGATGTACT TCACCCAGAC TTTGCTACCA GGACTTGCTG  960
 961 GCCCCTCTGG GGAGATGGTT AAATCCACA ACGAAGCTT CTGTCTTCT ACTTCTGTGA GTAGTGATAA GGTCTATGCC  1040
1041 CACCAGATGG TTCGTACAGA CAGTCGAGA AGAAGCTT ATGCATTTCT GCAGCCTCTG AGCAAACCCC TGTCCAGTCA  1120
1121 GCCCAGGCC ATTGTCACAG AGGATAAGAC CGATATTTCT AGTGGCAGGA CTAGGCAGCA AGATGAGGAG ATGCTTGAAC  1200
1201 TCCCAGCCCC TGCTGAAGTG GCTGCCAAAA ATCAGAGCTT ACAACAAAGG GGACTTCAGA AATGTCAGAG GATCCCGAAA  1280
1281 AAGAGAGACT CTACTTCCAG CAACCCCAGA AAGAACATC TTGTGAAAT GGTGGAAGAT CCTCAGTGGG CCTTGGCACA  1360
1361 GGAAATGACT GCAGCTCTCA GGTTCTCCG GGAGATGTTG CCCCGGAGAA TTCTCAACAC TGTGAACATT GCCCCTCCAG  1440
1441 CAGGGACATG AAGTTATACC AAGTTATACC TTATCGGAGC CCCAAGCTT CAGCACCGCT CTTTGACCTT GAGTTTCTG CTGGAGTGAAT CCCAGAGT  1520
1521 GCATCAAACC TGTTCTCAGG TCTTCAACAC TTATCGGAGC CCCAAGCTT CAGCACCGCT CTTTGACCTT GAGTTTCTG CTGGAGTGAAT  1600
1601 CCAATTTGG TGTCCGACAG AGGAAGATGG TCCCAAAGAA GGACTTGCTG AATACATTGT TGAGTTTCTG AAGAAGAAGG CTGAGATGCT  1680
1681 GGCTGGACAG TTTCTTTTGG AAATTGATGA GGACTTGCTG AATACATTGT TGAGTTTCTG AAGAAGAAGG CTGAGATGCT  1760
1761 TGCAGACTAT AAGCAGCAG TTTCATTCTC GACTAGCCAC ATCCGGAAGC TGGGAGAAC AAAAGGAATG TTTTGAAAGC  1840
1841 CTTTGGAGGG AATGCGCTAT GTTCTATTCC ATCCGGAAGC TGGGAGAAC AAAAGGAATG TTTTGAAAGC  1920
1921 CTCAGTAAAG ACTGCCTATC CAAACTCCTG GAAGTGGACT AGTACATATC ACCCTCTGCG GCCAGCAGAG TCACACATTC  2000
2001 TGAAGTGCCT GGCTCCATTC CATTTCACAG AAGATGGAAA TATCCTGCAG GTGAACACA TTGCTCTAAC AGCCTTGAAGTC TTTGAGAGGT  2080
2081 TGCCCCTAA CATTTCACAG TTATTTATGC ACTGTGGGAA TATCCTGCAG TTGCTCTAAC AGCCTTGAAGTC TTTGAGAGGT  2160
2161 GTAAATATGG TTATTTATGC GTGCCAACAT AAGTGTTGGT ACTTATACTT TCCTGATCTT GCCTTCTGAT AGTGTTCCTT CAAAGTGA  2240
2241 TATACAAAGT GTGCCAACAT AAGTGTTGGT AACATAAAAA AAAAAAAAA AGGGGGGCC CGGTA  2320
2321 GGATTGATTA TAAATAAATA GATGTGTCTT
```

SEQ ID NO: 145

Figure 12

```
human mlh1 cDNA 5'end
         10         20         30         40         50         60         70         80
  1 CCCCCCTGA GGTCGACGGT ATCGATAAGC TTGATATCGA ATTCCTCGAG GCCACGAAGG CCCCATGGAG CGAGCTGAGA  80
 81 GCTCGAGTAC AGAACCTGCT AAGGCCATCA AACCTATTGA TCGGAAGTCA GTCCATCAGA TTTGCTCTGG GCCGGTGGTA  16
161 CCGAGTCTAA GCACTGCGGT GAAGGAGTTA GTAGAAAACA GTCTGGATGC TGGTGCCACT AATATTGATC TAAAGCTTAA  24
241 GGACTATGGA GTGGATCTCA TTGAAGTTTC AGGCAATGGA TGTGGGGTAG AAGAAGAAAA CTTCGAAGGC TTAACTCTGA  32
321 AACATCACAC ATCTAAGATT CAAGAGTTTG CCGACCTACC TCAGGTTGAA ACTTTTGGCT TTCGGGGGGA AGCTCTGAGC  40
401 TCACTTTGTG CACTGAGTGA TGTCACCATT TCTACCTGCC ATGTATCGGC GAAGGTTGGG ACTCGACTGG TGTTTGATCA  48
481 CTATGGGAAA ATCATCCAGA AAACCCCCTA CCCCACCCCC AGAGGGATGA CAGTCAGTGT GAAGCAGTTA TTTTCTACGC  56
561 TACCTGTGCA CCATAAAGAA TTTCAAAGAA ATATTAAGAA GAAACGTGCC TGCTTCCCTT CGCCTTCTGC CGTGATTGTC  64
641 AGTTTCCTGA GGCCTCCCCA GCCATGCTTC CTGTACAGCC TGCAGAACTA TGGATTCTTG CTCTGTCACC CAGGCTGGAG  72
721 TGCAATGCCT CGATGTCTGC TGACTGCAAC TGACTGCAAC TAGTTCTCCT GCCTCGGCCT CCTGAGTAGC  80
801 TGGGATTACA GGCATGAGCA C                                                                 82 human mlh1 cDNA 3'end
         10         20         30         40         50         60         70         80
  1 AACCGAGGCA AAAAAAAAAT CAATTGAAGG AGTTGCCGGG AAAAAACCCA ATGTGGGAAA TTAAAAGGCC AAATTCCCGG  80
 81 CAAAGAAAAC CTCAATTTTA AACACCCCTC CCCGGGGAGG GGAAAACCCT AAACTCCCAA GACCTCTTTA TTGAACTTGT  16
161 CTTGAAAGAA GCCTGGAAGA TTAAGAAAGA TGGCCTTGAT TTGTTATCGT GAAATGCTCA ATTCACTGAA AGGCTAAACT  24
241 GATTGCCTTG CCAACTAGTC AAAACTGAAC CTTCGGGACC CAGGACGTC GATGAACTGA TCTTCATGCT GAGCGACAGC  32
321 CCTGGGTCA TGTGCCGACC TTCCCGAGTC AAGCAGATGT TGCCTCCAG AGCCTGCCGG AAGTCGGTGA TGATTGGGAC  40
401 TGCTTCTCAAC ACAAGCGAAT GAGAAACTG ATCATCCACA TGGGGAGAT GGGCCACCCC TGGAACTGTC CCCATGGAAG  48
481 GCCACCATGA GACACATCGC CAACCTGGGT GTCATTTCTC AGAACTGACC GTAGTCACTG TATGGAATAA TTGGTTTTAT  56
561 CGCAGATTTT TATGTTTTGA AAGACAGAGT CTTCACTAAC CTTTTTTGTT TTAAAATGAA ACCTGCGGCC CTCGTGCCCT  64
641 CGAGGAATTC C                                                                            65
```

SEQ ID NO: 146

SEQ ID NO: 147

Figure 13 hMLH1 PCR region (primers excluded) 178 nucleotides

CTGTTTAGATGCAAAATCCACAAGTATTCAAGTGATTGTTAAAGAGGGAGGCC
TGAAGTTGATTCAGATCCAAGACAATGGCACCGGGATCAGGAAAGAAGATCTG
GATATTGTATGTGAAAGGTTCACTACTAGTAAACTGCAGTCCTTTGAGGATTT
AGCCAGTATTTCTACCTAT

SEQ ID NO: 148

Figure 14 hPMS1 PCR region (primers excluded) 178 nucleotides

CAGTCTGGATGCTGGTGCCACTAATATTGATCTAAAGCTTAAGGACTATGGAG
TGGATCTTATTGAAGTTTCAGACAATGGATGTGGGGTAGAAGAAGAAAACTTC
GAAGGCTTAACTCTGAAACATCACACATCTAAGATTCAAGAGTTTGCCGACCT
AACTCAGGTTGAAACTTTT

SEQ ID NO: 149

Figure 15

SEQUENCE LISTING (1) GENERAL INFORMATION:

(iii) NUMBER OF SEQUENCES: 148

(2) INFORMATION FOR SEQ ID NO:1:

(i) SEQUENCE CHARACTERISTICS:
       (A) LENGTH: 361 amino acids
       (B) TYPE: amino acid
       (C) STRANDEDNESS: single
       (D) TOPOLOGY: linear (ii) MOLECULE TYPE: cDNA (xi) SEQUENCE DESCRIPTION: SEQ ID NO:1:

```
Met Pro Ile Gln Val Leu Pro Pro Gln Leu Ala Asn Gln Ile Ala Ala
1               5                   10                  15

Gly Glu Val Val Glu Arg Pro Ala Ser Val Val Lys Glu Leu Val Glu
            20                  25                  30

Asn Ser Leu Asp Ala Gly Ala Thr Arg Val Asp Ile Asp Ile Glu Arg
        35                  40                  45

Gly Gly Ala Lys Leu Ile Arg Ile Arg Asp Asn Gly Cys Gly Ile Lys
    50                  55                  60

Lys Glu Glu Leu Ala Leu Ala Leu Ala Arg His Ala Thr Ser Lys Ile
65                  70                  75                  80

Ala Ser Leu Asp Asp Leu Glu Ala Ile Ile Ser Leu Gly Phe Arg Gly
                85                  90                  95

Glu Ala Leu Ala Ser Ile Ser Ser Val Ser Arg Leu Thr Leu Thr Ser
            100                 105                 110

Arg Thr Ala Glu Gln Ala Glu Ala Trp Gln Ala Tyr Ala Glu Gly Arg
        115                 120                 125

Asp Met Asp Val Thr Val Lys Pro Ala Ala His Pro Val Gly Thr Thr
    130                 135                 140

Leu Glu Val Leu Asp Leu Phe Tyr Asn Thr Pro Ala Arg Arg Lys Phe
145                 150                 155                 160

Met Arg Thr Glu Lys Thr Glu Phe Asn His Ile Asp Glu Ile Ile Arg
                165                 170                 175

Arg Ile Ala Leu Ala Arg Phe Asp Val Thr Leu Asn Leu Ser His Asn
            180                 185                 190

Gly Lys Leu Val Arg Gln Tyr Arg Ala Val Ala Lys Asp Gly Gln Lys
        195                 200                 205

Glu Arg Arg Leu Gly Ala Ile Cys Gly Thr Pro Phe Leu Glu Gln Ala
    210                 215                 220

Leu Ala Ile Glu Trp Gln His Gly Asp Lys Thr Lys Arg Gly Trp Val
225                 230                 235                 240

Ala Asp Pro Asn His Thr Thr Thr Ala Leu Thr Glu Ile Gln Tyr Cys
                245                 250                 255

Tyr Val Asn Gly Arg Met Met Arg Asp Arg Leu Ile Asn His Ala Ile
            260                 265                 270

Arg Gln Ala Cys Glu Asp Lys Leu Gly Ala Asp Gln Gln Pro Ala Phe
        275                 280                 285

Val Leu Tyr Leu Glu Ile Asp Pro His Gln Val Asp Val Asn Val His
    290                 295                 300

Pro Ala Lys His Glu Val Arg Phe His Gln Ser Arg Leu Val His Asp
305                 310                 315                 320
```

```
Phe Ile Tyr Gln Gly Val Leu Ser Val Leu Gln Gln Thr Glu Thr
                325                 330                 335

Ala Leu Pro Leu Glu Glu Ile Ala Pro Ala Pro Arg His Val Gln Glu
            340                 345                 350

Asn Arg Ile Ala Ala Gly Arg Asn His
        355                 360

(2) INFORMATION FOR SEQ ID NO:2:

(i) SEQUENCE CHARACTERISTICS:
        (A) LENGTH: 538 amino acids
        (B) TYPE: amino acid
        (C) STRANDEDNESS: single
        (D) TOPOLOGY: linear (ii) MOLECULE TYPE: cDNA (xi) SEQUENCE DESCRIPTION: SEQ ID NO:2:

Met Ser His Ile Ile Glu Leu Pro Glu Met Leu Ala Asn Gln Ile Ala
1               5                   10                  15

Ala Gly Glu Val Ile Glu Arg Pro Ala Ser Val Cys Lys Glu Leu Val
            20                  25                  30

Glu Asn Ala Ile Asp Ala Gly Ser Ser Gln Ile Ile Glu Ile Glu
        35                  40                  45

Glu Ala Gly Leu Lys Lys Val Gln Ile Thr Asp Asn Gly His Gly Ile
50                  55                  60

Ala His Asp Glu Val Glu Leu Ala Leu Arg Arg His Ala Thr Ser Lys
65                  70                  75                  80

Ile Lys Asn Gln Ala Asp Leu Phe Arg Ile Arg Thr Leu Gly Phe Arg
            85                  90                  95

Gly Glu Ala Leu Pro Ser Ile Ala Ser Val Ser Val Leu Thr Leu Leu
            100                 105                 110

Thr Ala Val Asp Gly Ala Ser His Gly Thr Lys Leu Val Ala Arg Gly
            115                 120                 125

Gly Glu Val Glu Glu Val Ile Pro Ala Thr Ser Pro Val Gly Thr Lys
130                 135                 140

Val Cys Val Glu Asp Leu Phe Phe Asn Thr Pro Ala Arg Leu Lys Tyr
145                 150                 155                 160

Met Lys Ser Gln Gln Ala Glu Leu Ser His Ile Ile Asp Ile Val Asn
            165                 170                 175

Arg Leu Gly Leu Ala His Pro Glu Ile Ser Phe Ser Leu Ile Ser Asp
            180                 185                 190

Gly Lys Glu Met Thr Arg Thr Ala Gly Thr Gly Gln Leu Arg Gln Ala
            195                 200                 205

Ile Ala Gly Ile Tyr Gly Leu Val Ser Ala Lys Lys Met Ile Glu Ile
210                 215                 220

Glu Asn Ser Asp Leu Asp Phe Glu Ile Ser Gly Phe Val Ser Leu Pro
225                 230                 235                 240

Glu Leu Thr Arg Ala Asn Arg Asn Tyr Ile Ser Leu Phe Ile Asn Gly
            245                 250                 255

Arg Tyr Ile Lys Asn Phe Leu Leu Asn Arg Ala Ile Leu Asp Gly Phe
            260                 265                 270

Gly Ser Lys Leu Met Val Gly Arg Phe Pro Leu Ala Val Ile His Ile
            275                 280                 285

His Ile Asp Pro Tyr Leu Ala Asp Val Asn Val His Pro Thr Lys Gln
            290                 295                 300
```

```
Glu Val Arg Ile Ser Lys Glu Lys Glu Leu Met Thr Leu Val Ser Glu
305                 310                 315                 320

Ala Ile Ala Asn Ser Leu Lys Glu Gln Thr Leu Ile Pro Asp Ala Leu
            325                 330                 335

Glu Asn Leu Ala Lys Ser Thr Val Arg Asn Arg Glu Lys Val Glu Gln
            340                 345                 350

Thr Ile Leu Pro Leu Ser Phe Pro Glu Leu Glu Phe Phe Gly Gln Met
            355                 360                 365

His Gly Thr Tyr Leu Phe Ala Gln Gly Arg Asp Gly Leu Tyr Ile Ile
        370                 375                 380

Asp Gln His Ala Ala Gln Glu Arg Val Lys Tyr Glu Glu Tyr Arg Glu
385                 390                 395                 400

Ser Ile Gly Asn Val Asp Gln Ser Gln Gln Leu Leu Val Pro Tyr
            405                 410                 415

Ile Phe Glu Phe Pro Ala Asp Asp Ala Leu Arg Leu Lys Glu Arg Met
            420                 425                 430

Pro Leu Leu Glu Glu Val Gly Val Phe Leu Ala Glu Tyr Gly Glu Asn
        435                 440                 445

Gln Phe Ile Leu Arg Glu His Pro Ile Trp Met Ala Glu Glu Glu Ile
    450                 455                 460

Glu Ser Gly Ile Tyr Glu Met Cys Asp Met Leu Leu Leu Thr Lys Glu
465                 470                 475                 480

Val Ser Ile Lys Lys Tyr Arg Ala Glu Leu Ala Ile Met Met Ser Cys
                485                 490                 495

Lys Arg Ser Ile Lys Ala Asn His Arg Ile Asp Asp His Ser Ala Arg
            500                 505                 510

Gln Leu Leu Tyr Gln Leu Ser Gln Cys Asp Asn Pro Tyr Asn Cys Pro
        515                 520                 525

His Gly Arg Pro Val Leu Val His Phe Thr
    530                 535

(2) INFORMATION FOR SEQ ID NO:3:

(i) SEQUENCE CHARACTERISTICS:
        (A) LENGTH: 607 amino acids
        (B) TYPE: amino acid
        (C) STRANDEDNESS: single
        (D) TOPOLOGY: linear (ii) MOLECULE TYPE: DNA (genomic)

(xi) SEQUENCE DESCRIPTION: SEQ ID NO:3:

Met Phe His His Ile Glu Asn Leu Leu Ile Glu Thr Glu Lys Arg Cys
1               5                   10                  15

Lys Gln Lys Glu Gln Arg Tyr Ile Pro Val Lys Tyr Leu Phe Ser Met
            20                  25                  30

Thr Gln Ile His Gln Ile Asn Asp Ile Asp Val His Arg Ile Thr Ser
        35                  40                  45

Gly Gln Val Ile Thr Asp Leu Thr Thr Ala Val Lys Glu Leu Val Asp
    50                  55                  60

Asn Ser Ile Asp Ala Asn Ala Asn Gln Ile Glu Ile Phe Lys Asp
65                  70                  75                  80

Tyr Gly Leu Glu Ser Ile Glu Cys Ser Asp Asn Gly Asp Gly Ile Asp
                85                  90                  95

Pro Ser Asn Tyr Glu Phe Leu Ala Leu Lys His Tyr Thr Ser Lys Ile
            100                 105                 110
```

-continued

```
Ala Lys Phe Gln Asp Val Ala Lys Val Gln Thr Leu Gly Phe Arg Gly
        115                 120                 125
Glu Ala Leu Ser Ser Leu Cys Gly Ile Ala Lys Leu Ser Val Ile Thr
    130                 135                 140
Thr Thr Ser Pro Pro Lys Ala Asp Lys Glu Leu Tyr Asp Met Val Gly
145                 150                 155                 160
His Ile Thr Ser Lys Thr Thr Thr Ser Arg Asn Lys Gly Thr Thr Val
                165                 170                 175
Leu Val Ser Gln Leu Phe His Asn Leu Pro Val Arg Gln Lys Glu Phe
                180                 185                 190
Ser Lys Thr Phe Lys Arg Gln Phe Thr Lys Cys Leu Thr Val Ile Gln
                195                 200                 205
Gly Tyr Ala Ile Ile Asn Ala Ala Ile Lys Phe Ser Val Trp Asn Ile
        210                 215                 220
Thr Pro Lys Gly Lys Lys Asn Leu Ile Leu Ser Thr Met Arg Asn Ser
225                 230                 235                 240
Ser Met Arg Lys Asn Ile Ser Ser Val Phe Gly Ala Gly Gly Met Arg
                245                 250                 255
Gly Glu Leu Glu Val Asp Leu Val Leu Asp Leu Asn Pro Phe Lys Asn
            260                 265                 270
Arg Met Leu Gly Lys Tyr Thr Asp Asp Pro Asp Phe Leu Asp Leu Asp
            275                 280                 285
Tyr Lys Ile Arg Val Lys Gly Tyr Ile Ser Gln Asn Ser Phe Gly Cys
        290                 295                 300
Gly Arg Asn Ser Lys Asp Arg Gln Phe Ile Tyr Val Asn Lys Arg Pro
305                 310                 315                 320
Val Glu Tyr Ser Thr Leu Leu Lys Cys Cys Asn Glu Val Tyr Lys Thr
                325                 330                 335
Phe Asn Asn Val Gln Phe Pro Ala Val Phe Leu Asn Leu Glu Leu Pro
                340                 345                 350
Met Ser Leu Ile Asp Val Asn Val Thr Pro Asp Lys Arg Val Ile Leu
        355                 360                 365
Leu His Asn Glu Arg Ala Val Ile Asp Ile Phe Lys Thr Thr Leu Ser
    370                 375                 380
Asp Tyr Tyr Asn Arg Gln Glu Leu Ala Leu Pro Lys Arg Met Cys Ser
385                 390                 395                 400
Gln Ser Glu Gln Gln Ala Gln Lys Arg Leu Leu Thr Glu Val Phe Asp
                405                 410                 415
Asp Asp Phe Lys Lys Met Glu Val Gly Gln Phe Asn Leu Gly Phe
                420                 425                 430
Ile Ile Val Thr Arg Lys Val Asp Asn Lys Ser Asp Leu Phe Ile Val
        435                 440                 445
Asp Gln His Ala Ser Asp Glu Lys Tyr Asn Phe Glu Thr Leu Gln Ala
    450                 455                 460
Val Thr Val Phe Lys Ser Gln Lys Leu Ile Ile Pro Gln Pro Val Glu
465                 470                 475                 480
Leu Ser Val Ile Asp Glu Leu Val Val Leu Asp Asn Leu Pro Val Phe
                485                 490                 495
Glu Lys Asn Gly Phe Lys Leu Lys Ile Asp Glu Glu Glu Phe Gly
                500                 505                 510
Ser Arg Val Lys Leu Leu Ser Leu Pro Thr Ser Lys Gln Thr Leu Phe
        515                 520                 525
```

```
Asp Leu Gly Asp Phe Asn Glu Leu Ile His Leu Ile Lys Glu Asp Gly
    530                 535                 540

Gly Leu Arg Arg Asp Asn Ile Arg Cys Ser Lys Ile Arg Ser Met Phe
545                 550                 555                 560

Ala Met Arg Ala Cys Arg Ser Ser Ile Met Ile Gly Lys Pro Leu Asn
                565                 570                 575

Lys Lys Thr Met Thr Arg Val Val His Asn Leu Ser Glu Leu Asp Lys
            580                 585                 590

Pro Trp Asn Cys Pro His Gly Arg Pro Thr Met Arg His Leu Met
        595                 600                 605
```

(2) INFORMATION FOR SEQ ID NO:4:

(i) SEQUENCE CHARACTERISTICS:
        (A) LENGTH: 2484 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:4:

```
CTTGGCTCTT CTGGCGCCAA AATGTCGTTC GTGGCAGGGG TTATTCGGCG GCTGGACGAG      60

ACAGTGGTGA ACCGCATCGC GGCGGGGGAA GTTATCCAGC GGCCAGCTAA TGCTATCAAA     120

GAGATGATTG AGAACTGTTT AGATGCAAAA TCCACAAGTA TTCAAGTGAT TGTTAAAGAG     180

GGAGGCCTGA AGTTGATTCA GATCCAAGAC AATGGCACCG GGATCAGGAA AGAAGATCTG     240

GATATTGTAT GTGAAAGGTT CACTACTAGT AAACTGCAGT CCTTTGAGGA TTTAGCCAGT     300

ATTTCTACCT ATGGCTTTCG AGGTGAGGCT TTGGCCAGCA TAAGCCATGT GGCTCATGTT     360

ACTATTACAA CGAAAACAGC TGATGGAAAG TGTGCATACA GAGCAAGTTA CTCAGATGGA     420

AAACTGAAAG CCCCTCCTAA ACCATGTGCT GGCAATCAAG GACCCAGAT CACGGTGGAG      480

GACCTTTTTT ACAACATAGC CACGAGGAGA AAAGCTTTAA AAAATCCAAG TGAAGAATAT     540

GGGAAAATTT TGGAAGTTGT TGGCAGGTAT TCAGTACACA ATGCAGGCAT TAGTTTCTCA     600

GTTAAAAAAC AAGGAGAGAC AGTAGCTGAT GTTAGGACAC TACCCAATGC CTCAACCGTG     660

GACAATATTC GCTCCATCTT TGGAAATGCT GTTAGTCGAG AACTGATAGA AATTGGATGT     720

GAGGATAAAA CCCTAGCCTT CAAAATGAAT GGTTACATAT CCAATGCAAA CTACTCAGTG     780

AAGAAGTGCA TCTTCTTACT CTTCATCAAC CATCGTCTGG TAGAATCAAC TTCCTTGAGA     840

AAAGCCATAG AAACAGTGTA TGCAGCCTAT TTGCCCAAAA ACACACACCC ATTCCTGTAC     900

CTCAGTTTAG AAATCAGTCC CCAGAATGTG GATGTTAATG TGCACCCCAC AAAGCATGAA     960

GTTCACTTCC TGCACGAGGA GAGCATCCTG GAGCGGGTGC AGCAGCACAT CGAGAGCAAG    1020

CTCCTGGGCT CCAATTCCTC CAGGATGTAC TTCACCCAGA CTTTGCTACC AGGACTTGCT    1080

GGCCCCTCTG GGGAGATGGT TAAATCCACA ACAAGTCTGA CCTCGTCTTC TACTTCTGGA    1140

AGTAGTGATA AGGTCTATGC CCACCAGATG GTTCGTACGA ATTCCCGGGA ACAGAAGCTT    1200

GATGCATTTC TGCAGCCTCT GAGCAAACCC CTGTCCAGTC AGCCCCAGGC CATTGTCACA    1260

GAGGATAAGA CAGATATTTC TAGTGGCAGG GCTAGGCAGC AAGATGAGGA GATGCTTGAA    1320

CTCCCAGCCC CTGCTGAAGT GGCTGCCAAA AATCAGAGCT TGGAGGGGGA TACAACAAAG    1380

GGGACTTCAG AAATGTCAGA AGAGAGGA CCTACTTCCA GCAACCCCAG AAAGAGACAT     1440

CGGGAAGATT CTGATGTGGA AATGGTGGAA GATGATTCCC GAAAGGAAAT GACTGCAGCT    1500

TGTACCCCCC GGAGAAGGAT CATTAACCTC ACTAGTGTTT TGAGTCTCCA GGAAGAAATT    1560
```

-continued

```
AATGAGCAGG GACATGAGGT TCTCCGGGAG ATGTTGCATA ACCACTCCTT CGTGGGCTGT    1620

GTGAATCCTC AGTGGGCCTT GGCACAGCAT CAAACCAAGT TATACCTTCT CAACACCACC    1680

AAGCTTAGTG AAGAACTGTT CTACCAGATA CTCATTTATG ATTTTGCCAA TTTTGGTGTT    1740

CTCAGGTTAT CGGAGCCAGC ACCGCTCTTT GACCTTGCCA TGCTTGCCTT AGATAGTCCA    1800

GAGAGTGGCT GGACAGAGGA AGATGGTCCC AAAGAAGGAC TTGCTGAATA CATTGTTGAG    1860

TTTCTGAAGA AGAAGGCTGA GATGCTTGCA GACTATTTCT CTTTGGAAAT TGATGAGGAA    1920

GGGAACCTGA TTGGATTACC CCTTCTGATT GACAACTATG TGCCCCCTTT GGAGGGACTG    1980

CCTATCTTCA TTCTTCGACT AGCCACTGAG GTGAATTGGG ACGAAGAAAA GGAATGTTTT    2040

GAAAGCCTCA GTAAGAATG CGCTATGTTC TATTCCATCC GGAAGCAGTA CATATCTGAG    2100

GAGTCGACCC TCTCAGGCCA GCAGAGTGAA GTGCCTGGCT CCATTCCAAA CTCCTGGAAG    2160

TGGACTGTGG AACACATTGT CTATAAAGCC TTGCGCTCAC ACATTCTGCC TCCTAAACAT    2220

TTCACAGAAG ATGGAAATAT CCTGCAGCTT GCTAACCTGC CTGATCTATA CAAAGTCTTT    2280

GAGAGGTGTT AAATATGGTT ATTTATGCAC TGTGGGATGG GTTCTTCTTT CTCTGTATTC    2340

CGATACAAAG TGTTGTATCA AAGTGTGATA TACAAAGTGT ACCAACATAA GTGTTGGTAG    2400

CACTTAAGAC TTATACTTGC CTTCTGATAG TATTCCTTTA TACACAGTGG ATTGATTATA    2460

AATAAATAGA TGTGTCTTAA CATA                                          2484
```

(2) INFORMATION FOR SEQ ID NO:5:

(i) SEQUENCE CHARACTERISTICS:
       (A) LENGTH: 756 amino acids
       (B) TYPE: amino acid
       (C) STRANDEDNESS: single
       (D) TOPOLOGY: linear (ii) MOLECULE TYPE: protein (xi) SEQUENCE DESCRIPTION: SEQ ID NO:5:

```
Met Ser Phe Val Ala Gly Val Ile Arg Arg Leu Asp Glu Thr Val Val
1               5                   10                  15

Asn Arg Ile Ala Ala Gly Glu Val Ile Gln Arg Pro Ala Asn Ala Ile
            20                  25                  30

Lys Glu Met Ile Glu Asn Cys Leu Asp Ala Lys Ser Thr Ser Ile Gln
        35                  40                  45

Val Ile Val Lys Glu Gly Gly Leu Lys Leu Ile Gln Ile Gln Asp Asn
50                  55                  60

Gly Thr Gly Ile Arg Lys Glu Asp Leu Asp Ile Val Cys Glu Arg Phe
65                  70                  75                  80

Thr Thr Ser Lys Leu Gln Ser Phe Glu Asp Leu Ala Ser Ile Ser Thr
                85                  90                  95

Tyr Gly Phe Arg Gly Glu Ala Leu Ala Ser Ile Ser His Val Ala His
            100                 105                 110

Val Thr Ile Thr Thr Lys Thr Ala Asp Gly Lys Cys Ala Tyr Arg Ala
        115                 120                 125

Ser Tyr Ser Asp Gly Lys Leu Lys Ala Pro Pro Lys Pro Cys Ala Gly
    130                 135                 140

Asn Gln Gly Thr Gln Ile Thr Val Glu Asp Leu Phe Tyr Asn Ile Ala
145                 150                 155                 160

Thr Arg Arg Lys Ala Leu Lys Asn Pro Ser Glu Glu Tyr Gly Lys Ile
                165                 170                 175
```

```
Leu Glu Val Val Gly Arg Tyr Ser Val His Asn Ala Gly Ile Ser Phe
            180                 185                 190

Ser Val Lys Lys Gln Gly Glu Thr Val Ala Asp Val Arg Thr Leu Pro
            195                 200                 205

Asn Ala Ser Thr Val Asp Asn Ile Arg Ser Ile Phe Gly Asn Ala Val
            210                 215                 220

Ser Arg Glu Leu Ile Glu Ile Gly Cys Glu Asp Lys Thr Leu Ala Phe
225                 230                 235                 240

Lys Met Asn Gly Tyr Ile Ser Asn Ala Asn Tyr Ser Val Lys Lys Cys
                245                 250                 255

Ile Phe Leu Leu Phe Ile Asn His Arg Leu Val Glu Ser Thr Ser Leu
            260                 265                 270

Arg Lys Ala Ile Glu Thr Val Tyr Ala Ala Tyr Leu Pro Lys Asn Thr
            275                 280                 285

His Pro Phe Leu Tyr Leu Ser Leu Glu Ile Ser Pro Gln Asn Val Asp
            290                 295                 300

Val Asn Val His Pro Thr Lys His Glu Val His Phe Leu His Glu Glu
305                 310                 315                 320

Ser Ile Leu Glu Arg Val Gln Gln His Ile Glu Ser Lys Leu Leu Gly
                325                 330                 335

Ser Asn Ser Ser Arg Met Tyr Phe Thr Gln Thr Leu Leu Pro Gly Leu
            340                 345                 350

Ala Gly Pro Ser Gly Glu Met Val Lys Ser Thr Thr Ser Leu Thr Ser
            355                 360                 365

Ser Ser Thr Ser Gly Ser Ser Asp Lys Val Tyr Ala His Gln Met Val
            370                 375                 380

Arg Thr Asp Ser Arg Glu Gln Lys Leu Asp Ala Phe Leu Gln Pro Leu
385                 390                 395                 400

Ser Lys Pro Leu Ser Ser Gln Pro Gln Ala Ile Val Thr Glu Asp Lys
                405                 410                 415

Thr Asp Ile Ser Ser Gly Arg Ala Arg Gln Gln Asp Glu Glu Met Leu
            420                 425                 430

Glu Leu Pro Ala Pro Ala Glu Val Ala Ala Lys Asn Gln Ser Leu Glu
            435                 440                 445

Gly Asp Thr Thr Lys Gly Thr Ser Glu Met Ser Glu Lys Arg Gly Pro
            450                 455                 460

Thr Ser Ser Asn Pro Arg Lys Arg His Arg Glu Asp Ser Asp Val Glu
465                 470                 475                 480

Met Val Glu Asp Asp Ser Arg Lys Glu Met Thr Ala Ala Cys Thr Pro
                485                 490                 495

Arg Arg Arg Ile Ile Asn Leu Thr Ser Val Leu Ser Leu Gln Glu Glu
            500                 505                 510

Ile Asn Glu Gln Gly His Glu Val Leu Arg Glu Met Leu His Asn His
            515                 520                 525

Ser Phe Val Gly Cys Val Asn Pro Gln Trp Ala Leu Ala Gln His Gln
            530                 535                 540

Thr Lys Leu Tyr Leu Leu Asn Thr Thr Lys Leu Ser Glu Glu Leu Phe
545                 550                 555                 560

Tyr Gln Ile Leu Ile Tyr Asp Phe Ala Asn Phe Gly Val Leu Arg Leu
                565                 570                 575

Ser Glu Pro Ala Pro Leu Phe Asp Leu Ala Met Leu Ala Leu Asp Ser
            580                 585                 590

Pro Glu Ser Gly Trp Thr Glu Glu Asp Gly Pro Lys Glu Gly Leu Ala
```

```
            595                 600                 605
Glu Tyr Ile Val Glu Phe Leu Lys Lys Lys Ala Glu Met Leu Ala Asp
610                 615                 620

Tyr Phe Ser Leu Glu Ile Asp Glu Glu Gly Asn Leu Ile Gly Leu Pro
625                 630                 635                 640

Leu Leu Ile Asp Asn Tyr Val Pro Pro Leu Glu Gly Leu Pro Ile Phe
                645                 650                 655

Ile Leu Arg Leu Ala Thr Glu Val Asn Trp Asp Glu Lys Glu Cys
            660                 665                 670

Phe Glu Ser Leu Ser Lys Glu Cys Ala Met Phe Tyr Ser Ile Arg Lys
            675                 680                 685

Gln Tyr Ile Ser Glu Glu Ser Thr Leu Ser Gly Gln Gln Ser Glu Val
690                 695                 700

Pro Gly Ser Ile Pro Asn Ser Trp Lys Trp Thr Val Glu His Ile Val
705                 710                 715                 720

Tyr Lys Ala Leu Arg Ser His Ile Leu Pro Pro Lys His Phe Thr Glu
                725                 730                 735

Asp Gly Asn Ile Leu Gln Leu Ala Asn Leu Pro Asp Leu Tyr Lys Val
                740                 745                 750

Phe Glu Arg Cys
        755
```

(2) INFORMATION FOR SEQ ID NO:6:

(i) SEQUENCE CHARACTERISTICS:
        (A) LENGTH: 397 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

```
TGGCTGGATG CTAAGCTACA GCTGAAGGAA GAACGTGAGC ACGAGGCACT GAGGTGATTG    60

GCTGAAGGCA CTTCCGTTGA GCATCTAGAC GTTTCCTTGG CTCTTCTGGC GCCAAAATGT   120

CGTTCGTGGC AGGGGTTATT CGGCGGCTGG ACGAGACAGT GGTGAACCGC ATCGCGGCGG   180

GGGAAGTTAT CCAGCGGCCA GCTAATGCTA TCAAAGAGAT GATTGAGAAC TGGTACGGAG   240

GGAGTCGAGC CGGGCTCACT TAAGGGCTAC GACTTAACGG GCCGCGTCAC TCAATGGCGC   300

GGACACGCCT CTTTCCCCGG GCAGAGGCAT GTACAGCGCA TGCCCACAAC GGCGGAGGCC   360

GCCGGGTTCC CTACGTGCCA TAAGCCTTCT CCTTTTC                            397
```

(2) INFORMATION FOR SEQ ID NO:7:

(i) SEQUENCE CHARACTERISTICS:
        (A) LENGTH: 393 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

```
AAACACGTTA ATGAGGCACT ATTGTTTGTA TTTGGAGTTT GTTATCATTG CTTGGCTCAT    60

ATTAAAATAT GTACATTAGA GTAGTTGCAG ACTGATAAAT TATTTTCTGT TTGATTTGCC   120

AGTTTAGATG CAAAATCCAC AAGTATTCAA GTGATTGTTA AGAGGGAGG CCTGAAGTTG    180

ATTCAGATCC AAGACAATGG CACCGGGATC AGGGTAAGTA AAACCTCAAA GTAGCAGGAT   240
```

```
GTTTGTGCGC TTCATGGAAG AGTCAGGACC TTTCTCTGTT CTGGAAACTA GGCTTTTGCA      300

GATGGGATTT TTTCACTGAA AAATTCAACA CCAACAATAA ATATTTATTG AGTACCTATT      360

ATTTGCGGGG CACTGTTCAG GGGATGTGTC AGT                                  393
```

(2) INFORMATION FOR SEQ ID NO:8:

(i) SEQUENCE CHARACTERISTICS:
        (A) LENGTH: 352 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

```
TTTCCTGGAT TAATCAAGAA ATGGAATTCA AAGAGATTTG GAAAATGAGT AACATGATTA       60

TTTACTCATC TTTTTGGTAT CTAACAGAAA GAAGATCTGG ATATTGTATG TGAAAGGTTC      120

ACTACTAGTA AACTGCAGTC CTTTGAGGAT TTAGCCAGTA TTTCTACCTA TGGCTTTCGA      180

GGTGAGGTAA GCTAAAGATT CAAGAAATGT GTAAAATATC CTCCTGTGAT GACATTGTCT      240

GTCATTTGTT AGTATGTATT TCTCAACATA GATAAATAAG GTTTGGTACC TTTTACTTGT      300

TAAATGTATG CAAATCTGAG CAAACTTAAT GAACTTTAAC TTTCAAAGAC TG             352
```

(2) INFORMATION FOR SEQ ID NO:9:

(i) SEQUENCE CHARACTERISTICS:
        (A) LENGTH: 287 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

```
TGGAAGCAGC AGCAGATAAC CTTTCCCTTT GGTGAGGTGA CAGTGGGTGA CCCAGCAGTG       60

AGTTTTTCTT TCAGTCTATT TTCTTTTCTT CCTTAGGCTT TGGCCAGCAT AAGCCATGTG      120

GCTCATGTTA CTATTACAAC GAAAACAGCT GATGGAAAGT GTGCATACAG GTATAGTGCT      180

GACTTCTTTT ACTCATATAT ATTCATTCTG AAATGTATTT TGGGCCTAGG TCTCAGAGTA      240

ATCCTGTCTC AACACCAGTG TTATCTTTGG CAGAGATCTT GAGTACG                   287
```

(2) INFORMATION FOR SEQ ID NO:10:

(i) SEQUENCE CHARACTERISTICS:
        (A) LENGTH: 336 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:10:

```
TTGATATGAT TTTCTCTTTT CCCCTTGGGA TTAGTATCTA TCTCTCTACT GGATATTAAT       60

TTGTTATATT TTCTCATTAG AGCAAGTTAC TCAGATGGAA AACTGAAAGC CCCTCCTAAA      120

CCATGTGCTG GCAATCAAGG GACCCAGATC ACGGTAAGAA TGGTACATGG GAGAGTAAAT      180

TGTTGAAGCT TTGTTTGTAT AAATATTGGA ATAAAAAATA AAATTGCTTC TAAGTTTTCA      240

GGGTAATAAT AAAATGAATT TGCACTAGTT AATGGAGGTC CCAAGATATC CTCTAAGCAA      300

GATAAATGAC TATTGGCTTT TTGGCATGGC AGCCTG                               336
```

(2) INFORMATION FOR SEQ ID NO:11:

(i) SEQUENCE CHARACTERISTICS:
        (A) LENGTH: 275 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

```
GCTTTTGCCA GGACCATCTT GGGTTTTATT TTCAAGTACT TCTATGAATT TACAAGAAAA      60

ATCAATCTTC TGTTCAGGTG GAGGACCTTT TTTACAACAT AGCCACGAGG AGAAAAGCTT     120

TAAAAAATCC AAGTGAAGAA TATGGAAAAA TTTTGGAAGT TGTTGGCAGG TACAGTCCAA     180

AATCTGGGAG TGGGTCTCTG AGATTTGTCA TCAAAGTAAT GTGTTCTAGT GCTCATACAT     240

TGAACAGTTG CTGAGCTAGA TGGTGAAAAG TAAAA                                275
```

(2) INFORMATION FOR SEQ ID NO:12:

(i) SEQUENCE CHARACTERISTICS:
        (A) LENGTH: 389 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:12:

```
CAGCAACCTA TAAAAGTAGA GAGGAGTCTG TGTTTTGACG CAGCACCTTT AGCATTTTTA      60

TTTGGATGAA GTTTCTGCTG GTTTATTTTT CTGTGGGTAA AATATTAATA GGCTGTATGG     120

AGATATTTTT CTTATATGT ACCTTTGTTT AGATTACTCA ACTCCACTAA TTTATTTAAC      180

TAAAAGGGGG CTCTGACATC TAGTGTGTGT TTTTGGCAAC TCTTTTCTTA CTCTTTTGTT     240

TTTCTTTTCC AGGTATTCAG TACACAATGC AGGCATTAGT TTCTCAGTTA AAAAAGTAAG     300

TTCTTGGTTT ATGGGGATG GTTTTGTTTT ATGAAAAGAA AAAGGGGAT TTTTAATAGT       360

TTGCTGGTGG AGATAAGGTT ATGATGTTT                                       389
```

(2) INFORMATION FOR SEQ ID NO:13:

(i) SEQUENCE CHARACTERISTICS:
        (A) LENGTH: 381 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:13:

```
ATGTTTCAGT CTCAGCCATG AGACAATAAA TCCTTGTGTC TTCTGCTGTT TGTTTATCAG      60

CAAGGAGAGA CAGTAGCTGA TGTTAGGACA CTACCCAATG CCTCAACCGT GGACAATATT     120

CGCTCCATCT TTGGAAATGC TGTTAGTCGG TATGTCGATA ACCTATATAA AAAAATCTTT     180

TACATTTATT ATCTTGGTTT ATCATTCCAT CACATTATTT GGGAACCTTT CAAGATATTA     240

TGTGTGTTAA GAGTTTGCTT TAGTCAAATA CACAGGCTTG TTTTATGCTT CAGATTTGTT     300

AATGGAGTTC TTATTTCACG TAATCAACAC TTTCTAGGTG TATGTAATCT CCTAGATTCT     360

GTGGCGTGAA TCATGTGTTC T                                               381
```

(2) INFORMATION FOR SEQ ID NO:14:

(i) SEQUENCE CHARACTERISTICS:
        (A) LENGTH: 526 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:14:

```
ACTGAGTAGG GTAGGTGGGT GAGTGGGTGG GTGGGTGGGT GGGTGGATGG ATGGATGGGA      60
GGATGGGTGG GTGAATGGGT GAACAGACAA ATGGATGGAT GAATGGACAG GCACAGGAGG     120
ACCTCAAATG GACCAAGTCT TCGGGGCCCT CATTTCACAA AGTTAGTTTA TGGGAAGGAA     180
CCTTGTGTTT TTAAATTCTG ATTCTTTTGT AATGTTTGAG TTTTGAGTAT TTTCAAAAGC     240
TTCAGAATCT CTTTTCTAAT AGAGAACTGA TAGAAATTGG ATGTGAGGAT AAAACCCTAG     300
CCTTCAAAAT GAATGGTTAC ATATCCAATG CAAACTACTC AGTGAAGAAG TGCATCTTCT     360
TACTCTTCAT CAACCGTAAG TTAAAAAGAA CCACATGGGA AATCCACTCA CAGGAAACAC     420
CCACAGGGAA TTTTATGGGA CCATGGAAAA ATTTCTGAGT CCATAGGTTT GATTAAACAT     480
GGAGAAACCT CATGGCAAAG TTTGGTTTTA TTGGGAAGCA TGTATA                    526
```

(2) INFORMATION FOR SEQ ID NO:15:

(i) SEQUENCE CHARACTERISTICS:
        (A) LENGTH: 434 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:15:

```
ATAGTGGGCT GGAAAGTGGC CACAGGTAAA GGTGCACCTT TCTTCCTGGG GATGTGATGT      60
GCATATCACT ACAGAAATGT CTTTCCTGAG GTGATGTCAT GACTTTGTGT GAATGTACAC     120
CTGTGACCTC ACCCCTCAGG ACAGTTTTGA ACTGGTTGCT TTCTTTTTAT TGTTTAGATC     180
GTCTGGTAGA ATCAACTTCC TTGAGAAAAG CCATAGAAAC AGTGTATGCA GCCTATTTGC     240
CCAAAAACAC ACACCCATTC CTGTACCTCA GGTAATGTAG CACCAAACTC CTCAACCAAG     300
ACTCACAAGG AACAGATGTT CTATCAGGCT CTCCTCTTTG AAAGAGATGA GCATGCTAAT     360
AGTACAATCA GAGTGAATCC CATACACCAC TGGCAAAAGG ATGTTCTGTC CCTTCTTACA     420
GGTACAAGGC ACAG                                                       434
```

(2) INFORMATION FOR SEQ ID NO:16:

(i) SEQUENCE CHARACTERISTICS:
        (A) LENGTH: 458 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:16:

```
CTTACGCAAA GCTACACAGC TCTTAAGTAG CAGTGCCAAT ATTTGAACAC ACTCAGACTC      60
GAGCCTGAGG TTTTGACCAC TGTGTCATCT GGCCTCAAAT CTTCTGGCCA CCACATACAC     120
CATATGTGGG CTTTTTCTCC CCCTCCCACT ATCTAAGGTA ATTGTTCTCT CTTATTTTCC     180
TGACAGTTTA GAAATCAGTC CCCAGAATGT GGATGTTAAT GTGCACCCCA CAAAGCATGA     240
```

```
AGTTCACTTC CTGCACGAGG AGAGCATCCT GGAGCGGGTG CAGCAGCACA TCGAGAGCAA        300

GCTCCTGGGC TCCAATTCCT CCAGGATGTA CTTCACCCAG GTCAGGGCGC TTCTCATCCA        360

GCTACTTCTC TGGGGCCTTT GAAATGTGCC CGGCCAGACG TGAGAGCCCA GATTTTTGCT        420

GTTATTTAGG AACTTTTTTT GAAGTATTAC CTGGATAG                                458

(2) INFORMATION FOR SEQ ID NO:17:

(i) SEQUENCE CHARACTERISTICS:
        (A) LENGTH: 618 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:17:

GATAATTATA CCTCATACTA GCTTCTTTCT TAGTACTGCT CCATTTGGGG ACCTGTATAT         60

CTATACTTCT TATTCTGAGT CTCTCCACTA TATATATATA TATATATATA TTTTTTTTTT        120

TTTTTTTTTT TAATACAGAC TTTGCTACCA GGACTTGCTG GCCCCTCTGG GGAGATGGTT        180

AAATCCACAA CAAGTCTGAC CTCGTCTTCT ACTTCTGGAA GTAGTGATAA GGTCTATGCC        240

CACCAGATGG TTCGTACAGA TTCCCGGGAA CAGAAGCTTG ATGCATTTCT GCAGCCTCTG        300

AGCAAACCCC TGTCCAGTCA GCCCCAGGCC ATTGTCACAG AGGATAAGAC AGATATTTCT        360

AGTGGCAGGG CTAGGCAGCA AGATGAGGAG ATGCTTGAAC TCCCAGCCCC TGCTGAAGTG        420

GCTGCCAAAA ATCAGAGCTT GGAGGGGGAT ACAACAAAGG GGACTTCAGA AATGTCAGAG        480

AAGAGAGGAC CTACTTCCAG CAACCCCAGG TATGGCCTTT TGGGAAAAGT ACAGCCTACC        540

TCCTTTATTC TGTAATAAAA CTGCCTTCTA ACTTTGGCTT TTCATGAATC ACTTGCATCT        600

TCTCTCTGCC GACTTCCC                                                     618

(2) INFORMATION FOR SEQ ID NO:18:

(i) SEQUENCE CHARACTERISTICS:
        (A) LENGTH: 478 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:18:

CTGTGCTCCA GCACAGGTCA TCCAGCTCTG TAGACCAGCG CAGAGAAGTT GCTTGCTCCC         60

AAATGCAACC CACAAAATTT GGCTAAGTTT AAAAACAAGA ATAATAATGA TCTGCACTTC        120

CTTTTCTTCA TTGCAGAAAG AGACATCGGG AAGATTCTGA TGTGGAAATG GTGGAAGATG        180

ATTCCCGAAA GGAAATGACT GCAGCTTGTA CCCCCCGGAA AAGGATCATT AACCTCACTA        240

GTGTTTTGAG TCTCCAGGAA GAAATTAATG AGCAGGGACA TGAGGGTACG TAAACGCTGT        300

GGCCTGCCTG GGATGCATAG GGCCTCAACT GCCAAGGTTT TGGAAATGGA GAAAGCAGTC        360

ATGTTGTCAG AGTGGCACTA CAGTTTTGAT GGGCAAGCTC CTCTTCCTTT ACTAACCCAC        420

AATAGCATCA GCTTAAAGAC AATTTTTGAT TGGGAGAAAA GGGAGAAAAT AATCTCTG         478

(2) INFORMATION FOR SEQ ID NO:19:

(i) SEQUENCE CHARACTERISTICS:
        (A) LENGTH: 377 base pairs
        (B) TYPE: nucleic acid
```

(C) STRANDEDNESS: single
        (D) TOPOLOGY: linear (xi) SEQUENCE DESCRIPTION: SEQ ID NO:19:

```
CAGTTTTCAC CAGGAGGCTC AAATCAGGCC TTTGCTTACT TGGTGTCTCT AGTTCTGGTG      60

CCTGGTGCTT TGGTCAATGA AGTGGGGTTG GTAGGATTCT ATTACTTACC TGTTTTTTGG     120

TTTTATTTTT TGTTTTGCAG TTCTCCGGGA GATGTTGCAT AACCACTCCT TCGTGGGCTG     180

TGTGAATCCT CAGTGGGCCT TGGCACAGCA TCAAACCAAG TTATACCTTC TCAACACCAC     240

CAAGCTTAGG TAAATCAGCT GAGTGTGTGA ACAAGCAGAG CTACTACAAC AATGGTCCAG     300

GGAGCACAGG CACAAAAGCT AAGGAGAGCA GCATGAAGGT AGTTGGGAAG GGCACAGGCT     360

TTGGAGTCAG CACATGT                                                   377
```

(2) INFORMATION FOR SEQ ID NO:20:

(i) SEQUENCE CHARACTERISTICS:
        (A) LENGTH: 325 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:20:

```
CCCCTGGTTG AAGCGTTGGA ATCCCACTCT TTGGAAGATT GTGTTAGACT GTTAACCAGA      60

TTCCACAGCC AGGCAGAACT ATGTCTGTCT CATCCATGTG TCAGGGATTA CGTCTCCCAT     120

TTGTCCCAAC TGGTTGTATC TCAAGCATGA ATTCAGCTTT TCCTTAAAGT CACTTCATTT     180

TTATTTTCAG TGAAGAACTG TTCTACCAGA TACTCATTTA TGATTTTGCC AATTTTGGTG     240

TTCTCAGGTT ATCGGTAAGT TTAGATCCTT TTCACTTCTG ACATTTCAAC TGACCGCCCC     300

GCAAACAGTA GCTCTCCACT AAATA                                          325
```

(2) INFORMATION FOR SEQ ID NO:21:

(i) SEQUENCE CHARACTERISTICS:
        (A) LENGTH: 341 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:21:

```
CATTTATGGT TTCTCACCTG CCATTCTGAT AGTGGATTCT TGGGAATTCA GGCTTCATTT      60

GGATGCTCCG TTAAAGCTTG CTCCTTCATG TTCTTGCTTC TTCCTAGGAG CCAGCACCGC     120

TCTTTGACCT TGCCATGCTT GCCTTAGATA GTCCAGAGAG TGGCTGGACA GAGGAAGATG     180

GTCCCAAAGA AGGACTTGCT GAATACATTG TTGAGTTTCT GAAGAAGAAG GCTGAGATGC     240

TTGCAGACTA TTTCTCTTTG GAAATTGATG AGGTGTGACA GCCATTCTTA TACTTCTGTT     300

GTATTCTCCA AATAAAATTT CCAGCCGGGT GCATTGGCTC A                        341
```

(2) INFORMATION FOR SEQ ID NO:22:

(i) SEQUENCE CHARACTERISTICS:
        (A) LENGTH: 260 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:22:

```
CAGATAGGAG GCACAAGGCC TGGGAAAGGC ACTGGAGAAA TGGGATTTGT TTAAACTATG      60
ACAGCATTAT TTCTTGTTCC CTTGTCCTTT TTCCTGCAAG CAGGAAGGGA ACCTGATTGG     120
ATTACCCCTT CTGATTGACA ACTATGTGCC CCCTTTGGAG GGACTGCCTA TCTTCATTCT    180
TCGACTAGCC ACTGAGGTCA GTGATCAAGC AGATACTAAG CATTTCGGTA CATGCATGTG    240
TGCTGGAGGG AAAGGGCAAA                                                 260
```

(2) INFORMATION FOR SEQ ID NO:23:

(i) SEQUENCE CHARACTERISTICS:
        (A) LENGTH: 340 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:23:

```
CTATATCTTC CCAGCAATAT TCACAGTCCG TTTACAGTTT TAACGCCTAA AGTATCACAT     60
TTCGTTTTTT AGCTTTAAGT AGTCTGTGAT CTCCGTTTAG AATGAGAATG TTTAAATTCG    120
TACCTATTTT GAGGTATTGA ATTTCTTTGG ACCAGGTGAA TTGGGACGAA GAAAAGGAAT    180
GTTTTGAAAG CCTCAGTAAA GAATGCGCTA TGTTCTATTC CATCCGGAAG CAGTACATAT    240
CTGAGGAGTC GACCCTCTCA GGCCAGCAGG TACAGTGGTG ATGCACACTG GCACCCCAGG    300
ACTAGGACAG GACCTCATAC ATCTTAGGAG ATGAAACTTG                          340
```

(2) INFORMATION FOR SEQ ID NO:24:

(i) SEQUENCE CHARACTERISTICS:
        (A) LENGTH: 563 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:24:

```
AATCCTCTTG TGTTCAGGCC TGTGGATCCC TGAGAGGCTA GCCCACAAGA TCCACTTCAA     60
AAGCCCTAGA TAACACCAAG TCTTTCCAGA CCCAGTGCAC ATCCCATCAG CCAGGACACC   120
AGTGTATGTT GGGATGCAAA CAGGGAGGCT TATGACATCT AATGTGTTTT CCAGAGTGAA   180
GTGCCTGGCT CCATTCCAAA CTCCTGGAAG TGGACTGTGG AACACATTGT CTATAAAGCC   240
TTGCGCTCAC ACATTCTGCC TCCTAAACAT TTCACAGAAG ATGGAAATAT CCTGCAGCTT   300
GCTAACCTGC CTGATCTATA CAAAGTCTTT GAGAGGTGTT AAATATGGTT ATTTATGCAC   360
TGTGGGATGT GTTCTTCTTT CTCTGTATTC CGATACAAAG TGTTGTATCA AAGTGTGATA   420
TACAAAGTGT ACCAACATAA GTGTTGGTAG CACTTAAGAC TTATACTTGC CTTCTGATAG   480
TATTCCTTTA TACACAGTGG ATTGATTATA AATAAATAGA TGTGTCTTAA CATAATTTCT   540
TATTTAATTT TATTATGTAT ATA                                           563
```

(2) INFORMATION FOR SEQ ID NO:25:

(i) SEQUENCE CHARACTERISTICS:
        (A) LENGTH: 137 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:25:

CTTGGCTCTT CTGGCGCCAA AATGTCGTTC GTGGCAGGGG TTATTCGGCG GCTGGACGAG        60

ACAGTGGTGA ACCGCATCGC GGCGGGGGAA GTTATCCAGC GGCCAGCTAA TGCTATCAAA       120

GAGATGATTG AGAACTG                                                     137

(2) INFORMATION FOR SEQ ID NO:26:

(i) SEQUENCE CHARACTERISTICS:
            (A) LENGTH: 91 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:26:

TTTAGATGCA AAATCCACAA GTATTCAAGT GATTGTTAAA GAGGGAGGCC TGAAGTTGAT        60

TCAGATCCAA GACAATGGCA CCGGGATCAG G                                      91

(2) INFORMATION FOR SEQ ID NO:27:

(i) SEQUENCE CHARACTERISTICS:
            (A) LENGTH: 99 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:27:

AAAGAAGATC TGGATATTGT ATGTGAAAGG TTCACTACTA GTAAACTGCA GTCCTTTGAG        60

GATTTAGCCA GTATTTCTAC CTATGGCTTT CGAGGTGAG                              99

(2) INFORMATION FOR SEQ ID NO:28:

(i) SEQUENCE CHARACTERISTICS:
            (A) LENGTH: 74 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:28:

GCTTTGGCCA GCATAAGCCA TGTGGCTCAT GTTACTATTA CAACGAAAAC AGCTGATGGA        60

AAGTGTGCAT ACAG                                                         74

(2) INFORMATION FOR SEQ ID NO:29:

(i) SEQUENCE CHARACTERISTICS:
            (A) LENGTH: 73 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:29:

AGCAAGTTAC TCAGATGGAA AACTGAAAGC CCCTCCTAAA CCATGTGCTG GCAATCAAGG        60

GACCCAGATC ACG                                                          73

(2) INFORMATION FOR SEQ ID NO:30:

(i) SEQUENCE CHARACTERISTICS:
        (A) LENGTH: 92 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:30:

```
GTGGAGGACC TTTTTTACAA CATAGCCACG AGGAGAAAAG CTTTAAAAAA TCCAAGTGAA      60

GAATATGGGA AAATTTTGGA AGTTGTTGGC AG                                    92
```

(2) INFORMATION FOR SEQ ID NO:31:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:31:

```
GTATTCAGTA CACAATGCAG GCATTAGTTT CTCAGTTAAA AAA                        43
```

(2) INFORMATION FOR SEQ ID NO:32:

(i) SEQUENCE CHARACTERISTICS:
        (A) LENGTH: 89 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:32:

```
CAAGGAGAGA CAGTAGCTGA TGTTAGGACA CTACCCAATG CCTCAACCGT GGACAATATT      60

CGCTCCATCT TTGGAAATGC TGTTAGTCG                                        89
```

(2) INFORMATION FOR SEQ ID NO:33:

(i) SEQUENCE CHARACTERISTICS:
        (A) LENGTH: 113 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:33:

```
AGAACTGATA GAAATTGGAT GTGAGGATAA AACCCTAGCC TTCAAAATGA ATGGTTACAT      60

ATCCAATGCA AACTACTCAG TGAAGAAGTG CATCTTCTTA CTCTTCATCA ACC            113
```

(2) INFORMATION FOR SEQ ID NO:34:

(i) SEQUENCE CHARACTERISTICS:
        (A) LENGTH: 94 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:34:

ATCGTCTGGT AGAATCAACT TCCTTGAGAA AAGCCATAGA AACAGTGTAT GCAGCCTATT    60

TGCCCAAAAA CACACACCCA TTCCTGTACC TCAG    94

(2) INFORMATION FOR SEQ ID NO:35:

(i) SEQUENCE CHARACTERISTICS:
        (A) LENGTH: 154 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:35:

TTTAGAAATC AGTCCCCAGA ATGTGGATGT TAATGTGCAC CCCACAAAGC ATGAAGTTCA    60

CTTCCTGCAC GAGGAGAGCA TCCTGGAGCG GGTGCAGCAG CACATCGAGA GCAAGCTCCT   120

GGGCTCCAAT TCCTCCAGGA TGTACTTCAC CCAG   154

(2) INFORMATION FOR SEQ ID NO:36:

(i) SEQUENCE CHARACTERISTICS:
        (A) LENGTH: 371 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:36:

ACTTTGCTAC CAGGACTTGC TGGCCCCTCT GGGGAGATGG TTAAATCCAC AACAAGTCTG    60

ACCTCGTCTT CTACTTCTGG AAGTAGTGAT AAGGTCTATG CCCACCAGAT GGTTCGTACA   120

GATTCCCGGG AACAGAAGCT TGATGCATTT CTGCAGCCTC TGAGCAAACC CCTGTCCAGT   180

CAGCCCCAGG CCATTGTCAC AGAGGATAAG ACAGATATTT CTAGTGGCAG GGCTAGGCAG   240

CAAGATGAGG AGATGCTTGA ACTCCCAGCC CCTGCTGAAG TGGCTGCCAA AAATCAGAGC   300

TTGGAGGGGG ATACAACAAA GGGGACTTCA GAAATGTCAG AGAAGAGAGG ACCTACTTCC   360

AGCAACCCCA G   371

(2) INFORMATION FOR SEQ ID NO:37:

(i) SEQUENCE CHARACTERISTICS:
        (A) LENGTH: 149 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:37:

AAAGAGACAT CGGGAAGATT CTGATGTGGA AATGGTGGAA GATGATTCCC GAAAGGAAAT    60

GACTGCAGCT TGTACCCCCC GGAGAAGGAT CATTAACCTC ACTAGTGTTT TGAGTCTCCA   120

GGAAGAAATT AATGAGCAGG GACATGAGG   149

(2) INFORMATION FOR SEQ ID NO:38:

(i) SEQUENCE CHARACTERISTICS:
        (A) LENGTH: 109 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:38:

TTCTCCGGGA GATGTTGCAT AACCACTCCT TCGTGGGCTG TGTGAATCCT CAGTGGGCCT        60

TGGCACAGCA TCAAACCAAG TTATACCTTC TCAACACCAC CAAGCTTAG                   109

(2) INFORMATION FOR SEQ ID NO:39:

(i) SEQUENCE CHARACTERISTICS:
        (A) LENGTH: 64 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:39:

TGAAGAACTG TTCTACCAGA TACTCATTTA TGATTTTGCC AATTTTGGTG TTCTCAGGTT        60

ATCG                                                                   64

(2) INFORMATION FOR SEQ ID NO:40:

(i) SEQUENCE CHARACTERISTICS:
        (A) LENGTH: 165 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:40:

GAGCCAGCAC CGCTCTTTGA CCTTGCCATG CTTGCCTTAG ATAGTCCAGA GAGTGGCTGG        60

ACAGAGGAAG ATGGTCCCAA AGAAGGACTT GCTGAATACA TTGTTGAGTT TCTGAAGAAG       120

AAGGCTGAGA TGCTTGCAGA CTATTTCTCT TTGGAAATTG ATGAG                      165

(2) INFORMATION FOR SEQ ID NO:41:

(i) SEQUENCE CHARACTERISTICS:
        (A) LENGTH: 93 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:41:

GAAGGGAACC TGATTGGATT ACCCCTTCTG ATTGACAACT ATGTGCCCCC TTTGGAGGGA        60

CTGCCTATCT TCATTCTTCG ACTAGCCACT GAG                                    93

(2) INFORMATION FOR SEQ ID NO:42:

(i) SEQUENCE CHARACTERISTICS:
        (A) LENGTH: 114 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:42:

GTGAATTGGG ACGAAGAAAA GGAATGTTTT GAAAGCCTCA GTAAAGAATG CGCTATGTTC        60

TATTCCATCC GGAAGCAGTA CATATCTGAG GAGTCGACCC TCTCAGGCCA GCAG            114

(2) INFORMATION FOR SEQ ID NO:43:

(i) SEQUENCE CHARACTERISTICS:
        (A) LENGTH: 360 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:43:

AGTGAAGTGC CTGGCTCCAT TCCAAACTCC TGGAAGTGGA CTGTGGAACA CATTGTCTAT    60

AAAGCCTTGC GCTCACACAT TCTGCCTCCT AAACATTTCA CAGAAGATGG AAATATCCTG    120

CAGCTTGCTA ACCTGCCTGA TCTATACAAA GTCTTTGAGA GGTGTTAAAT ATGGTTATTT    180

ATGCACTGTG GGATGTGTTC TTCTTTCTCT GTATTCCGAT ACAAAGTGTT GTATCAAAGT    240

GTGATATACA AAGTGTACCA ACATAAGTGT TGGTAGCACT TAAGACTTAT ACTTGCCTTC    300

TGATAGTATT CCTTTATACA CAGTGGATTG ATTATAAATA AATAGATGTG TCTTAACATA    360

(2) INFORMATION FOR SEQ ID NO:44:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ix) FEATURE:
        (A) NAME/KEY: misc_feature
        (B) LOCATION: 1
        (D) OTHER INFORMATION: /note= "primers directed to genomic
            intron DNA"

(xi) SEQUENCE DESCRIPTION: SEQ ID NO:44:

AGGCACTGAG GTGATTGGC                                                 19

(2) INFORMATION FOR SEQ ID NO:45:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ix) FEATURE:
        (A) NAME/KEY: misc_feature
        (B) LOCATION: 1
        (D) OTHER INFORMATION: /note= "primers directed to genomic
            intron DNA"

(xi) SEQUENCE DESCRIPTION: SEQ ID NO:45:

TCGTAGCCCT TAAGTGAGC                                                 19

(2) INFORMATION FOR SEQ ID NO:46:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ix) FEATURE:
        (A) NAME/KEY: misc_feature
        (B) LOCATION: 1
        (D) OTHER INFORMATION: /note= "primers directed to genomic
            intron DNA"

(xi) SEQUENCE DESCRIPTION: SEQ ID NO:46:

AATATGTACA TTAGAGTAGT TG                                             22

(2) INFORMATION FOR SEQ ID NO:47:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ix) FEATURE:
        (A) NAME/KEY: misc_feature
        (B) LOCATION: 1
        (D) OTHER INFORMATION: /note= "primers directed to genomic
            intron DNA"

(xi) SEQUENCE DESCRIPTION: SEQ ID NO:47:

CAGAGAAAGG TCCTGACTC                                          19

(2) INFORMATION FOR SEQ ID NO:48:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ix) FEATURE:
        (A) NAME/KEY: misc_feature
        (B) LOCATION: 1
        (D) OTHER INFORMATION: /note= "primers directed to genomic
            intron DNA"

(xi) SEQUENCE DESCRIPTION: SEQ ID NO:48:

AGAGATTTGG AAAATGAGTA AC                                    22

(2) INFORMATION FOR SEQ ID NO:49:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ix) FEATURE:
        (A) NAME/KEY: misc_feature
        (B) LOCATION: 1
        (D) OTHER INFORMATION: /note= "primers directed to genomic
            intron DNA"

(xi) SEQUENCE DESCRIPTION: SEQ ID NO:49:

ACAATGTCAT CACAGGAGG                                          19

(2) INFORMATION FOR SEQ ID NO:50:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ix) FEATURE:
        (A) NAME/KEY: misc_feature
        (B) LOCATION: 1
        (D) OTHER INFORMATION: /note= "primers directed to genomic
            intron DNA"

(xi) SEQUENCE DESCRIPTION: SEQ ID NO:50:

AACCTTTCCC TTTGGTGAGG                                        20

(2) INFORMATION FOR SEQ ID NO:51:

```
    (i) SEQUENCE CHARACTERISTICS:
        (A) LENGTH: 20 base pairs
        (B) TYPE: nucleic acid
        (C) STRANDEDNESS: single
        (D) TOPOLOGY: linear (ix) FEATURE:
        (A) NAME/KEY: misc_feature
        (B) LOCATION: 1
        (D) OTHER INFORMATION: /note= "primers directed to genomic
             intron DNA"

(xi) SEQUENCE DESCRIPTION: SEQ ID NO:51:

GATTACTCTG AGACCTAGGC                                                      20

(2) INFORMATION FOR SEQ ID NO:52:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ix) FEATURE:
        (A) NAME/KEY: misc_feature
        (B) LOCATION: 1
        (D) OTHER INFORMATION: /note= "primers directed to genomic
             intron DNA"

(xi) SEQUENCE DESCRIPTION: SEQ ID NO:52:

GATTTTCTCT TTTCCCCTTG GG                                                   22

(2) INFORMATION FOR SEQ ID NO:53:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ix) FEATURE:
        (A) NAME/KEY: misc_feature
        (B) LOCATION: 1
        (D) OTHER INFORMATION: /note= "primers directed to genomic
             intron DNA"

(xi) SEQUENCE DESCRIPTION: SEQ ID NO:53:

CAAACAAAGC TTCAACAATT TAC                                                  23

(2) INFORMATION FOR SEQ ID NO:54:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ix) FEATURE:
        (A) NAME/KEY: misc_feature
        (B) LOCATION: 1
        (D) OTHER INFORMATION: /note= "primers directed to genomic
             intron DNA"

(xi) SEQUENCE DESCRIPTION: SEQ ID NO:54:

GGGTTTTATT TTCAAGTACT TCTATG                                               26

(2) INFORMATION FOR SEQ ID NO:55:

(i) SEQUENCE CHARACTERISTICS:
        (A) LENGTH: 26 base pairs
```

(B) TYPE: nucleic acid
            (C) STRANDEDNESS: single
            (D) TOPOLOGY: linear (ix) FEATURE:
            (A) NAME/KEY: misc_feature
            (B) LOCATION: 1
            (D) OTHER INFORMATION: /note= "primers directed to genomic
                intron DNA"

(xi) SEQUENCE DESCRIPTION: SEQ ID NO:55:

GCTCAGCAAC TGTTCAATGT ATGAGC                                            26

(2) INFORMATION FOR SEQ ID NO:56:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ix) FEATURE:
            (A) NAME/KEY: misc_feature
            (B) LOCATION: 1
            (D) OTHER INFORMATION: /note= "primers directed to genomic
                intron DNA"

(xi) SEQUENCE DESCRIPTION: SEQ ID NO:56:

CTAGTGTGTG TTTTTGGC                                                     18

(2) INFORMATION FOR SEQ ID NO:57:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ix) FEATURE:
            (A) NAME/KEY: misc_feature
            (B) LOCATION: 1
            (D) OTHER INFORMATION: /note= "primers directed to genomic
                intron DNA"

(xi) SEQUENCE DESCRIPTION: SEQ ID NO:57:

CATAACCTTA TCTCCACC                                                     18

(2) INFORMATION FOR SEQ ID NO:58:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ix) FEATURE:
            (A) NAME/KEY: misc_feature
            (B) LOCATION: 1
            (D) OTHER INFORMATION: /note= "primers directed to genomic
                intron DNA"

(xi) SEQUENCE DESCRIPTION: SEQ ID NO:58:

CTCAGCCATG AGACAATAAA TCC                                               23

(2) INFORMATION FOR SEQ ID NO:59:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ix) FEATURE:
              (A) NAME/KEY: misc_feature
              (B) LOCATION: 1
              (D) OTHER INFORMATION: /note= "primers directed to genomic
                  DNA"

(xi) SEQUENCE DESCRIPTION: SEQ ID NO:59:

GGTTCCCAAA TAATGTGATG G                                          21

(2) INFORMATION FOR SEQ ID NO:60:

(i) SEQUENCE CHARACTERISTICS:
              (A) LENGTH: 18 base pairs
              (B) TYPE: nucleic acid
              (C) STRANDEDNESS: single
              (D) TOPOLOGY: linear (ix) FEATURE:
              (A) NAME/KEY: misc_feature
              (B) LOCATION: 1
              (D) OTHER INFORMATION: /note= "primers directed to genomic
                  intron DNA"

(xi) SEQUENCE DESCRIPTION: SEQ ID NO:60:

CAAAAGCTTC AGAATCTC                                              18

(2) INFORMATION FOR SEQ ID NO:61:

(i) SEQUENCE CHARACTERISTICS:
              (A) LENGTH: 23 base pairs
              (B) TYPE: nucleic acid
              (C) STRANDEDNESS: single
              (D) TOPOLOGY: linear (ix) FEATURE:
              (A) NAME/KEY: misc_feature
              (B) LOCATION: 1
              (D) OTHER INFORMATION: /note= "primers directed to genomic
                  intron DNA"

(xi) SEQUENCE DESCRIPTION: SEQ ID NO:61:

CTGTGGGTGT TTCCTGTGAG TGG                                        23

(2) INFORMATION FOR SEQ ID NO:62:

(i) SEQUENCE CHARACTERISTICS:
              (A) LENGTH: 24 base pairs
              (B) TYPE: nucleic acid
              (C) STRANDEDNESS: single
              (D) TOPOLOGY: linear (ix) FEATURE:
              (A) NAME/KEY: misc_feature
              (B) LOCATION: 1
              (D) OTHER INFORMATION: /note= "primers directed to genomic
                  intron DNA"

(xi) SEQUENCE DESCRIPTION: SEQ ID NO:62:

CATGACTTTG TGTGAATGTA CACC                                       24

(2) INFORMATION FOR SEQ ID NO:63:

(i) SEQUENCE CHARACTERISTICS:
              (A) LENGTH: 24 base pairs
              (B) TYPE: nucleic acid
              (C) STRANDEDNESS: single
              (D) TOPOLOGY: linear (ix) FEATURE:
              (A) NAME/KEY: misc_feature (B) LOCATION: 1
            (D) OTHER INFORMATION: /note= "primers directed to genomic
                intron DNA"

(xi) SEQUENCE DESCRIPTION: SEQ ID NO:63:

GAGGAGAGCC TGATAGAACA TCTG                                              24

(2) INFORMATION FOR SEQ ID NO:64:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ix) FEATURE:
        (A) NAME/KEY: misc_feature
        (B) LOCATION: 1
        (D) OTHER INFORMATION: /note= "primers directed to genomic
            intron DNA"

(xi) SEQUENCE DESCRIPTION: SEQ ID NO:64:

GGGCTTTTTC TCCCCCTCCC                                                   20

(2) INFORMATION FOR SEQ ID NO:65:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ix) FEATURE:
        (A) NAME/KEY: misc_feature
        (B) LOCATION: 1
        (D) OTHER INFORMATION: /note= "primers directed to genomic
            intron DNA"

(xi) SEQUENCE DESCRIPTION: SEQ ID NO:65:

AAAATCTGGG CTCTCACG                                                     18

(2) INFORMATION FOR SEQ ID NO:66:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ix) FEATURE:
        (A) NAME/KEY: misc_feature
        (B) LOCATION: 1
        (D) OTHER INFORMATION: /note= "primers directed to genomic
            intron DNA"

(xi) SEQUENCE DESCRIPTION: SEQ ID NO:66:

AATTATACCT CATACTAGC                                                    19

(2) INFORMATION FOR SEQ ID NO:67:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ix) FEATURE:
        (A) NAME/KEY: misc_feature
        (B) LOCATION: 1
        (D) OTHER INFORMATION: /note= "primers directed to genomic
            intron DNA"

(xi) SEQUENCE DESCRIPTION: SEQ ID NO:67:

GTTTTATTAC AGAATAAAGG AGG                                                23

(2) INFORMATION FOR SEQ ID NO:68:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ix) FEATURE:
        (A) NAME/KEY: misc_feature
        (B) LOCATION: 1
        (D) OTHER INFORMATION: /note= "primers directed to genomic
            intron DNA"

(xi) SEQUENCE DESCRIPTION: SEQ ID NO:68:

AAGCCAAAGT TAGAAGGCA                                                     19

(2) INFORMATION FOR SEQ ID NO:69:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ix) FEATURE:
        (A) NAME/KEY: misc_feature
        (B) LOCATION: 1
        (D) OTHER INFORMATION: /note= "primers directed to genomic
            intron DNA"

(xi) SEQUENCE DESCRIPTION: SEQ ID NO:69:

TGCAACCCAC AAAATTTGGC                                                    20

(2) INFORMATION FOR SEQ ID NO:70:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ix) FEATURE:
        (A) NAME/KEY: misc_feature
        (B) LOCATION: 1
        (D) OTHER INFORMATION: /note= "primers directed to genomic
            intron DNA"

(xi) SEQUENCE DESCRIPTION: SEQ ID NO:70:

CTTTCTCCAT TTCCAAAACC                                                    20

(2) INFORMATION FOR SEQ ID NO:71:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ix) FEATURE:
        (A) NAME/KEY: misc_feature
        (B) LOCATION: 1
        (D) OTHER INFORMATION: /note= "primers directed to genomic
            intron DNA"

(xi) SEQUENCE DESCRIPTION: SEQ ID NO:71:

```
TGGTGTCTCT AGTTCTGG                                                    18

(2) INFORMATION FOR SEQ ID NO:72:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ix) FEATURE:
        (A) NAME/KEY: misc_feature
        (B) LOCATION: 1
        (D) OTHER INFORMATION: /note= "primers directed to genomic
             intron DNA"

(xi) SEQUENCE DESCRIPTION: SEQ ID NO:72:

CATTGTTGTA GTAGCTCTGC                                                  20

(2) INFORMATION FOR SEQ ID NO:73:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ix) FEATURE:
        (A) NAME/KEY: misc_feature
        (B) LOCATION: 1
        (D) OTHER INFORMATION: /note= "primers directed to genomic
             intron DNA"

(xi) SEQUENCE DESCRIPTION: SEQ ID NO:73:

CCCATTTGTC CCAACTGG                                                    18

(2) INFORMATION FOR SEQ ID NO:74:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ix) FEATURE:
        (A) NAME/KEY: misc_feature
        (B) LOCATION: 1
        (D) OTHER INFORMATION: /note= "primers directed to genomic
             intron DNA"

(xi) SEQUENCE DESCRIPTION: SEQ ID NO:74:

CGGTCAGTTG AAATGTCAG                                                   19

(2) INFORMATION FOR SEQ ID NO:75:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ix) FEATURE:
        (A) NAME/KEY: misc_feature
        (B) LOCATION: 1
        (D) OTHER INFORMATION: /note= "primers directed to genomic
             intron DNA"

(xi) SEQUENCE DESCRIPTION: SEQ ID NO:75:

CATTTGGATG CTCCGTTAAA GC                                               22
```

(2) INFORMATION FOR SEQ ID NO:76:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ix) FEATURE:
        (A) NAME/KEY: misc_feature
        (B) LOCATION: 1
        (D) OTHER INFORMATION: /note= "primers directed to genomic
            intron DNA"

(xi) SEQUENCE DESCRIPTION: SEQ ID NO:76:

CACCCGGCTG GAAATTTTAT TTG                                                        23

(2) INFORMATION FOR SEQ ID NO:77:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ix) FEATURE:
        (A) NAME/KEY: misc_feature
        (B) LOCATION: 1
        (D) OTHER INFORMATION: /note= "primers directed to genomic
            intron DNA"

(xi) SEQUENCE DESCRIPTION: SEQ ID NO:77:

GGAAAGGCAC TGGAGAAATG GG                                                        22

(2) INFORMATION FOR SEQ ID NO:78:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ix) FEATURE:
        (A) NAME/KEY: misc_feature
        (B) LOCATION: 1
        (D) OTHER INFORMATION: /note= "primers directed to genomic
            intron DNA"

(xi) SEQUENCE DESCRIPTION: SEQ ID NO:78:

CCCTCCAGCA CACATGCATG TACCG                                                 25

(2) INFORMATION FOR SEQ ID NO:79:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ix) FEATURE:
        (A) NAME/KEY: misc_feature
        (B) LOCATION: 1
        (D) OTHER INFORMATION: /note= "primers directed to genomic
            intron DNA"

(xi) SEQUENCE DESCRIPTION: SEQ ID NO:79:

TAAGTAGTCT GTGATCTCCG                                                          20

(2) INFORMATION FOR SEQ ID NO:80:

(i) SEQUENCE CHARACTERISTICS:

(A) LENGTH: 18 base pairs
          (B) TYPE: nucleic acid
          (C) STRANDEDNESS: single
          (D) TOPOLOGY: linear (ix) FEATURE:
          (A) NAME/KEY: misc_feature
          (B) LOCATION: 1
          (D) OTHER INFORMATION: /note= "primers directed to genomic
              intron DNA"

(xi) SEQUENCE DESCRIPTION: SEQ ID NO:80:

ATGTATGAGG TCCTGTCC                                                      18

(2) INFORMATION FOR SEQ ID NO:81:

(i) SEQUENCE CHARACTERISTICS:
          (A) LENGTH: 18 base pairs
          (B) TYPE: nucleic acid
          (C) STRANDEDNESS: single
          (D) TOPOLOGY: linear (ix) FEATURE:
          (A) NAME/KEY: misc_feature
          (B) LOCATION: 1
          (D) OTHER INFORMATION: /note= "primers directed to genomic
              intron DNA"

(xi) SEQUENCE DESCRIPTION: SEQ ID NO:81:

GACACCAGTG TATGTTGG                                                      18

(2) INFORMATION FOR SEQ ID NO:82:

(i) SEQUENCE CHARACTERISTICS:
          (A) LENGTH: 20 base pairs
          (B) TYPE: nucleic acid
          (C) STRANDEDNESS: single
          (D) TOPOLOGY: linear (ix) FEATURE:
          (A) NAME/KEY: misc_feature
          (B) LOCATION: 1
          (D) OTHER INFORMATION: /note= "primers directed to genomic
              intron DNA"

(xi) SEQUENCE DESCRIPTION: SEQ ID NO:82:

GAGAAAGAAG AACACATCCC                                                    20

(2) INFORMATION FOR SEQ ID NO:83:

(i) SEQUENCE CHARACTERISTICS:
          (A) LENGTH: 38 base pairs
          (B) TYPE: nucleic acid
          (C) STRANDEDNESS: single
          (D) TOPOLOGY: linear (ix) FEATURE:
          (A) NAME/KEY: misc_feature
          (B) LOCATION: 1
          (D) OTHER INFORMATION: /note= "primers directed to genomic
              intron DNA"

(xi) SEQUENCE DESCRIPTION: SEQ ID NO:83:

TGTAAAACGA CGGCCAGTCA CTGAGGTGAT TGGCTGAA                                38

(2) INFORMATION FOR SEQ ID NO:84:

(i) SEQUENCE CHARACTERISTICS:
          (A) LENGTH: 19 base pairs
          (B) TYPE: nucleic acid
          (C) STRANDEDNESS: single

```
            (D) TOPOLOGY: linear (ix) FEATURE:
            (A) NAME/KEY: misc_feature
            (B) LOCATION: 1
            (D) OTHER INFORMATION: /note= "primers directed to genomic
                intron DNA"

(xi) SEQUENCE DESCRIPTION: SEQ ID NO:84:

TAGCCCTTAA GTGAGCCCG                                                    19

(2) INFORMATION FOR SEQ ID NO:85:

(i) SEQUENCE CHARACTERISTICS:
            (A) LENGTH: 38 base pairs
            (B) TYPE: nucleic acid
            (C) STRANDEDNESS: single
            (D) TOPOLOGY: linear (ix) FEATURE:
            (A) NAME/KEY: misc_feature
            (B) LOCATION: 1
            (D) OTHER INFORMATION: /note= "primers directed to genomic
                intron DNA"

(xi) SEQUENCE DESCRIPTION: SEQ ID NO:85:

TGTAAAACGA CGGCCAGTTA CATTAGAGTA GTTGCAGA                                38

(2) INFORMATION FOR SEQ ID NO:86:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ix) FEATURE:
            (A) NAME/KEY: misc_feature
            (B) LOCATION: 1
            (D) OTHER INFORMATION: /note= "primers directed to genomic
                intron DNA"

(xi) SEQUENCE DESCRIPTION: SEQ ID NO:86:

AGGTCCTGAC TCTTCCATG                                                    19

(2) INFORMATION FOR SEQ ID NO:87:

(i) SEQUENCE CHARACTERISTICS:
            (A) LENGTH: 40 base pairs
            (B) TYPE: nucleic acid
            (C) STRANDEDNESS: single
            (D) TOPOLOGY: linear (ix) FEATURE:
            (A) NAME/KEY: misc_feature
            (B) LOCATION: 1
            (D) OTHER INFORMATION: /note= "primers directed to genomic
                intron DNA"

(xi) SEQUENCE DESCRIPTION: SEQ ID NO:87:

TGTAAAACGA CGGCCAGTTT GGAAAATGAG TAACATGATT                              40

(2) INFORMATION FOR SEQ ID NO:88:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ix) FEATURE:
```

(A) NAME/KEY: misc_feature
        (B) LOCATION: 1
        (D) OTHER INFORMATION: /note= "primers directed to genomic
            intron DNA"

(xi) SEQUENCE DESCRIPTION: SEQ ID NO:88:

TGTCATCACA GGAGGATAT                                                       19

(2) INFORMATION FOR SEQ ID NO:89:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ix) FEATURE:
        (A) NAME/KEY: misc_feature
        (B) LOCATION: 1
        (D) OTHER INFORMATION: /note= "primers directed to genomic
            intron DNA"

(xi) SEQUENCE DESCRIPTION: SEQ ID NO:89:

TGTAAAACGA CGGCCAGTCT TTCCCTTTGG TGAGGTGA                                   38

(2) INFORMATION FOR SEQ ID NO:90:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ix) FEATURE:
        (A) NAME/KEY: misc_feature
        (B) LOCATION: 1
        (D) OTHER INFORMATION: /note= "primers directed to genomic
            intron DNA"

(xi) SEQUENCE DESCRIPTION: SEQ ID NO:90:

TACTCTGAGA CCTAGGCCCA                                                      20

(2) INFORMATION FOR SEQ ID NO:91:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ix) FEATURE:
        (A) NAME/KEY: misc_feature
        (B) LOCATION: 1
        (D) OTHER INFORMATION: /note= "primers directed to genomic
            intron DNA"

(xi) SEQUENCE DESCRIPTION: SEQ ID NO:91:

TGTAAAACGA CGGCCAGTTC TCTTTTCCCC TTGGGATTAG                                 40

(2) INFORMATION FOR SEQ ID NO:92:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ix) FEATURE:
        (A) NAME/KEY: misc_feature
        (B) LOCATION: 1
        (D) OTHER INFORMATION: /note= "primers directed to genomic intron DNA"

(xi) SEQUENCE DESCRIPTION: SEQ ID NO:92:

ACAAAGCTTC AACAATTTAC TCT                                                    23

(2) INFORMATION FOR SEQ ID NO:93:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (ix) FEATURE:
        (A) NAME/KEY: misc_feature
        (B) LOCATION: 1
        (D) OTHER INFORMATION: /note= "primers directed to genomic
            intron DNA"

(xi) SEQUENCE DESCRIPTION: SEQ ID NO:93:

TGTAAAACGA CGGCCAGTGT TTTATTTTCA AGTACTTCTA TGAATT                           46

(2) INFORMATION FOR SEQ ID NO:94:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ix) FEATURE:
        (A) NAME/KEY: misc_feature
        (B) LOCATION: 1
        (D) OTHER INFORMATION: /note= "primers directed to genomic
            intron DNA"

(xi) SEQUENCE DESCRIPTION: SEQ ID NO:94:

CAGCAACTGT TCAATGTATG AGCACT                                                 26

(2) INFORMATION FOR SEQ ID NO:95:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ix) FEATURE:
        (A) NAME/KEY: misc_feature
        (B) LOCATION: 1
        (D) OTHER INFORMATION: /note= "primers directed to genomic
            intron DNA"

(xi) SEQUENCE DESCRIPTION: SEQ ID NO:95:

TGTAAAACGA CGGCCAGTGT GTGTGTTTTT GGCAAC                                      36

(2) INFORMATION FOR SEQ ID NO:96:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ix) FEATURE:
        (A) NAME/KEY: misc_feature
        (B) LOCATION: 1
        (D) OTHER INFORMATION: /note= "primers directed to genomic
            intron DNA"

(xi) SEQUENCE DESCRIPTION: SEQ ID NO:96:

AACCTTATCT CCACCAGC                                                    18

(2) INFORMATION FOR SEQ ID NO:97:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ix) FEATURE:
        (A) NAME/KEY: misc_feature
        (B) LOCATION: 1
        (D) OTHER INFORMATION: /note= "primers directed to genomic
            intron DNA"

(xi) SEQUENCE DESCRIPTION: SEQ ID NO:97:

TGTAAAACGA CGGCCAGTAG CCATGAGACA ATAAATCCTT G                          41

(2) INFORMATION FOR SEQ ID NO:98:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ix) FEATURE:
        (A) NAME/KEY: misc_feature
        (B) LOCATION: 1
        (D) OTHER INFORMATION: /note= "primers directed to genomic
            intron DNA"

(xi) SEQUENCE DESCRIPTION: SEQ ID NO:98:

TCCCAAATAA TGTGATGGAA TG                                               22

(2) INFORMATION FOR SEQ ID NO:99:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ix) FEATURE:
        (A) NAME/KEY: misc_feature
        (B) LOCATION: 1
        (D) OTHER INFORMATION: /note= "primers directed to genomic
            intron DNA"

(xi) SEQUENCE DESCRIPTION: SEQ ID NO:99:

TGTAAAACGA CGGCCAGTAA GCTTCAGAAT CTCTTTT                               37

(2) INFORMATION FOR SEQ ID NO:100:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ix) FEATURE:
        (A) NAME/KEY: misc_feature
        (B) LOCATION: 1
        (D) OTHER INFORMATION: /note= "primers directed to genomic
            intron DNA"

(xi) SEQUENCE DESCRIPTION: SEQ ID NO:100:

TGGGTGTTTC CTGTGAGTGG ATT                                              23

(2) INFORMATION FOR SEQ ID NO:101:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ix) FEATURE:
        (A) NAME/KEY: misc_feature
        (B) LOCATION: 1
        (D) OTHER INFORMATION: /note= "primers directed to genomic
            intron DNA"

(xi) SEQUENCE DESCRIPTION: SEQ ID NO:101:

TGTAAAACGA CGGCCAGTAC TTTGTGTGAA TGTACACCTG TG                              42

(2) INFORMATION FOR SEQ ID NO:102:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ix) FEATURE:
        (A) NAME/KEY: misc_feature
        (B) LOCATION: 1
        (D) OTHER INFORMATION: /note= "primers directed to genomic
            intron DNA"

(xi) SEQUENCE DESCRIPTION: SEQ ID NO:102:

GAGAGCCTGA TAGAACATCT GTTG                                                 24

(2) INFORMATION FOR SEQ ID NO:103:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ix) FEATURE:
        (A) NAME/KEY: misc_feature
        (B) LOCATION: 1
        (D) OTHER INFORMATION: /note= "primers directed to genomic
            intron DNA"

(xi) SEQUENCE DESCRIPTION: SEQ ID NO:103:

TGTAAAACGA CGGCCAGTCT TTTTCTCCCC CTCCCACTA                                  39

(2) INFORMATION FOR SEQ ID NO:104:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ix) FEATURE:
        (A) NAME/KEY: misc_feature
        (B) LOCATION: 1
        (D) OTHER INFORMATION: /note= "primers directed to genomic
            intron DNA"

(xi) SEQUENCE DESCRIPTION: SEQ ID NO:104:

TCTGGGCTCT CACGTCT                                                         17

(2) INFORMATION FOR SEQ ID NO:105:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ix) FEATURE:
        (A) NAME/KEY: misc_feature
        (B) LOCATION: 1
        (D) OTHER INFORMATION: /note= "primers directed to genomic
            intron DNA"

(xi) SEQUENCE DESCRIPTION: SEQ ID NO:105:

CTTATTCTGA GTCTCTCC                                                    18

(2) INFORMATION FOR SEQ ID NO:106:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ix) FEATURE:
        (A) NAME/KEY: misc_feature
        (B) LOCATION: 1
        (D) OTHER INFORMATION: /note= "primers directed to genomic
            intron DNA"

(xi) SEQUENCE DESCRIPTION: SEQ ID NO:106:

TGTAAAACGA CGGCCAGTGT TTGCTCAGAG GCTGC                                  35

(2) INFORMATION FOR SEQ ID NO:107:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ix) FEATURE:
        (A) NAME/KEY: misc_feature
        (B) LOCATION: 1
        (D) OTHER INFORMATION: /note= "primers directed to genomic
            intron DNA"

(xi) SEQUENCE DESCRIPTION: SEQ ID NO:107:

GATGGTTCGT ACAGATTCCC G                                                 21

(2) INFORMATION FOR SEQ ID NO:108:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ix) FEATURE:
        (A) NAME/KEY: misc_feature
        (B) LOCATION: 1
        (D) OTHER INFORMATION: /note= "primers directed to genomic
            intron DNA"

(xi) SEQUENCE DESCRIPTION: SEQ ID NO:108:

TGTAAAACGA CGGCCAGTTT ATTACAGAAT AAAGGAGGTA G                           41

(2) INFORMATION FOR SEQ ID NO:109:

(i) SEQUENCE CHARACTERISTICS:
        (A) LENGTH: 39 base pairs
        (B) TYPE: nucleic acid (C) STRANDEDNESS: single
        (D) TOPOLOGY: linear (ix) FEATURE:
        (A) NAME/KEY: misc_feature
        (B) LOCATION: 1
        (D) OTHER INFORMATION: /note= "primers directed to genomic
            intron DNA"

(xi) SEQUENCE DESCRIPTION: SEQ ID NO:109:

TGTAAAACGA CGGCCAGTAA CCCACAAAAT TTGGCTAAG                              39

(2) INFORMATION FOR SEQ ID NO:110:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ix) FEATURE:
        (A) NAME/KEY: misc_feature
        (B) LOCATION: 1
        (D) OTHER INFORMATION: /note= "primers directed to genomic
            intron DNA"

(xi) SEQUENCE DESCRIPTION: SEQ ID NO:110:

TCTCCATTTC CAAAACCTTG                                                  20

(2) INFORMATION FOR SEQ ID NO:111:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ix) FEATURE:
        (A) NAME/KEY: misc_feature
        (B) LOCATION: 1
        (D) OTHER INFORMATION: /note= "primers directed to genomic
            intron DNA"

(xi) SEQUENCE DESCRIPTION: SEQ ID NO:111:

TGTCTCTAGT TCTGGTGC                                                    18

(2) INFORMATION FOR SEQ ID NO:112:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ix) FEATURE:
        (A) NAME/KEY: misc_feature
        (B) LOCATION: 1
        (D) OTHER INFORMATION: /note= "primers directed to genomic
            intron DNA"

(xi) SEQUENCE DESCRIPTION: SEQ ID NO:112:

TGTAAAACGA CGGCCAGTTG TTGTAGTAGC TCTGCTTG                               38

(2) INFORMATION FOR SEQ ID NO:113:

(i) SEQUENCE CHARACTERISTICS:
        (A) LENGTH: 20 base pairs
        (B) TYPE: nucleic acid
        (C) STRANDEDNESS: single
        (D) TOPOLOGY: linear

```
        (ix) FEATURE:
              (A) NAME/KEY: misc_feature
              (B) LOCATION: 1
              (D) OTHER INFORMATION: /note= "primers directed to genomic
                  intron DNA"

(xi) SEQUENCE DESCRIPTION: SEQ ID NO:113:

ATTTGTCCCA ACTGGTTGTA                                              20

(2) INFORMATION FOR SEQ ID NO:114:

(i) SEQUENCE CHARACTERISTICS:
              (A) LENGTH: 39 base pairs
              (B) TYPE: nucleic acid
              (C) STRANDEDNESS: single
              (D) TOPOLOGY: linear (ix) FEATURE:
              (A) NAME/KEY: misc_feature
              (B) LOCATION: 1
              (D) OTHER INFORMATION: /note= "primers directed to genomic
                  intron DNA"

(xi) SEQUENCE DESCRIPTION: SEQ ID NO:114:

TGTAAAACGA CGGCCAGTTC AGTTGAAATG TCAGAAGTG                          39

(2) INFORMATION FOR SEQ ID NO:115:

(i) SEQUENCE CHARACTERISTICS:
              (A) LENGTH: 18 base pairs
              (B) TYPE: nucleic acid
              (C) STRANDEDNESS: single
              (D) TOPOLOGY: linear (ix) FEATURE:
              (A) NAME/KEY: misc_feature
              (B) LOCATION: 1
              (D) OTHER INFORMATION: /note= "primers directed to genomic
                  intron DNA"

(xi) SEQUENCE DESCRIPTION: SEQ ID NO:115:

TGTAAAACGA CGGCCAGT                                                18

(2) INFORMATION FOR SEQ ID NO:116:

(i) SEQUENCE CHARACTERISTICS:
              (A) LENGTH: 23 base pairs
              (B) TYPE: nucleic acid
              (C) STRANDEDNESS: single
              (D) TOPOLOGY: linear (ix) FEATURE:
              (A) NAME/KEY: misc_feature
              (B) LOCATION: 1
              (D) OTHER INFORMATION: /note= "primers directed to genomic
                  intron DNA"

(xi) SEQUENCE DESCRIPTION: SEQ ID NO:116:

CCGGCTGGAA ATTTTATTTG GAG                                          23

(2) INFORMATION FOR SEQ ID NO:117:

(i) SEQUENCE CHARACTERISTICS:
              (A) LENGTH: 41 base pairs
              (B) TYPE: nucleic acid
              (C) STRANDEDNESS: single
              (D) TOPOLOGY: linear (ix) FEATURE:
              (A) NAME/KEY: misc_feature
              (B) LOCATION: 1
```

(D) OTHER INFORMATION: /note= "primers directed to genomic intron DNA"

(xi) SEQUENCE DESCRIPTION: SEQ ID NO:117:

TGTAAAACGA CGGCCAGTAG GCACTGGAGA AATGGGATTT G    41

(2) INFORMATION FOR SEQ ID NO:118:

(i) SEQUENCE CHARACTERISTICS:
      (A) LENGTH: 26 base pairs
      (B) TYPE: nucleic acid
      (C) STRANDEDNESS: single
      (D) TOPOLOGY: linear (ix) FEATURE:
      (A) NAME/KEY: misc_feature
      (B) LOCATION: 1
      (D) OTHER INFORMATION: /note= "primers directed to genomic intron DNA"

(xi) SEQUENCE DESCRIPTION: SEQ ID NO:118:

TCCAGCACAC ATGCATGTAC CGAAAT    26

(2) INFORMATION FOR SEQ ID NO:119:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ix) FEATURE:
      (A) NAME/KEY: misc_feature
      (B) LOCATION: 1
      (D) OTHER INFORMATION: /note= "primer directed to genomic intron DNA"

(xi) SEQUENCE DESCRIPTION: SEQ ID NO:119:

GTAGTCTGTG ATCTCCGTTT    20

(2) INFORMATION FOR SEQ ID NO:120:

(i) SEQUENCE CHARACTERISTICS:
      (A) LENGTH: 36 base pairs
      (B) TYPE: nucleic acid
      (C) STRANDEDNESS: single
      (D) TOPOLOGY: linear (ix) FEATURE:
      (A) NAME/KEY: misc_feature
      (B) LOCATION: 1
      (D) OTHER INFORMATION: /note= "primers directed to genomic intron DNA"

(xi) SEQUENCE DESCRIPTION: SEQ ID NO:120:

TGTAAAACGA CGGCCAGTTA TGAGGTCCTG TCCTAG    36

(2) INFORMATION FOR SEQ ID NO:121:

(i) SEQUENCE CHARACTERISTICS:
      (A) LENGTH: 19 base pairs
      (B) TYPE: nucleic acid
      (C) STRANDEDNESS: single
      (D) TOPOLOGY: linear (ix) FEATURE:
      (A) NAME/KEY: misc_feature
      (B) LOCATION: 1
      (D) OTHER INFORMATION: /note= "primers directed to genomic intron DNA"

(xi) SEQUENCE DESCRIPTION: SEQ ID NO:121:

ACCAGTGTAT GTTGGGATG                                                                              19

(2) INFORMATION FOR SEQ ID NO:122:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ix) FEATURE:
        (A) NAME/KEY: misc_feature
        (B) LOCATION: 1
        (D) OTHER INFORMATION: /note= "primers directed to genomic
            intron DNA"

(xi) SEQUENCE DESCRIPTION: SEQ ID NO:122:

TGTAAAACGA CGGCCAGTGA AAGAAGAACA CATCCCACA                                                         39

(2) INFORMATION FOR SEQ ID NO:123:

(i) SEQUENCE CHARACTERISTICS:
        (A) LENGTH: 770 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:123:

```
Met Ser Leu Arg Ile Lys Ala Leu Asp Ala Ser Val Val Asn Lys Ile
1               5                  10                  15

Ala Ala Gly Glu Ile Ile Ile Ser Pro Val Asn Ala Leu Lys Glu Met
            20                  25                  30

Met Glu Asn Ser Ile Asp Ala Asn Ala Thr Met Ile Asp Ile Leu Val
        35                  40                  45

Lys Glu Gly Gly Ile Lys Val Leu Gln Ile Thr Asp Asn Gly Ser Gly
    50                  55                  60

Ile Asn Lys Ala Asp Leu Pro Ile Leu Cys Glu Arg Phe Thr Thr Ser
65                  70                  75                  80

Lys Leu Gln Lys Phe Glu Asp Leu Ser Gln Ile Gln Thr Tyr Gly Phe
                85                  90                  95

Arg Gly Glu Ala Leu Ala Ser Ile Ser His Val Ala Arg Val Thr Val
            100                 105                 110

Thr Thr Lys Val Lys Glu Asp Arg Cys Ala Trp Arg Val Ser Tyr Ala
        115                 120                 125

Glu Gly Lys Met Leu Glu Ser Pro Lys Pro Val Ala Gly Lys Asp Gly
    130                 135                 140

Thr Thr Ile Leu Val Glu Asp Leu Phe Phe Asn Ile Pro Ser Arg Leu
145                 150                 155                 160

Arg Ala Leu Arg Ser His Asn Asp Glu Tyr Ser Lys Ile Leu Asp Val
                165                 170                 175

Val Gly Arg Tyr Ala Ile His Ser Lys Asp Ile Gly Phe Ser Cys Lys
            180                 185                 190

Lys Phe Gly Asp Ser Asn Tyr Ser Leu Ser Val Lys Pro Ser Tyr Thr
        195                 200                 205

Val Gln Asp Arg Ile Arg Thr Val Phe Asn Lys Ser Val Ala Ser Asn
    210                 215                 220

Leu Ile Thr Phe His Ile Ser Lys Val Glu Asp Leu Asn Leu Glu Ser
```

```
225                 230                 235                 240
Val Asp Gly Lys Val Cys Asn Leu Asn Phe Ile Ser Lys Lys Ser Ile
                245                 250                 255
Ser Leu Ile Phe Phe Ile Asn Asn Arg Leu Val Thr Cys Asp Leu Leu
                260                 265                 270
Arg Arg Ala Leu Asn Ser Val Tyr Ser Asn Tyr Leu Pro Lys Gly Phe
                275                 280                 285
Arg Pro Phe Ile Tyr Leu Gly Ile Val Ile Asp Pro Ala Ala Val Asp
                290                 295                 300
Val Asn Val His Pro Thr Lys Arg Glu Val Arg Phe Leu Ser Gln Asp
305                 310                 315                 320
Glu Ile Ile Glu Lys Ile Ala Asn Gln Leu His Ala Glu Leu Ser Ala
                325                 330                 335
Ile Asp Thr Ser Arg Thr Phe Lys Ala Ser Ser Ile Ser Thr Asn Lys
                340                 345                 350
Pro Glu Ser Leu Ile Pro Phe Asn Asp Thr Ile Glu Ser Asp Arg Asn
                355                 360                 365
Arg Lys Ser Leu Arg Gln Ala Gln Val Val Glu Asn Ser Tyr Thr Thr
                370                 375                 380
Ala Asn Ser Gln Leu Arg Lys Ala Lys Arg Gln Glu Asn Lys Leu Val
385                 390                 395                 400
Arg Ile Asp Ala Ser Gln Ala Lys Ile Thr Ser Phe Leu Ser Ser Ser
                405                 410                 415
Gln Gln Phe Asn Phe Glu Gly Ser Ser Thr Lys Arg Gln Leu Ser Glu
                420                 425                 430
Pro Lys Val Thr Asn Val Ser His Ser Gln Glu Ala Glu Lys Leu Thr
                435                 440                 445
Leu Asn Glu Ser Glu Gln Pro Arg Asp Ala Asn Thr Ile Asn Asp Asn
450                 455                 460
Asp Leu Lys Asp Gln Pro Lys Lys Gln Lys Gln Leu Gly Asp Tyr
465                 470                 475                 480
Lys Val Pro Ser Ile Ala Asp Asp Glu Lys Asn Ala Leu Pro Ile Ser
                485                 490                 495
Lys Asp Gly Tyr Ile Arg Val Pro Lys Glu Arg Val Asn Val Asn Leu
                500                 505                 510
Thr Ser Ile Lys Lys Leu Arg Glu Lys Val Asp Asp Ser Ile His Arg
                515                 520                 525
Glu Leu Thr Asp Ile Phe Ala Asn Leu Asn Tyr Val Gly Val Val Asp
                530                 535                 540
Glu Glu Arg Arg Leu Ala Ala Ile Gln His Asp Leu Lys Leu Phe Leu
545                 550                 555                 560
Ile Asp Tyr Gly Ser Val Cys Tyr Glu Leu Phe Tyr Gln Ile Gly Leu
                565                 570                 575
Thr Asp Phe Ala Asn Phe Gly Lys Ile Asn Leu Gln Ser Thr Asn Val
                580                 585                 590
Ser Asp Asp Ile Val Leu Tyr Asn Leu Leu Ser Glu Phe Asp Glu Leu
                595                 600                 605
Asn Asp Asp Ala Ser Lys Glu Lys Ile Ile Ser Lys Ile Trp Asp Met
                610                 615                 620
Ser Ser Met Leu Asn Glu Tyr Tyr Ser Ile Glu Leu Val Asn Asp Gly
625                 630                 635                 640
Leu Asp Asn Asp Leu Lys Ser Val Lys Leu Lys Ser Leu Pro Leu Leu
                645                 650                 655
```

```
Leu Lys Gly Tyr Ile Pro Ser Leu Val Lys Leu Pro Phe Phe Ile Tyr
            660                 665                 670

Arg Leu Gly Lys Glu Val Asp Trp Glu Asp Glu Gln Glu Cys Leu Asp
            675                 680                 685

Gly Ile Leu Arg Glu Ile Ala Leu Leu Tyr Ile Pro Asp Met Val Pro
            690                 695                 700

Lys Val Asp Thr Leu Asp Ala Ser Leu Ser Glu Asp Glu Lys Ala Gln
705                 710                 715                 720

Phe Ile Asn Arg Lys Glu His Ile Ser Ser Leu Leu Glu His Val Leu
            725                 730                 735

Phe Pro Cys Ile Lys Arg Arg Phe Leu Ala Pro Arg His Ile Leu Lys
            740                 745                 750

Asp Val Val Glu Ile Ala Asn Leu Pro Asp Leu Tyr Lys Val Phe Glu
            755                 760                 765

Arg Cys
    770

(2) INFORMATION FOR SEQ ID NO:124:

(i) SEQUENCE CHARACTERISTICS:
        (A) LENGTH: 64 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:124:

Val Asn Arg Ile Ala Ala Gly Glu Val Ile Gln Arg Pro Ala Asn Ala
1               5                   10                  15

Ile Lys Glu Met Ile Glu Asn Cys Leu Asp Ala Lys Phe Thr Ser Ile
            20                  25                  30

Gln Val Ile Val Lys Glu Gly Gly Leu Lys Leu Ile Gln Ile Gln Asp
            35                  40                  45

Asn Gly Thr Gly Ile Arg Lys Glu Asp Leu Asp Ile Val Cys Glu Arg
    50                  55                  60

(2) INFORMATION FOR SEQ ID NO:125:

(i) SEQUENCE CHARACTERISTICS:
        (A) LENGTH: 64 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:125:

Val Asn Arg Ile Ala Ala Gly Glu Val Ile Gln Arg Pro Ala Asn Ala
1               5                   10                  15

Ile Lys Glu Met Ile Glu Asn Cys Leu Asp Ala Lys Ser Thr Ser Ile
            20                  25                  30

Gln Val Ile Val Lys Glu Gly Gly Leu Lys Leu Ile Gln Ile Gln Asp
            35                  40                  45

Asn Gly Thr Gly Ile Arg Lys Glu Asp Leu Asp Ile Val Cys Glu Arg
    50                  55                  60

(2) INFORMATION FOR SEQ ID NO:126:

(i) SEQUENCE CHARACTERISTICS:
```

(A) LENGTH: 52 amino acids
(B) TYPE: amino acid
(C) STRANDEDNESS: single
(D) TOPOLOGY: linear (ii) MOLECULE TYPE: protein (xi) SEQUENCE DESCRIPTION: SEQ ID NO:126:

Pro Ala Asn Ala Ile Lys Glu Met Ile Glu Asn Cys Leu Asp Ala Lys
1               5                   10                  15

Ser Thr Asn Ile Gln Val Val Val Lys Glu Gly Gly Leu Lys Leu Ile
                20                  25                  30

Gln Ile Gln Asp Asn Gly Thr Gly Ile Arg Lys Glu Asp Leu Asp Ile
            35                  40                  45

Val Cys Glu Arg
    50

(2) INFORMATION FOR SEQ ID NO:127:

(i) SEQUENCE CHARACTERISTICS:
(A) LENGTH: 64 amino acids
(B) TYPE: amino acid
(C) STRANDEDNESS: single
(D) TOPOLOGY: linear (ii) MOLECULE TYPE: protein (xi) SEQUENCE DESCRIPTION: SEQ ID NO:127:

Val Asn Lys Ile Ala Ala Gly Glu Ile Ile Ile Ser Pro Val Asn Ala
1               5                   10                  15

Leu Lys Glu Met Met Glu Asn Ser Ile Asp Ala Asn Ala Thr Met Ile
                20                  25                  30

Asp Ile Leu Val Lys Glu Gly Gly Ile Lys Val Leu Gln Ile Thr Asp
            35                  40                  45

Asn Gly Ser Gly Ile Asn Lys Ala Asp Leu Pro Ile Leu Cys Glu Arg
    50                  55                  60

(2) INFORMATION FOR SEQ ID NO:128:

(i) SEQUENCE CHARACTERISTICS:
(A) LENGTH: 64 amino acids
(B) TYPE: amino acid
(C) STRANDEDNESS: single
(D) TOPOLOGY: linear (ii) MOLECULE TYPE: protein (xi) SEQUENCE DESCRIPTION: SEQ ID NO:128:

Val His Arg Ile Thr Ser Gly Gln Val Ile Thr Asp Leu Thr Thr Ala
1               5                   10                  15

Val Lys Glu Leu Val Asp Asn Ser Ile Asp Ala Asn Ala Asn Gln Ile
                20                  25                  30

Glu Ile Ile Phe Lys Asp Tyr Gly Leu Glu Ser Ile Glu Cys Ser Asp
            35                  40                  45

Asn Gly Asp Gly Ile Asp Pro Ser Asn Tyr Glu Phe Leu Ala Leu Lys
    50                  55                  60

(2) INFORMATION FOR SEQ ID NO:129:

(i) SEQUENCE CHARACTERISTICS:
(A) LENGTH: 64 amino acids
(B) TYPE: amino acid
(C) STRANDEDNESS: single
(D) TOPOLOGY: linear (ii) MOLECULE TYPE: protein (xi) SEQUENCE DESCRIPTION: SEQ ID NO:129:

Ala Asn Gln Ile Ala Ala Gly Glu Val Val Glu Arg Pro Ala Ser Val
1               5                   10                  15

Val Lys Glu Leu Val Glu Asn Ser Leu Asp Ala Gly Ala Thr Arg Ile
            20                  25                  30

Asp Ile Asp Ile Glu Arg Gly Gly Ala Lys Leu Ile Arg Ile Arg Asp
            35                  40                  45

Asn Gly Cys Gly Ile Lys Lys Asp Glu Leu Ala Leu Ala Leu Ala Arg
50                  55                  60

(2) INFORMATION FOR SEQ ID NO:130:

(i) SEQUENCE CHARACTERISTICS:
        (A) LENGTH: 64 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:130:

Ala Asn Gln Ile Ala Ala Gly Glu Val Val Glu Arg Pro Ala Ser Val
1               5                   10                  15

Val Lys Glu Leu Val Glu Asn Ser Leu Asp Ala Gly Ala Thr Arg Val
            20                  25                  30

Asp Ile Asp Ile Glu Arg Gly Gly Ala Lys Leu Ile Arg Ile Arg Asp
            35                  40                  45

Asn Gly Cys Gly Ile Lys Lys Glu Glu Leu Ala Leu Ala Leu Ala Arg
50                  55                  60

(2) INFORMATION FOR SEQ ID NO:131:

(i) SEQUENCE CHARACTERISTICS:
        (A) LENGTH: 64 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:131:

Ala Asn Gln Ile Ala Ala Gly Glu Val Ile Glu Arg Pro Ala Ser Val
1               5                   10                  15

Cys Lys Glu Leu Val Glu Asn Ala Ile Asp Ala Gly Ser Ser Gln Ile
            20                  25                  30

Ile Ile Glu Ile Glu Glu Ala Gly Leu Lys Lys Val Gln Ile Thr Asp
            35                  40                  45

Asn Gly His Gly Ile Ala His Asp Glu Val Glu Leu Ala Leu Arg Arg
50                  55                  60

(2) INFORMATION FOR SEQ ID NO:132:

(i) SEQUENCE CHARACTERISTICS:
        (A) LENGTH: 2687 base pairs
        (B) TYPE: nucleic acid
        (C) STRANDEDNESS: single
        (D) TOPOLOGY: linear (ii) MOLECULE TYPE: DNA (genomic)

(viii) POSITION IN GENOME:

(B) MAP POSITION: 7q (xi) SEQUENCE DESCRIPTION: SEQ ID NO:132:

```
CCATGGAGCG AGCTGAGAGC TCGAGTACAG AACCTGCTAA GGCCATCAAA CCTATTGATC      60
GGAAGTCAGT CCATCAGATT TGCTCTGGGC AGGTGGTACT GAGTCTAAGC ACTGCGGTAA     120
AGGAGTTAGT AGAAAACAGT CTGGATGCTG GTGCCACTAA TATTGATCTA AAGCTTAAGG     180
ACTATGGAGT GGATCTTATT GAAGTTTCAG ACAATGGATG TGGGGTAGAA GAAGAAAACT     240
TCGAAGGCTT AACTCTGAAA CATCACACAT CTAAGATTCA AGAGTTTGCC GACCTAACTC     300
AGGTTGAAAC TTTTGGCTTT CGGGGGGAAG CTCTGAGCTC ACTTTGTGCA CTGAGCGATG     360
TCACCATTTC TACCTGCCAC GCATCGGCGA AGGTTGGAAC TCGACTGATG TTTGATCACA     420
ATGGGAAAAT TATCCAGAAA ACCCCCTACC CCCGCCCCAG AGGGACCACA GTCAGCGTGC     480
AGCAGTTATT TTCCACACTA CCTGTGCGCC ATAAGGAATT TCAAAGGAAT ATTAAGAAGG     540
AGTATGCCAA AATGGTCCAG GTCTTACATG CATACTGTAT CATTTCAGCA GGCATCCGTG     600
TAAGTTGCAC CAATCAGCTT GGACAAGGAA ACGACAGCC TGTGGTATGC ACAGGTGGAA     660
GCCCCAGCAT AAAGGAAAAT ATCGGCTCTG TGTTTGGGCA GAAGCAGTTG CAAAGCCTCA     720
TTCCTTTTGT TCAGCTGCCC CCTAGTGACT CCGTGTGTGA AGAGTACGGT TTGAGCTGTT     780
CGGATGCTCT GCATAATCTT TTTTACATCT CAGGTTTCAT TTCACAATGC ACGCATGGAG     840
TTGGAAGGAG TTCAACAGAC AGACAGTTTT TCTTTATCAA CCGGCGGCCT TGTGACCCAG     900
CAAAGGTCTG CAGACTCGTG AATGAGGTCT ACCACATGTA TAATCGACAC CAGTATCCAT     960
TTGTTGTTCT TAACATTTCT GTTGATTCAG AATGCGTTGA TATCAATGTT ACTCCAGATA    1020
AAAGGCAAAT TTTGCTACAA GAGGAAAAGC TTTTGTTGGC AGTTTTAAAG ACCTCTTTGA    1080
TAGGAATGTT TGATAGTGAT GTCAACAAGC TAAATGTCAG TCAGCAGCCA CTGCTGGATG    1140
TTGAAGGTAA CTTAATAAAA ATGCATGCAG CGGATTTGGA AAAGCCCATG GTAGAAAAGC    1200
AGGATCAATC CCCTTCATTA AGGACTGGAG AAGAAAAAAA AGACGTGTCC ATTTCCAGAC    1260
TGCGAGAGGC CTTTTCTCTT CGTCACACAA CAGAGAACAA GCCTCACAGC CAAAGACTC    1320
CAGAACCAAG AAGGAGCCCT CTAGGACAGA AAAGGGGTAT GCTGTCTTCT AGCACTTCAG    1380
GTGCCATCTC TGACAAAGGC GTCCTGAGAT CTCAGAAAGA GGCAGTGAGT TCCAGTCACG    1440
GACCCAGTGA CCCTACGGAC AGAGCGGAGG TGGAGAAGGA CTCGGGGCAC GGCAGCACTT    1500
CCGTGGATTC TGAGGGGTTC AGCATCCCAG ACACGGGCAG TCACTGCAGC AGCGAGTATG    1560
CGGCCAGCTC CCCAGGGGAC AGGGGCTCGC AGGAACATGT GGACTCTCAG GAGAAAGCGC    1620
CTGAAACTGA CGACTCTTTT TCAGATGTGG ACTGCCATTC AAACCAGGAA GATACCGGAT    1680
GTAAATTTCG AGTTTTGCCT CAGCCAACTA ATCTCGCAAC CCCAAACACA AAGCGTTTTA    1740
AAAAAGAAGA AATTCTTTCC AGTTCTGACA TTTGTCAAAA GTTAGTAAAT ACTCAGGACA    1800
TGTCAGCCTC TCAGGTTGAT TGAGCTGTGA AAATTAATAA GAAAGTTGTG CCCCTGGACT    1860
TTTCTATGAG TTCTTTAGCT AAACGAATAA AGCAGTTACA TCATGAAGCA CAGCAAAGTG    1920
AAGGGGAACA GAATTACAGG AAGTTTAGGG CAAAGATTTG TCCTGGAGAA AATCAAGCAG    1980
CCGAAGATGA ACTAAGAAAA GAGATAAGTA AAACGATGTT TGCAGAAATG GAAATCATTG    2040
GTCAGTTTAA CCTGGGATTT ATAATAACCA AACTGAATGA GGATATCTTC ATAGTGGACC    2100
AGCATGCCAC GGACGAGAAG TATAACTTCG AGATGCTGCA GCAGCACACC GTGCTCCAGG    2160
GGCAGAGGCT CATAGCACCT CAGACTCTCA ACTTAACTGC TGTTAATGAA GCTGTTCTGA    2220
TAGAAAATCT GGAAATATTT AGAAGAATG GCTTTGATTT TGTTATCGAT GAAAATGCTC    2280
```

```
CAGTCACTGA AAGGGCTAAA CTGATTTCCT TGCCAACTAG TAAAAACTGG ACCTTCGGAC    2340

CCCAGGACGT CGATGAACTG ATCTTCATGC TGAGCGACAG CCCTGGGGTC ATGTGCCGCC    2400

CTTCCCGAGT CAAGCAGATG TTTGCCTCCA GAGCCTGCCG GAAGTCGGTG ATGATTGGGA    2460

CTGCTCTCAA CACAAGCGAA TGAAGAAACT GATCACCCAC ATGGGGGAGA TGGGCCACCC    2520

CTGGAACTGT CCCCATGGAA GGCCACCATG AGACACATCG CCAACCTGGG TGTCATTTCT    2580

CAGAACTGAC CGTAGTCACT GTATGGAATA ATTGGTTTTA TCGCAGATTT TTATGTTTTG    2640

AAAGACAGAG TCTTCACTAA CCTTTTTTGT TTTAAAATGA AACCTGC                  2687
```

(2) INFORMATION FOR SEQ ID NO:133:

(i) SEQUENCE CHARACTERISTICS:
        (A) LENGTH: 862 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:133:

```
Met Glu Arg Ala Glu Ser Ser Thr Glu Pro Ala Lys Ala Ile Lys
1               5                   10                  15

Pro Ile Asp Arg Lys Ser Val His Gln Ile Cys Ser Gly Gln Val Val
            20                  25                  30

Leu Ser Leu Ser Thr Ala Val Lys Glu Leu Val Glu Asn Ser Leu Asp
        35                  40                  45

Ala Gly Ala Thr Asn Ile Asp Leu Lys Leu Lys Asp Tyr Gly Val Asp
    50                  55                  60

Leu Ile Glu Val Ser Asp Asn Gly Cys Gly Val Glu Glu Asn Phe
65                  70                  75                  80

Glu Gly Leu Thr Leu Lys His His Thr Ser Lys Ile Gln Glu Phe Ala
                85                  90                  95

Asp Leu Thr Gln Val Glu Thr Phe Gly Phe Arg Gly Glu Ala Leu Ser
            100                 105                 110

Ser Leu Cys Ala Leu Ser Asp Val Thr Ile Ser Thr Cys His Ala Ser
        115                 120                 125

Ala Lys Val Gly Thr Arg Leu Met Phe Asp His Asn Gly Lys Ile Ile
    130                 135                 140

Gln Lys Thr Pro Tyr Pro Arg Pro Arg Gly Thr Thr Val Ser Val Gln
145                 150                 155                 160

Gln Leu Phe Ser Thr Leu Pro Val Arg His Lys Glu Phe Gln Arg Asn
                165                 170                 175

Ile Lys Lys Glu Tyr Ala Lys Met Val Gln Val Leu His Ala Tyr Cys
            180                 185                 190

Ile Ile Ser Ala Gly Ile Arg Val Ser Cys Thr Asn Gln Leu Gly Gln
        195                 200                 205

Gly Lys Arg Gln Pro Val Val Cys Ile Gly Gly Ser Pro Ser Ile Lys
    210                 215                 220

Glu Asn Ile Gly Ser Val Phe Gly Gln Lys Gln Leu Gln Ser Leu Ile
225                 230                 235                 240

Pro Phe Val Gln Leu Pro Pro Ser Asp Ser Val Cys Glu Glu Tyr Gly
                245                 250                 255

Leu Ser Cys Ser Asp Ala Leu His Asn Leu Phe Tyr Ile Ser Gly Phe
            260                 265                 270
```

-continued

```
Ile Ser Gln Cys Thr His Gly Val Gly Arg Ser Ser Thr Asp Arg Gln
            275                 280                 285

Phe Phe Phe Ile Asn Arg Arg Pro Cys Asp Pro Ala Lys Val Cys Arg
        290                 295                 300

Leu Val Asn Glu Val Tyr His Met Tyr Asn Arg His Gln Tyr Pro Phe
305                 310                 315                 320

Val Val Leu Asn Ile Ser Val Asp Ser Glu Cys Val Asp Ile Asn Val
                325                 330                 335

Thr Pro Asp Lys Arg Gln Ile Leu Leu Gln Glu Glu Lys Leu Leu Leu
            340                 345                 350

Ala Val Leu Lys Thr Ser Leu Ile Gly Met Phe Asp Ser Asp Val Asn
            355                 360                 365

Lys Leu Asn Val Ser Gln Gln Pro Leu Leu Asp Val Glu Gly Asn Leu
            370                 375                 380

Ile Lys Met His Ala Ala Asp Leu Glu Lys Pro Met Val Glu His Gln
385                 390                 395                 400

Asp Gln Ser Pro Ser Leu Arg Ile Gly Glu Glu Lys Lys Asp Val Ser
                405                 410                 415

Ile Ser Arg Leu Arg Glu Ala Phe Ser Leu Arg His Thr Thr Glu Asn
            420                 425                 430

Lys Pro His Ser Pro Lys Thr Pro Glu Pro Arg Arg Ser Pro Leu Gly
            435                 440                 445

Gln Lys Arg Gly Met Leu Ser Ser Ser Thr Ser Gly Ala Ile Ser Asp
    450                 455                 460

Lys Gly Val Leu Arg Ser Gln Lys Glu Ala Val Ser Ser Ser His Gly
465                 470                 475                 480

Pro Ser Asp Pro Thr Asp Arg Ala Glu Val Glu Lys Asp Ser Gly His
                485                 490                 495

Gly Ser Thr Ser Val Asp Ser Glu Gly Phe Ser Ile Pro Asp Thr Gly
            500                 505                 510

Ser His Cys Ser Ser Glu Tyr Ala Ala Ser Ser Pro Gly Asp Arg Gly
            515                 520                 525

Ser Gln Glu His Val Asp Ser Gln Glu Lys Ala Pro Glu Thr Asp Asp
530                 535                 540

Ser Phe Ser Asp Val Asp Cys His Ser Asn Gln Glu Asp Thr Gly Cys
545                 550                 555                 560

Lys Phe Arg Val Leu Pro Gln Pro Ile Asn Leu Ala Thr Pro Asn Thr
                565                 570                 575

Lys Arg Phe Lys Lys Glu Glu Ile Leu Ser Ser Ser Asp Ile Cys Gln
            580                 585                 590

Lys Leu Val Asn Thr Gln Asp Met Ser Ala Ser Gln Val Asp Val Ala
            595                 600                 605

Val Lys Ile Asn Lys Lys Val Val Pro Leu Asp Phe Ser Met Ser Ser
        610                 615                 620

Leu Ala Lys Arg Ile Lys Gln Leu His His Glu Ala Gln Gln Ser Glu
625                 630                 635                 640

Gly Glu Gln Asn Tyr Arg Lys Phe Arg Ala Lys Ile Cys Pro Gly Glu
                645                 650                 655

Asn Gln Ala Ala Glu Asp Glu Leu Arg Lys Glu Ile Ser Lys Thr Met
            660                 665                 670

Phe Ala Glu Met Glu Ile Ile Gly Gln Phe Asn Leu Gly Phe Ile Ile
            675                 680                 685

Thr Lys Leu Asn Glu Asp Ile Phe Ile Val Asp Gln His Ala Thr Asp
```

-continued

```
            690                 695                 700
Glu Lys Tyr Asn Phe Glu Met Leu Gln Gln His Thr Val Leu Gln Gly
705                 710                 715                 720

Gln Arg Leu Ile Ala Pro Gln Thr Leu Asn Leu Thr Ala Val Asn Glu
                725                 730                 735

Ala Val Leu Ile Glu Asn Leu Glu Ile Phe Arg Lys Asn Gly Phe Asp
                740                 745                 750

Phe Val Ile Asp Glu Asn Ala Pro Val Thr Glu Arg Ala Lys Leu Ile
                755                 760                 765

Ser Leu Pro Thr Ser Lys Asn Trp Thr Phe Gly Pro Gln Asp Val Asp
770                 775                 780

Glu Leu Ile Phe Met Leu Ser Asp Ser Pro Gly Val Met Cys Arg Pro
785                 790                 795                 800

Ser Arg Val Lys Gln Met Phe Ala Ser Arg Ala Cys Arg Lys Ser Val
                805                 810                 815

Met Ile Gly Thr Ala Leu Asn Thr Ser Glu Met Lys Lys Leu Ile Thr
                820                 825                 830

His Met Gly Glu Met Gly His Pro Trp Asn Cys Pro His Gly Arg Pro
                835                 840                 845

Thr Met Arg His Ile Ala Asn Leu Gly Val Ile Ser Gln Asn
850                 855                 860
```

(2) INFORMATION FOR SEQ ID NO:134:

(i) SEQUENCE CHARACTERISTICS:
        (A) LENGTH: 903 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:134:

```
Met Phe His His Ile Glu Asn Leu Leu Ile Glu Thr Glu Lys Arg Cys
1               5                   10                  15

Lys Gln Lys Glu Gln Arg Tyr Ile Pro Val Lys Tyr Leu Phe Ser Met
                20                  25                  30

Thr Gln Ile His Gln Ile Asn Asp Ile Asp Val His Arg Ile Thr Ser
                35                  40                  45

Gly Gln Val Ile Thr Asp Leu Thr Thr Ala Val Lys Glu Leu Val Asp
50                  55                  60

Asn Ser Ile Asp Ala Asn Ala Asn Gln Ile Glu Ile Phe Lys Asp
65                  70                  75                  80

Tyr Gly Leu Glu Ser Ile Glu Cys Ser Asp Asn Gly Asp Gly Ile Asp
                85                  90                  95

Pro Ser Asn Tyr Glu Phe Leu Ala Leu Lys His Tyr Thr Ser Lys Ile
                100                 105                 110

Ala Lys Phe Gln Asp Val Ala Lys Val Gln Thr Leu Gly Phe Arg Gly
                115                 120                 125

Glu Ala Leu Ser Ser Leu Cys Gly Ile Ala Lys Leu Ser Val Ile Thr
                130                 135                 140

Thr Thr Ser Pro Pro Lys Ala Asp Lys Leu Glu Tyr Asp Met Val Gly
145                 150                 155                 160

His Ile Thr Ser Lys Thr Thr Ser Arg Asn Lys Gly Thr Thr Val Leu
                165                 170                 175

Val Ser Gln Leu Phe His Asn Leu Pro Val Arg Gln Lys Glu Phe Ser
```

-continued

```
                180             185             190
Lys Thr Phe Lys Arg Gln Phe Thr Lys Cys Leu Thr Val Ile Gln Gly
            195             200             205
Tyr Ala Ile Ile Asn Ala Ala Ile Lys Phe Ser Val Trp Asn Ile Thr
            210             215             220
Pro Lys Gly Lys Lys Asn Leu Ile Leu Ser Thr Met Arg Asn Ser Ser
225             230             235             240
Met Arg Lys Asn Ile Ser Ser Val Phe Gly Ala Gly Met Phe Gly
            245             250             255
Leu Glu Glu Val Asp Leu Val Leu Asp Leu Asn Pro Phe Lys Asn Arg
            260             265             270
Met Leu Gly Lys Tyr Thr Asp Pro Asp Phe Leu Asp Leu Asp Tyr
            275             280             285
Lys Ile Arg Val Lys Gly Tyr Ile Ser Gln Asn Ser Phe Gly Cys Gly
            290             295             300
Arg Asn Ser Lys Asp Arg Gln Phe Ile Tyr Val Asn Lys Arg Pro Val
305             310             315             320
Glu Tyr Ser Thr Leu Leu Lys Cys Cys Asn Glu Val Tyr Lys Thr Phe
            325             330             335
Asn Asn Val Gln Phe Pro Ala Val Phe Leu Asn Leu Glu Leu Pro Met
            340             345             350
Ser Leu Ile Asp Val Asn Val Thr Pro Asp Lys Arg Val Ile Leu Leu
            355             360             365
His Asn Glu Arg Ala Val Ile Asp Ile Phe Lys Thr Thr Leu Ser Asp
            370             375             380
Tyr Tyr Asn Arg Gln Glu Leu Ala Leu Pro Lys Arg Met Cys Ser Gln
385             390             395             400
Ser Glu Gln Gln Ala Gln Lys Arg Leu Lys Thr Glu Val Phe Asp Asp
            405             410             415
Arg Ser Thr Thr His Glu Ser Asp Asn Glu Asn Tyr His Thr Ala Arg
            420             425             430
Ser Glu Ser Asn Gln Ser Asn His Ala His Phe Asn Ser Thr Thr Gly
            435             440             445
Val Ile Asp Lys Ser Asn Gly Thr Glu Leu Thr Ser Val Met Asp Gly
            450             455             460
Asn Tyr Thr Asn Val Thr Asp Val Ile Gly Ser Glu Cys Glu Val Ser
465             470             475             480
Val Asp Ser Ser Val Val Leu Asp Glu Gly Asn Ser Ser Thr Pro Thr
            485             490             495
Lys Lys Leu Pro Ser Ile Lys Thr Asp Ser Gln Asn Leu Ser Asp Leu
            500             505             510
Asn Leu Asn Asn Phe Ser Asn Pro Glu Phe Gln Asn Ile Thr Ser Pro
            515             520             525
Asp Lys Ala Arg Ser Leu Glu Lys Val Val Glu Glu Pro Val Tyr Phe
            530             535             540
Asp Ile Asp Gly Glu Lys Phe Gln Glu Lys Ala Val Leu Ser Gln Ala
545             550             555             560
Asp Gly Leu Val Phe Val Asp Asn Glu Cys His Glu His Thr Asn Asp
            565             570             575
Cys Cys His Gln Glu Arg Arg Gly Ser Thr Asp Ile Glu Gln Asp Asp
            580             585             590
Glu Ala Asp Ser Ile Tyr Ala Glu Ile Glu Pro Val Glu Ile Asn Val
            595             600             605
```

```
Arg Thr Pro Leu Lys Asn Ser Arg Lys Ser Ile Ser Lys Asp Asn Tyr
    610                 615                 620

Arg Ser Leu Ser Asp Gly Leu Thr His Arg Lys Phe Glu Asp Glu Ile
625                 630                 635                 640

Leu Glu Tyr Asn Leu Ser Thr Lys Asn Phe Lys Glu Ile Ser Lys Asn
                645                 650                 655

Gly Lys Gln Met Ser Ser Ile Ile Ser Lys Arg Lys Ser Glu Ala Gln
                660                 665                 670

Glu Asn Ile Ile Lys Asn Lys Asp Glu Leu Glu Asp Phe Glu Gln Gly
                675                 680                 685

Glu Lys Tyr Leu Thr Leu Thr Val Ser Lys Asn Asp Phe Lys Lys Met
    690                 695                 700

Glu Val Val Gly Gln Phe Asn Leu Gly Phe Ile Ile Val Thr Arg Lys
705                 710                 715                 720

Val Asp Asn Lys Ser Lys Leu Phe Ile Val Asp Gln His Ala Ser Asp
                725                 730                 735

Glu Lys Tyr Asn Phe Glu Thr Leu Gln Ala Val Thr Val Phe Lys Ser
                740                 745                 750

Gln Lys Leu Ile Ile Pro Gln Pro Val Glu Leu Ser Val Ile Asp Glu
                755                 760                 765

Leu Val Val Leu Asp Asn Leu Pro Val Phe Glu Lys Asn Gly Phe Lys
    770                 775                 780

Leu Lys Ile Asp Glu Glu Glu Phe Gly Ser Arg Val Lys Leu Leu
785                 790                 795                 800

Ser Leu Pro Thr Ser Lys Gln Thr Leu Phe Asp Leu Gly Asp Phe Asn
                805                 810                 815

Glu Leu Ile His Leu Ile Lys Glu Asp Gly Gly Leu Arg Arg Asp Asn
                820                 825                 830

Ile Arg Cys Ser Lys Ile Arg Ser Met Phe Ala Met Arg Ala Cys Arg
                835                 840                 845

Ser Ser Ile Met Ile Gly Lys Pro Leu Asn Lys Lys Thr Met Thr Arg
    850                 855                 860

Val Val His Asn Leu Ser Glu Leu Asp Lys Pro Trp Asn Cys Pro His
865                 870                 875                 880

Gly Arg Pro Thr Met Arg His Leu Met Glu Ile Arg Asp Trp Ser Ser
                885                 890                 895

Phe Ser Lys Asp Tyr Glu Ile
                900
```

(2) INFORMATION FOR SEQ ID NO:135:

(i) SEQUENCE CHARACTERISTICS:
        (A) LENGTH: 2577 base pairs
        (B) TYPE: nucleic acid
        (C) STRANDEDNESS: single
        (D) TOPOLOGY: linear (xi) SEQUENCE DESCRIPTION: SEQ ID NO:135:

```
TTCCGGCCAA TGCTATCAAA GAGATGATAG AAAACTGTTT AGATGCAAAA TCTACAAATA      60

TTCAAGTGGT TGTTAAGGAA GGTGGCCTGA AGCTAATTCA GATCCAAGAC AATGGCACTG     120

GAATCAGGAA GGAAGATCTG GATATTGTGT GTGAGAGGTT CACTACGAGT AAACTGCAGA     180

CTTTTGAGGA TTTAGCCAGT ATTTCTACCT ATGGCTTTCG TGGTGAGCAT TTGGCAAGCA     240

TAAGTCATGT GGCCCATGTC ACTATTACAA CCAAAACAGC TGATGGGAAA TGTGCGTACA     300
```

-continued

```
GAGCAAGTTA CTCAGATGGA AAGCTGCAAG CCCCTCCTAA ACCCTGTGCA GGCAACCAGG    360
GCACCCTGAT CACGGTGGAA GACCTTTTTT ACAACATAAT CACAAGGAGG AAAGCTTTAA    420
AAAATCCAAG TGAAGAGTAC GGAAAAATTT TGGAAGTTGT TGGCAGGTAT TCAATACACA    480
ATTCAGGCAT TAGTATCTCA GTTAAAAAAC AAGGTGAGAC AGTATCTGAT GTCAGAACAC    540
TGCCCAATGC CACAACCGTG GACAACATTC GCTCCATCTT TGGAAATGCG GTTAGTCGAG    600
AACTGATAGA AGTTGGGTGT GAGGATAAAA CCCTAGCTTT CAAAATGAAT GGCTATATAT    660
CGAATGCAAA GTATTCAGTG AAGAAGTGCA TTTTCCTACT CTTCATCAAC CACCGTCTGG    720
TAGAATCAGC TGCCTTGAGA AAAGCCATTG AAACTGTATA TGCAGCATAC TTGCCAAAAA    780
CACACACCCA TTCCTGTACC TCAGTTTGAA ATCAGCCCTC AGAACGTGAC GTCAATGTAC    840
ACCCCACCAA GACAGAAGTT CATTTTCTGC ACGAGGAGAG CATTCTGCAG CGTGTGCAGC    900
AGCACATTGA GAGCAAGCTG CTGGGCTCCA ATTCCTCCAG GATGTATTTC ACCCAGACCT    960
TGCTTCCAGG ACTTGCTGGG CCTCTGGGGA GGCAGCTAGA CCCACGACAG GGGTGGCTTC   1020
CTCATCCACT AGTGGAAGTG GCGACAAGGT CTACGCTTAC CAGATGTCGC GTACGGACTC   1080
CCGGGATCAG AAGCTTGACG CCTTTCTGCA GCCTGTAACC AGCCTTGTGC CCAGCCAGCC   1140
CCAGGACCCC CGCCCTGTCC GAGGGGCCAG GACAGAGGGC TCTCCTGAAA GGGCCACGCG   1200
GGAGGATGAG GAGATGCTTG CTCTCCCAGC CCCCGCTGAA GCAGCTGCTG AGAGTGAGAA   1260
CTTGGAGAGG GAATCACTAA TGGAGACTTC AGACGCAGCC CAGAAAGCGG CACCCACTTC   1320
CAGTCCAGGA AGCTCCAGAA AGAGTCATCG GGAGGACTCT GATGTGGAAA TGGTGGAAAA   1380
TGCTTCCGGG AAGGAAATGA CAGCTGCTTG CTACCCCAGG AGGAGGATCA TTAACCTCAC   1440
CAGCGTCTTG AGTCTCCAGG AAGAGATTAG TGAGCGGTGC CATGAGACTC TCCGGGAGAT   1500
ACTCCGTAAC CATTCCTTTG TGGGCTGTGT GAATCCTCAG TGGGCCTTGG CACAGCACCA   1560
GACCAAGCTA TACCTCCTCA ACACTACCAA GCTCAGTGAA GAGCTGTTCT ACCAGATACT   1620
CATTTATGAT TTTGCCAACT TTGGTGTTCT GAGGTTATCG GAACCAGCGC CACTCTTCGA   1680
CCTGGCCATG CTGGCTTAGA CAGTCCTGAA AGTGGCTGGA CAGAGGACGA CGGCCCGAAG   1740
AAGGGCTTGC AGAGTACATT GTCGAGTTTC TGAAGAGAAG CGAGATGCTT GCAGACTATT   1800
CTCTGTGAGA TCGATGAGAA GGGAACCTGA TTGATTACTC TTCTGATGAC AGCTATGTGC   1860
CACCTTTGGA GGGACTGCCT ATCTTCATTC TTCGACTGGC CACTGAGGTG AATTGGGTGA   1920
AGAAAAGGAG TGTTTTGAAA GTCTCAGTAA AGAATGTGCT ATGTTTTACT CCATTCGGAA   1980
GCAGTATATA CTGGAGGAGT CGACCCTCTC AGGCCAGCAG AGTGACATGC CTGGCTCCAC   2040
GTCAAAGCCC TGGAAGTGGA CTGTGGAGCA CATTATCTAT AAAGCCTTCC GCTCACACCT   2100
CCTACCTCCG AAGCATTTCA CAGAAGATGG CAATGTCCTG CAGCTTGCCA ACCTGCCAGA   2160
TCTATACAAA GTCTTTGAGC GGTGTTAAAT ACAATCATAG CCACCGTAGA GACTGCATGA   2220
CCATCCAAGG CGAAGTGTAT GGTACTAATC TGGAAGCCAC AGAATAGGAC ACTTGGTTTC   2280
AGCTCCAGGG TTTTCAGTGC TCACTATTCT TGTTCTGTAT CCCAGTATTG GTGCTGCAAC   2340
TTAATGTACT TCACCTGTGG ATTGGCTGCA AATAAACTCA CGTGTATTGG AAAAAAGGAA   2400
TTCCTGCAGC CCGGGGATCC CACTAGTTCT AGAGCGGCCG CCACCGGTGG AGCTCCAGCT   2460
TTTGTTCCCT TTAGTGAGGG TTAATTTCGA GCTTGGCGTA ATCATGGTCA TAGCTGTTTC   2520
CTGTGTGAAA TTGTTATCCG CTCACAATTC CACACAACAT ACGAGCCGGA AGCATAA     2577
```

(2) INFORMATION FOR SEQ ID NO:136:

-continued

```
    (i) SEQUENCE CHARACTERISTICS:
        (A) LENGTH: 728 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:136:

Pro Ala Asn Ala Ile Lys Glu Met Ile Glu Asn Cys Leu Asp Ala Lys
  1               5                  10                  15

Ser Thr Asn Ile Gln Val Val Lys Glu Gly Gly Leu Lys Leu Ile
                 20                  25                  30

Gln Ile Gln Asp Asn Gly Thr Gly Ile Arg Lys Glu Asp Leu Asp Ile
                 35                  40                  45

Val Cys Glu Arg Phe Thr Thr Ser Lys Leu Gln Thr Phe Glu Asp Leu
 50                  55                  60

Ala Ser Ile Ser Thr Tyr Gly Phe Arg Gly Glu His Leu Ala Ser Ile
 65                  70                  75                  80

Ser His Val Ala His Val Thr Ile Thr Thr Lys Thr Ala Asp Gly Lys
                 85                  90                  95

Cys Ala Tyr Arg Ala Ser Tyr Ser Asp Gly Lys Leu Gln Ala Pro Pro
                100                 105                 110

Lys Pro Cys Ala Gly Asn Gln Gly Thr Leu Ile Thr Val Glu Asp Leu
                115                 120                 125

Phe Tyr Asn Ile Ile Thr Arg Arg Lys Ala Leu Lys Asn Pro Ser Glu
                130                 135                 140

Glu Tyr Gly Lys Ile Leu Glu Val Val Gly Arg Tyr Ser Ile His Asn
145                 150                 155                 160

Ser Gly Ile Ser Ile Ser Val Lys Lys Gln Gly Glu Thr Val Ser Asp
                165                 170                 175

Val Arg Thr Leu Pro Asn Ala Thr Thr Val Asp Asn Ile Arg Ser Ile
                180                 185                 190

Phe Gly Asn Ala Val Ser Arg Glu Leu Ile Glu Val Gly Cys Glu Asp
                195                 200                 205

Lys Thr Leu Ala Phe Lys Met Asn Gly Tyr Ile Ser Asn Ala Lys Tyr
                210                 215                 220

Ser Val Lys Lys Cys Ile Phe Leu Leu Phe Ile Asn His Arg Leu Val
225                 230                 235                 240

Glu Ser Ala Ala Leu Arg Lys Ala Ile Glu Thr Val Tyr Ala Ala Tyr
                245                 250                 255

Leu Pro Lys Thr His Thr His Ser Cys Thr Ser Val Glx Asn Gln Pro
                260                 265                 270

Ser Glu Arg Asp Val Asn Val His Pro Thr Lys Thr Glu Val His Phe
                275                 280                 285

Leu His Glu Glu Ser Ile Leu Gln Arg Val Gln Gln His Ile Glu Ser
                290                 295                 300

Lys Leu Leu Gly Ser Asn Ser Ser Arg Met Val Phe His Pro Asp Leu
305                 310                 315                 320

Ala Ser Arg Thr Cys Trp Ala Ser Gly Glu Ala Ala Arg Pro Thr Thr
                325                 330                 335

Gly Val Ala Ser Ser Thr Ser Gly Ser Gly Asp Lys Val Tyr Ala
                340                 345                 350

Tyr Gln Met Ser Arg Thr Asp Ser Arg Asp Gln Lys Leu Asp Ala Phe
                355                 360                 365
```

```
Leu Gln Pro Val Ser Ser Leu Val Pro Ser Gln Pro Gln Asp Pro Arg
    370                 375                 380

Pro Val Arg Gly Ala Arg Thr Glu Gly Ser Pro Glu Arg Ala Thr Arg
385                 390                 395                 400

Glu Asp Glu Glu Met Leu Ala Leu Pro Ala Pro Ala Glu Ala Ala Ala
                405                 410                 415

Glu Ser Glu Asn Leu Glu Arg Glu Ser Leu Met Glu Thr Ser Asp Ala
            420                 425                 430

Ala Gln Lys Ala Ala Pro Thr Ser Ser Pro Gly Ser Ser Arg Lys Ser
        435                 440                 445

His Arg Glu Asp Ser Asp Val Glu Met Val Glu Asn Ala Ser Gly Lys
    450                 455                 460

Glu Met Thr Ala Ala Cys Tyr Pro Arg Arg Ile Ile Asn Leu Thr
465                 470                 475                 480

Ser Val Leu Ser Leu Gln Glu Glu Ile Ser Glu Arg Cys His Glu Thr
                485                 490                 495

Leu Arg Glu Ile Leu Arg Asn His Ser Phe Val Gly Cys Val Asn Pro
            500                 505                 510

Gln Trp Ala Leu Ala Gln His Gln Thr Lys Leu Tyr Leu Leu Asn Thr
        515                 520                 525

Thr Lys Leu Ser Glu Glu Leu Phe Tyr Gln Ile Leu Ile Tyr Asp Phe
    530                 535                 540

Ala Asn Phe Gly Val Leu Arg Leu Ser Glu Pro Ala Pro Leu Phe Asp
545                 550                 555                 560

Leu Ala Met Leu Ala Glx Thr Val Leu Lys Val Ala Gly Gln Arg Thr
                565                 570                 575

Thr Ala Arg Arg Arg Ala Cys Arg Val His Cys Arg Val Ser Glu Glu
            580                 585                 590

Lys Arg Asp Ala Cys Arg Leu Phe Ser Val Arg Ser Met Arg Arg Glu
        595                 600                 605

Pro Asp Glx Leu Leu Phe Glx Glx Gln Leu Cys Ala Thr Phe Gly Gly
    610                 615                 620

Thr Ala Tyr Leu His Ser Ser Thr Gly His Glx Gly Glu Leu Gly Glu
625                 630                 635                 640

Glu Lys Glu Cys Phe Glu Ser Leu Ser Lys Glu Cys Ala Met Phe Tyr
                645                 650                 655

Ser Ile Arg Lys Gln Tyr Ile Leu Glu Glu Ser Thr Leu Ser Gly Gln
            660                 665                 670

Gln Ser Asp Met Pro Gly Ser Thr Ser Lys Pro Trp Lys Trp Thr Val
        675                 680                 685

Glu His Ile Ile Tyr Lys Ala Phe Arg Ser His Leu Leu Pro Pro Lys
    690                 695                 700

His Phe Thr Glu Asp Gly Asn Val Leu Gln Leu Ala Asn Leu Pro Asp
705                 710                 715                 720

Leu Tyr Lys Val Phe Glu Arg Cys
                725

(2) INFORMATION FOR SEQ ID NO:137:

(i) SEQUENCE CHARACTERISTICS:
        (A) LENGTH: 3065 base pairs
        (B) TYPE: nucleic acid
        (C) STRANDEDNESS: single
        (D) TOPOLOGY: linear (xi) SEQUENCE DESCRIPTION: SEQ ID NO:137:
```

-continued

```
CGGTGAAGGT CCTGAAGAAT TTCCAGATTC CTGAGTATCA TTGGAGGAGA CAGATAACCT      60
GTCGTCAGGT AACGATGGTG TATATGCAAC AGAAATGGGT GTTCCTGGAG ACGCGTCTTT     120
TCCCGAGAGC GGCACCGCAA CTCTCCCGCG GTGACTGTGA CTGGAGGAGT CCTGCATCCA     180
TGGAGCAAAC CGAAGGCGTG AGTACAGAAT GTGCTAAGGC CATCAAGCCT ATTGATGGGA     240
AGTCAGTCCA TCAAATTTGT TCTGGGCAGG TGATACTCAG TTTAAGCACC GCTGTGAAGG     300
AGTTGATAGA AAATAGTGTA GATGCTGGTG CTACTACTAT TGATCTAAGG CTTAAAGACT     360
ATGGGGTGGA CCTCATTGAA GTTTCAGACA ATGGATGTGG GGTAGAAGAA GAAAACTTTG     420
AAGGTCTAGC TCTGAAACAT CACACATCTA AGATTCAAGA GTTTGCCGAC CTCACGCAGG     480
TTGAAACTTT CGGCTTTCGG GGGGAAGCTC TGAGCTCTCT GTGTGCACTA AGTGATGTCA     540
CTATATCTAC CTGCCACGGG TCTGCAAGCG TTGGGACTCG ACTGGTGTTT GACCATAATG     600
GGAAAATCAC CCAGAAAACT CCCTACCCCC GACCTAAAGG AACCACAGTC AGTGTGCAGC     660
ACTTATTTTA TACACTACCC GTGCGTTACA AGAGTTTCA GAGGAACATT AAAAAGGAGT     720
ATTCCAAAAT GGTGCAGGTC TTACAGGCGT ACTGTATCAT CTCAGCAGGC GTCCGTGTAA     780
GCTGCACTAA TCAGCTCGGA CAGGGGAAGC GGCACGCTGT GGTGTGCACA AGCGGCACGT     840
CTGGCATGAA GGAAAATATC GGGTCTGTGT TTGGCCAGAA GCAGTTGCAA AGCCTCATTC     900
CTTTTGTTCA GCTGCCCCCT AGTGACGCTG TGTGTGAAGA GTACGGCCTG AGCACTTCAG     960
GACGCCACAA AACCTTTTCT ACGTTTTCGG GCTTCATTTC ACAGTGCACG CACGGCGCCG    1020
GGAGGAGTGC AACAGACAGG CAGTTTTTCT TCATCAATCA GAGGCCCTGT GACCCAGCAA    1080
AGGTCTCTAA GCTTGTCAAT GAGGTTTATC ACATGTATAA CCGGCATCAG TACCCATTTG    1140
TCGTCCTTAA CGTTTCCGTT GACTCAGAAT GTGTGGATAT TAATGTAACT CCAGATAAAA    1200
GGCAAATTCT ACTACAAGAA GAGAAGCTAT TGCTGGCCGT TTTAAAGACC TCCTTGATAG    1260
GAATGTTTGA CAGTGATGCA AACAAGCTTA ATGTCAACCA GCAGCCACTG CTAGATGTTG    1320
AAGGTAACTT AGTAAAGTCG CATACTGCAG AACTAGAAAA GCCTGTGCCA GGAAAGCAAG    1380
ATAACTCTCC TTCACTGAAG AGCACAGCAG ACGAGAAAAG GGTAGCATCC ATCTCCAGGC    1440
TGAGAGAGGC CTTTTCTCTT CATCCTACTA AAGAGATCAA GTCTAGGGGT CCAGAGACTG    1500
CTGAACTGAC ACGGAGTTTT CCAAGTGAGA AAGGGGCGT GTTATCCTCT TATCCTTCAG    1560
ACGTCATCTC TTACAGAGGC CTCCGTGGCT CGCAGGACAA ATTGGTGAGT CCCACGGACA    1620
GCCCTGGTGA CTGTATGGAC AGAGAGAAAA TAGAAAAAGA CTCAGGGCTC AGCAGCACCT    1680
CAGCTGGCTC TGAGGAAGAG TTCAGCACCC CAGAAGTGGC CAGTAGCTTT AGCAGTGACT    1740
ATAACGTGAG CTCCCTAGAA GACAGACCTT CTCAGGAAAC CATAAACTGT GGTGACCTGC    1800
TGCCGTCCTC CAGGTACAGG ACAGTCCTTG AAGCCAGAAG ACCATGGATA TCAATGCAAA    1860
GCTCTACCTC TAGCTCGTCT GTCACCCACA AATGCCAAGC GCTTCAAGAC AGAGGAAGAC    1920
CCTCAAATGT CAACATATCT CAAAGATTGC CTGGTCCTCA GAGCACCTCA GCAGCTGAGG    1980
TCGATGTAGC CATAAAAATG AATAAGAGAT CGTGCTCCTC GAGTTCTCTA GCTAAGCGAA    2040
TGAAGCAGTT ACAGCACCTA AAGGCGCAGA ACAAACATGA ACTGAGTTAC AGAAAATTTA    2100
GGGCCAAGAT TTGCCCTGGA GAAAACCAAG CAGCAGAAGA TGAACTCAGA AAAGAGATTA    2160
GTAAATCGAT GTTTGCAGAG ATGGAGATCT TGGGTCAGTT TAACCTGGGA TTTATAGTAA    2220
CCAAACTGAA AGAGGACCTC TTCCTGGTGG ACCAGCATGC TGCGGATGAG AAGTACAACT    2280
TTGAGATGCT GCAGCAGCAC ACGGTGCTCC AGGCGCAGAG GCTCATCACG TGGGTGCACA    2340
```

-continued

```
CAGGCTTCAG AGTTCCCAGA CCCCAGACTC TGAACTTAAC TGCTGTCAAT GAAGCTGTAC    2400

TGATAGAAAA TCTGGAAATA TTCAGAAAGA ATGGCTTTGA CTTTGTCATT GATGAGGATG    2460

CTCCAGTCAC TGAAAGGGCT AAATTGATTT CCTTACCAAC TAGTAAAAAC TGGACCTTTG    2520

GACCCCAAGA TATAGATGAA CTGATCTTTA TGTTAAGTGA CAGCCCTGGG GTCATGTGCC    2580

GGCCCTCACG AGTCAGACAG ATGTTTGCTT CCAGAGCCTG TCGGAAGTCA GTGATGATTG    2640

GAACGGCGCT CAATGCGAGC GAGATGAAGA AGCTCATCAC CCACATGGGT GAGATGGACC    2700

ACCCCTGGAA CTGCCCCCAC GGCAGGCCAA CCATGAGGCA CGTTGCCAAT CTGGATGTCA    2760

TCTCTCAGAA CTGACACACC CCTTGTAGCA TAGAGTTTAT TACAGATTGT TCGGTTCGCA    2820

AAGAGAAGGT TTTAAGTAAT CTGATTATCG TTGTACAAAA ATTAGCATGC TGCTTTAATG    2880

TACTGGATCC ATTTAAAAGC AGTGTTAAGG CAGGCATGAT GGAGTGTTCC TCTAGCTCAG    2940

CTACTTGGGT GATCCGGTGG GAGCTCATGT GAGCCCAGGA CTTTGAGACC ACTCCGAGCC    3000

ACATTCATGA GACTCAATTC AAGGACAAAA AAAAAAAGAT ATTTTTGAAG CCTTTTAAAA    3060

AAAAA                                                                3065
```

(2) INFORMATION FOR SEQ ID NO:138:

(i) SEQUENCE CHARACTERISTICS:
        (A) LENGTH: 864 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:138:

```
Met Glu Gln Thr Glu Gly Val Ser Thr Glu Cys Ala Lys Ala Ile Lys
 1               5                  10                  15

Pro Ile Asp Gly Lys Ser Val His Gln Ile Cys Ser Gly Gln Val Ile
            20                  25                  30

Leu Ser Leu Ser Thr Ala Val Lys Glu Leu Ile Glu Asn Ser Val Asp
        35                  40                  45

Ala Gly Ala Thr Thr Ile Asp Leu Arg Leu Lys Asp Tyr Gly Val Asp
    50                  55                  60

Leu Ile Glu Val Ser Asp Asn Gly Cys Gly Val Glu Glu Glu Asn Phe
65                  70                  75                  80

Glu Gly Leu Ala Leu Lys His His Thr Ser Lys Ile Gln Glu Phe Ala
                85                  90                  95

Asp Leu Thr Gln Val Glu Thr Phe Gly Phe Arg Gly Glu Ala Leu Ser
            100                 105                 110

Ser Leu Cys Ala Leu Ser Asp Val Thr Ile Ser Thr Cys His Gly Ser
        115                 120                 125

Ala Ser Val Gly Thr Arg Leu Val Phe Asp His Asn Gly Lys Ile Thr
    130                 135                 140

Gln Lys Thr Pro Tyr Pro Arg Pro Lys Gly Thr Thr Val Ser Val Gln
145                 150                 155                 160

His Leu Phe Tyr Thr Leu Pro Val Arg Tyr Lys Glu Phe Gln Arg Asn
                165                 170                 175

Ile Lys Lys Glu Tyr Ser Lys Met Val Gln Val Leu Gln Ala Tyr Cys
            180                 185                 190

Ile Ile Ser Ala Gly Val Arg Val Ser Cys Thr Asn Gln Leu Gly Gln
        195                 200                 205

Gly Lys Arg His Ala Val Val Cys Thr Ser Gly Thr Ser Gly Met Lys
```

-continued

```
                210                 215                 220
Glu Asn Ile Gly Ser Val Phe Gly Gln Lys Gln Leu Gln Ser Leu Ile
225                 230                 235                 240

Pro Phe Val Gln Leu Pro Pro Ser Asp Ala Val Cys Glu Glu Tyr Gly
                245                 250                 255

Leu Ser Thr Ser Gly Arg His Lys Thr Phe Ser Thr Phe Ser Gly Phe
                260                 265                 270

Ile Ser Gln Cys Thr His Gly Ala Gly Arg Ser Ala Thr Asp Arg Gln
                275                 280                 285

Phe Phe Phe Ile Asn Gln Arg Pro Cys Asp Pro Ala Lys Val Ser Lys
290                 295                 300

Leu Val Asn Glu Val Tyr His Met Tyr Asn Arg His Gln Tyr Pro Phe
305                 310                 315                 320

Val Val Leu Asn Val Ser Val Asp Ser Glu Cys Val Asp Ile Asn Val
                325                 330                 335

Thr Pro Asp Lys Arg Gln Ile Leu Leu Gln Glu Lys Leu Leu Leu
                340                 345                 350

Ala Val Leu Lys Thr Ser Leu Ile Gly Met Phe Asp Ser Asp Ala Asn
                355                 360                 365

Lys Leu Asn Val Asn Gln Gln Pro Leu Leu Asp Val Glu Gly Asn Leu
370                 375                 380

Val Lys Ser His Thr Ala Glu Leu Glu Lys Pro Val Pro Gly Lys Gln
385                 390                 395                 400

Asp Asn Ser Pro Ser Leu Lys Ser Thr Ala Asp Glu Lys Arg Val Ala
                405                 410                 415

Ser Ile Ser Arg Leu Arg Glu Ala Phe Ser Leu His Pro Thr Lys Glu
                420                 425                 430

Ile Lys Ser Arg Gly Pro Glu Thr Ala Glu Leu Thr Arg Ser Phe Pro
                435                 440                 445

Ser Glu Lys Arg Gly Val Leu Ser Ser Tyr Pro Ser Asp Val Ile Ser
                450                 455                 460

Tyr Arg Gly Leu Arg Gly Ser Gln Asp Lys Leu Val Ser Pro Thr Asp
465                 470                 475                 480

Ser Pro Gly Asp Cys Met Asp Arg Glu Lys Ile Glu Lys Asp Ser Gly
                485                 490                 495

Leu Ser Ser Thr Ser Ala Gly Ser Glu Glu Phe Ser Thr Pro Glu
                500                 505                 510

Val Ala Ser Ser Phe Ser Ser Asp Tyr Asn Val Ser Ser Leu Glu Asp
                515                 520                 525

Arg Pro Ser Gln Glu Thr Ile Asn Cys Gly Asp Leu Leu Pro Ser Ser
530                 535                 540

Arg Tyr Arg Thr Val Leu Glu Ala Arg Arg Pro Trp Ile Ser Met Gln
545                 550                 555                 560

Ser Ser Thr Ser Ser Ser Val Thr His Lys Cys Gln Ala Leu Gln
                565                 570                 575

Asp Arg Gly Arg Pro Ser Asn Val Asn Ile Ser Gln Arg Leu Pro Gly
                580                 585                 590

Pro Gln Ser Thr Ser Ala Ala Glu Val Asp Val Ala Ile Lys Met Asn
                595                 600                 605

Lys Arg Ser Cys Ser Ser Ser Leu Ala Lys Arg Met Lys Gln Leu
                610                 615                 620

Gln His Leu Lys Ala Gln Asn Lys His Glu Leu Ser Tyr Arg Lys Phe
625                 630                 635                 640
```

```
Arg Ala Lys Ile Cys Pro Gly Glu Asn Gln Ala Ala Glu Asp Glu Leu
                645                 650                 655
Arg Lys Glu Ile Ser Lys Ser Met Phe Ala Glu Met Glu Ile Leu Gly
        660                 665                 670
Gln Phe Asn Leu Gly Phe Ile Val Thr Lys Leu Lys Glu Asp Leu Phe
            675                 680                 685
Leu Val Asp Gln His Ala Ala Asp Glu Lys Tyr Asn Phe Glu Met Leu
        690                 695                 700
Gln Gln His Thr Val Leu Gln Ala Gln Arg Leu Ile Thr Trp Val His
705                 710                 715                 720
Thr Gly Phe Arg Val Pro Arg Pro Gln Thr Leu Asn Leu Thr Ala Val
                725                 730                 735
Asn Glu Ala Val Leu Ile Glu Asn Leu Glu Ile Phe Arg Lys Asn Gly
            740                 745                 750
Phe Asp Phe Val Ile Asp Glu Asp Ala Pro Val Thr Glu Arg Ala Lys
        755                 760                 765
Leu Ile Ser Leu Pro Thr Ser Lys Asn Trp Thr Phe Gly Pro Gln Asp
770                 775                 780
Ile Asp Glu Leu Ile Phe Met Leu Ser Asp Ser Pro Gly Val Met Cys
785                 790                 795                 800
Arg Pro Ser Arg Val Arg Gln Met Phe Ala Ser Arg Ala Cys Arg Lys
                805                 810                 815
Ser Val Met Ile Gly Thr Ala Leu Asn Ala Ser Glu Met Lys Lys Leu
            820                 825                 830
Ile Thr His Met Gly Glu Met Asp His Pro Trp Asn Cys Pro His Gly
        835                 840                 845
Arg Pro Thr Met Arg His Val Ala Asn Leu Asp Val Ile Ser Gln Asn
850                 855                 860
```

(2) INFORMATION FOR SEQ ID NO:139:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (xi) SEQUENCE DESCRIPTION: SEQ ID NO:139:

CTTGATTCTA GAGCYTCNCC NCKRAANCC                                          29

(2) INFORMATION FOR SEQ ID NO:140:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (xi) SEQUENCE DESCRIPTION: SEQ ID NO:140:

AGGTCGGAGC TCAARGARYT NGTNGANAA                                          29

(2) INFORMATION FOR SEQ ID NO:141:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:141:

```
ACTTGTGGAT TTTGC                                                      15

(2) INFORMATION FOR SEQ ID NO:142:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:142:

ACTTGTGAAT TTTGC                                                      15

(2) INFORMATION FOR SEQ ID NO:143:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:143:

TTCGGTGACA GATTTGTAAA TG                                              22

(2) INFORMATION FOR SEQ ID NO:144:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO:144:

TTTACGGAGC CCTGGC                                                     16

(2) INFORMATION FOR SEQ ID NO:145:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:145:

TCACCATAAA AATAGTTTCC CG                                              22

(2) INFORMATION FOR SEQ ID NO:146:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:146:

TCCTGGATCA TATTTTCTGA GC                                              22

(2) INFORMATION FOR SEQ ID NO:147:

(i) SEQUENCE CHARACTERISTICS:
        (A) LENGTH: 22 base pairs
        (B) TYPE: nucleic acid
        (C) STRANDEDNESS: single
        (D) TOPOLOGY: linear
```

```
            (xi) SEQUENCE DESCRIPTION: SEQ ID NO:147:

TTTCAGGTAT GTCCTGTTAC CC                                                  22

(2) INFORMATION FOR SEQ ID NO:148:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (xi) SEQUENCE DESCRIPTION: SEQ ID NO:148:

TGAGGCAGCT TTTAAGAAAC TC                                                  22
```

COMPOSITIONS AND METHODS RELATING TO DNA MISMATCH REPAIR GENES

CROSS-REFERENCE TO RELATED APPLICATIONS

This application is a continuation from U.S. patent application Ser. No. 08/352,902, filed Dec. 4, 1994, now U.S. Pat. No. 6,191,268 which is a continuation-in-part of U.S. patent application Ser. No. 08/209,521, filed Mar. 8, 1994, now U.S. Pat. No. 5,922,855, which is a continuation-in-part from U.S. patent application Ser. No. 08/168,877, filed Dec. 17, 1993, now abandoned. All of the above patent applications are incorporated by reference.

This invention was made with government support under Agreement No. GM 32741 and Agreement No. HG00395/GM50006 awarded by the National Institute of Health in the General Sciences Division. The government has certain rights in the invention.

FIELD OF THE INVENTION

The present invention involves DNA mismatch repair genes. In particular, the invention relates to identification of mutations and polymorphisms in DNA mismatch repair genes, to identification and characterization of DNA mismatch-repair-defective tumors, and to detection of genetic susceptibility to cancer.

BACKGROUND

In recent years, with the development of powerful cloning and amplification techniques such as the polymerase chain reaction (PCR), in combination with a rapidly accumulating body of information concerning the structure and location of numerous human genes and markers, it has become practical and advisable to collect and analyze samples of DNA or RNA from individuals who are members of families which are identified as exhibiting a high frequency of certain genetically transmitted disorders. For example, screening procedures are routinely used to screen for genes involved in sickle cell anemia, cystic fibrosis, fragile X chromosome syndrome and multiple sclerosis. For some types of disorders, early diagnosis can greatly improve the person's long-term prognosis by, for example, adopting an aggressive diagnostic routine, and/or by making life style changes if appropriate to either prevent or prepare for an anticipated problem.

Once a particular human gene mutation is identified and linked to a disease, development of screening procedures to identify high-risk individuals can be relatively straight forward. For example, after the structure and abnormal phenotypic role of the mutant gene are understood, it is possible to design primers for use in PCR to obtain amplified quantities of the gene from individuals for testing. However, initial discovery of a mutant gene, i.e., its structure, location and linkage with a known inherited health problem, requires substantial experimental effort and creative research strategies.

One approach to discovering the role of a mutant gene in causing a disease begins with clinical studies on individuals who are in families which exhibit a high frequency of the disease. In these studies, the approximate location of the disease-causing locus is determined indirectly by searching for a chromosome marker which tends to segregate with the locus. A principal limitation of this approach is that, although the approximate genomic location of the gene can be determined, it does not generally allow actual isolation or sequencing of the gene. For example, Lindblom et al.[3] reported results of linkage analysis studies performed with SSLP (simple sequence length polymorphism) markers on individuals from a family known to exhibit a high incidence of hereditary non-polyposis colon cancer (HNPCC). Lindblom et al. found a "tight linkage" between a polymorphic marker on the short arm of human chromosome 3 (3p21-23) and a disease locus apparently responsible for increasing an individual's risk of developing colon cancer. Even though 3p21-23 is a fairly specific location relative to the entire genome, it represents a huge DNA region relative to the probable size of the mutant gene. The mutant gene could be separated from the markers identifying the locus by millions of bases. At best, such linkage studies have only limited utility for screening purposes because in order to predict one person's risk, genetic analysis must be performed with tightly linked genetic markers on a number of related individuals in the family. It is often impossible to obtain such information, particularly if affected family members are deceased. Also, informative markers may not exist in the family under analysis. Without knowing the gene's structure, it is not possible to sample, amplify, sequence and determine directly whether an individual carries the mutant gene.

Another approach to discovering a disease-causing mutant gene begins with design and trial of PCR primers, based on known information about the disease, for example, theories for disease state mechanisms, related protein structures and function, possible analogous genes in humans or other species, etc. The objective is to isolate and sequence candidate normal genes which are believed to sometimes occur in mutant forms rendering an individual disease prone. This approach is highly dependent on how much is known about the disease at the molecular level, and on the investigator's ability to construct strategies and methods for finding candidate genes. Association of a mutation in a candidate gene with a disease must ultimately be demonstrated by performing tests on members of a family which exhibits a high incidence of the disease. The most direct and definitive way to confirm such linkage in family studies is to use PCR primers which are designed to amplify portions of the candidate gene in samples collected from the family members. The amplified gene products are then sequenced and compared to the normal gene structure for the purpose of finding and characterizing mutations. A given mutation is ultimately implicated by showing that affected individuals have it while unaffected individuals do not, and that the mutation causes a change in protein function which is not simply a polymorphism.

Another way to show a high probability of linkage between a candidate gene mutation and disease is by determining the chromosome location of the gene, then comparing the gene's map location to known regions of disease-linked loci such as the one identified by Lindblom et al. Coincident map location of a candidate gene in the region of a previously identified disease-linked locus may strongly implicate an association between a mutation in the candidate gene and the disease.

There are other ways to show that mutations in a gene candidate may be linked to the disease. For example, artificially produced mutant forms of the gene can be introduced into animals. Incidence of the disease in animals carrying the mutant gene can then be compared to animals with the normal genotype. Significantly elevated incidence of disease in animals with the mutant genotype, relative to animals with the wild-type gene, may support the theory that mutations in the candidate gene are sometimes responsible for occurrence of the disease.

One type of disease which has recently received much attention because of the discovery of disease-linked gene mutations is Hereditary Nonpolyposis Colon Cancer (HNPCC).[1,2] Members of HNPCC families also display increased susceptibility to other cancers including endometrial, ovarian, gastric and breast. Approximately 10% of colorectal cancers are believed to be HNPCC. Tumors from HNPCC patients display an unusual genetic defect in which short, repeated DNA sequences, such as the dinucleotide repeat sequences found in human chromosomal DNA ("microsatellite DNA"), appear to be unstable. This genomic instability of short, repeated DNA sequences, sometimes called the "RER+" phenotype, is also observed in a significant proportion of a wide variety of sporadic tumors, suggesting that many sporadic tumors may have acquired mutations that are similar (or identical) to mutations that are inherited in HNPCC.

Genetic linkage studies have identified two HNPCC loci thought to account for as much as 90% of HNPCC. The loci map to human chromosome 2p15-16 (2p21) and 3p21-23. Subsequent studies have identified human DNA mismatch repair gene hMSH2 as being the gene on chromosome 2p21, in which mutations account for a significant fraction of HNPCC cancers.[1, 2, 12] hMSH2 is one of several genes whose normal function is to identify and correct DNA mispairs including those that follow each round of chromosome replication.

The best defined mismatch repair pathway is the *E.coli* MutHLS pathway that promotes a long-patch (approximately 3 Kb) excision repair reaction which is dependent on the mutH, mutL, mutS and mutU (uvrD) gene products. The MutHLS pathway appears to be the most active mismatch repair pathway in *E.coli* and is known to both increase the fidelity of DNA replication and to act on recombination intermediates containing mispaired bases. The system has been reconstituted in vitro, and requires the mutH, mutL, mutS and uvrD (helicase II) proteins along with DNA polymerase III holoenzyme, DNA ligase, single-stranded DNA binding protein (SSB) and one of the single-stranded DNA exonucleases, Exo I, Exo VII or RecJ. hMSH2 is homologous to the bacterial mutS gene. A similar pathway in yeast includes the yeast MSH2 gene and two mutL-like genes referred to as PMS1 and MLH1.

With the knowledge that mutations in a human mutS type gene (hMSH2) sometimes cause cancer, and the discovery that HNPCC tumors exhibit microsatellite DNA instability, interest in other DNA mismatch repair genes and gene products, and their possible roles in HNPCC and/or other cancers, has intensified. It is estimated that as many as 1 in 200 individuals carry a mutation in either the hMSH2 gene or other related genes which encode for other proteins in the same DNA mismatch repair pathway.

An important objective of our work has been to identify human genes which are useful for screening and identifying individuals who are at elevated risk of developing cancer. Other objects are: to determine the sequences of exons and flanking intron sequences in such genes; to use the structural information to design testing procedures for the purpose of finding and characterizing mutations which result in an absence of or defect in a gene product which confers cancer susceptibility; and to distinguish such mutations from "harmless" polymorphic variations. Another object is to use the structural information relating to exon and flanking intron sequences of a cancer-linked gene, to diagnose tumor types and prescribe appropriate therapy. Another object is to use the structural information relating to a cancer-linked gene to identify other related candidate human genes for study.

SUMMARY OF THE INVENTION

Based on our knowledge of DNA mismatch repair mechanisms in bacteria and yeast including conservation of mismatch repair genes, we reasoned that human DNA mismatch repair homologs should exist, and that mutations in such homologs affecting protein function, would be likely to cause genetic instability, possibly leading to an increased risk of developing certain forms of human cancer.

We have isolated and sequenced two human genes, hPMS1 and hMLH1 each of which encodes for a protein involved in DNA mismatch repair. hPMS1 and hMLH1 are homologous to mutL genes found in *E.coli*. Our studies strongly support an association between mutations in DNA mismatch repair genes and susceptibility to HNPCC. Thus, DNA mismatch repair gene sequence information of the present invention, namely, cDNA and genomic structures relating to hMLH1 and hPMS1, make possible a number of useful methods relating to cancer risk determination and diagnosis. The invention also encompasses a large number of nucleotide and protein structures which are useful in such methods.

We mapped the location of hMLH1 to human chromosome 3p21-23. This is a region of the human genome that, based upon family studies, harbors a locus that predisposes individuals to HNPCC. Additionally, we have found a mutation in a conserved region of the hMLH1 cDNA in HNPCC-affected individuals from a Swedish family. The mutation is not found in unaffected individuals from the same family, nor is it a simple polymorphism. We have also found that a homologous mutation in yeast results in a defective DNA mismatch repair protein. We have also found a frameshift mutation in hMLH1 of affected individuals from an English family. Our discovery of a cancer-linked mutations in hMLH1, combined with the gene's map position which is coincident with a previously identified HNPCC-linked locus, plus the likely role of the hMLH1 gene in mutation avoidance makes the hMLH1 gene a prime candidate for underlying one form of common inherited human cancer, and a prime candidate to screen and identify individuals who have an elevated risk of developing cancer.

hMLH1 has 19 exons and 18 introns. We have determined the location of each of the 18 introns relative to hMLH1 cDNA. We have also determined the structure of all intron/exon boundary regions of hMLH1. Knowledge of the intron/exon boundary structures makes possible efficient screening regimes to locate mutations which negatively affect the structure and function of gene products. Further, we have designed complete sets of oligonucleotide primer pairs which can be used in PCR to amplify individual complete exons together with surrounding intron boundary structures.

We mapped the location of hPMS1 to human chromosome 7. Subsequent studies by others[39] have confirmed our prediction that mutations in this gene are linked to HNPCC.

The most immediate use of the present invention will be in screening tests on human individuals who are members of families which exhibit an unusually high frequency of early onset cancer, for example HNPCC. Accordingly, one aspect of the invention comprises a method of diagnosing cancer susceptibility in a subject by detecting a mutation in a mismatch repair gene or gene product in a tissue from the subject, wherein the mutation is indicative of the subject's susceptibility to cancer. In a preferred embodiment of the invention, the step of detecting comprises detecting a mutation in a human mutL homolog gene, for example, hMLH1 of hPMS1.

The method of diagnosing preferably comprises the steps of 1) amplifying a segment of the mismatch repair gene or gene product from an isolated nucleic acid; 2) comparing the amplified segment with an analogous segment of a wild-type allele of the mismatch repair gene or gene product; and 3) detecting a difference between the amplified segment and the analogous segment, the difference being indicative of a mutation in the mismatch repair gene or gene product which confers cancer susceptibility.

Another aspect of the invention provides methods of determining whether the difference between the amplified segment and the analogous wild-type segment causes an affected phenotype, i.e., does the sequence alteration affect the individual's ability to repair DNA mispairs.

The method of diagnosing may include the steps of 1) reverse transcribing all or a portion of an RNA copy of a DNA mismatch repair gene; and 2) amplifying a segment of the DNA produced by reverse transcription. An amplifying step in the present invention may comprise: selecting a pair of oligonucleotide primers capable of hybridizing to opposite strands of the mismatch repair gene, in an opposite orientation; and performing a polymerase chain reaction utilizing the oligonucleotide primers such that nucleic acid of the mismatch repair chain intervening between the primers is amplified to become the amplified segment.

In preferred embodiments of the methods summarized above, the DNA mismatch repair gene is hMLH1 or hPMS1. The segment of DNA corresponds to a unique portion of a nucleotide sequence selected from the group consisting of SEQ ID NOS: 6–24. "First stage" oligonucleotide primers selected from the group consisting of SEQ ID NOS: 44–82 are used in PCR to amplify the DNA segment. The invention also provides a method of using "second stage" nested primers (SEQ ID NOS: 83–122), for use with the first stage primers to allow more specific amplification and conservation of template DNA.

Another aspect of the present invention provides a method of identifying and classifying a DNA mismatch repair defective tumor comprising detecting in a tumor a mutation in a mismatch repair gene or gene product, preferably a mutL homolog (hMLH1 or hPMS1), the mutation being indicative of a defect in a mismatch repair system of the tumor.

The present invention also provides useful nucleotide and protein compositions. One such composition is an isolated nucleotide or protein structure including a segment sequentially corresponding to a unique portion of a human mutL homolog gene or gene product, preferably derived from either hMLH1 or hPMS1.

Other composition aspects of the invention comprise oligonucleotide primers capable of being used together in a polymerase chain reaction to amplify specifically a unique segment of a human mutL homolog gene, preferably hMLH1 or hPMS1.

Another aspect of the present invention provides a probe including a nucleotide sequence capable of binding specifically by Watson/Crick pairing to complementary bases in a portion of a human mutL homolog gene; and a label-moiety attached to the sequence, wherein the label-moiety has a property selected from the group consisting of fluorescent, radioactive and chemiluminescent.

We have also isolated and sequenced mouse MLH1 (mMLH1) and PMS1 (mPMS1) genes. We have used our knowledge of mouse mismatch repair genes to construct animal models for studying cancer. The models will be useful to identify additional oncogenes and to study environmental effects on mutagenesis.

Our knowledge of hMLH1 and hPMS1 gene sequences makes it possible to produce monoclonal and polyclonal antibodies for use in tests that detect the presence or absence of DNA mismatch repair protein in a tumor sample. Protein based testing is receiving significant attention in view of recent research showing that methylation of hMLH1 promoter DNA is the basis for DNA mismatch repair deficiency in some sporadic tumors. In this situation there is usually no detectable mutation in the hMLH1 cDNA. A screen for hMLH1 cDNA mutations would not show any abnormality. However, an immunoassay for hMLH1 protein shows absence of the protein in tumors with inactivation of the hMLH1 gene by mutation or by promotor methylation, and may be the screening test of choice for some applications. The protein structure information has been used to generate monoclonal antibodies that bind specifically to hMLH1 or hPMS1. The antibodies can be conjugated to labels such as fluorescent compounds, and then used as an immunohistochemical stain to detect DNA mismatch repair protein in a tumor sample.

In addition to diagnostic and therapeutic uses for the genes, our knowledge of hMLH1 and hPMS1 can be used to search for other genes of related function which are candidates for playing a role in certain forms of human cancer.

DESCRIPTION OF THE FIGURES

FIG. 2 is an alignment of protein sequences for mutL homologs (SEQ ID NOS: 1–3) showing two highly-conserved regions (underlined) which we used to create degenerate PCR oligonucleotides for isolating additional mutL homologs.

FIG. 3 shows the entire cDNA nucleotide sequence (SEQ ID NO: 4) for the human MLH1 gene, and the corresponding predicted amino acid sequence (SEQ ID NO: 5) for the human MLH1 protein. The underlined DNA sequences are the regions of cDNA that correspond to the degenerate PCR primers that were originally used to amplify a portion of the MLH1 gene (nucleotides 118–135 and 343–359).

FIG. 4A shows the nucleotide sequences of the 19 exons which collectively correspond to the entire hMLH1 cDNA structure. The exons are flanked by intron boundary structures. Primer sites are underlined. The exons with their flanking intron structures correspond to SEQ ID NOS: 6–24. The exons, shown in non-underlined small case letters, correspond to SEQ ID NOS: 25–43.

FIG. 4B shows nucleotide sequences of primer pairs which have been used in PCR to amplify the individual exons. The "second stage" amplification primers (SEQ ID NOS: 83–122) are "nested" primers which are used to amplify target exons from the amplification product obtained with corresponding "first stage" amplification primers (SEQ ID NOS: 44–82). The structures in FIG. 4B correspond to the structures in Tables 2 and 3.

FIG. 5 is an alignment of the predicted amino acid sequences for human and yeast (SEQ ID NOS: 5 and 123, respectively) MLH1 proteins. Amino acid identities are indicated by boxes and gaps are indicated by dashes.

FIG. 9 is an amino acid sequence alignment (SEQ ID NOS: 124–131) of the highly-conserved region of the MLH family of proteins surrounding the site of the predicted amino acid substitution. Bold type indicates the position of the predicted serine to phenylalanine amino acid substitution in affected individuals. Also highlighted are the serine or alanine residues conserved at this position in mutL-like proteins. Bullets indicate positions of highest amino acid conservation. For the MLH1 protein, the dots indicate that the sequence has not been obtained. Sequences were aligned as described below in reference to the phylogenetic tree of FIG. 6.

FIG. 10 shows the entire nucleotide sequence for hPMS1 (SEQ ID NO: 132).

FIG. 11 is an alignment of the predicted amino acid sequences for human and yeast PMS1 proteins (SEQ ID NOS: 133 and 134, respectively). Amino acid identities are indicated by boxes and gaps are indicated by dashes.

FIG. 12 is a partial nucleotide sequence from human MLH1.

FIG. 13 shows partial nucleotide sequences from human PMS1 cDNA.

FIG. 14 is a partial nucleotide seqquence from human MLH1.

FIG. 15 is a partial nucleotide sequence from human PMS1.

Figure 1:
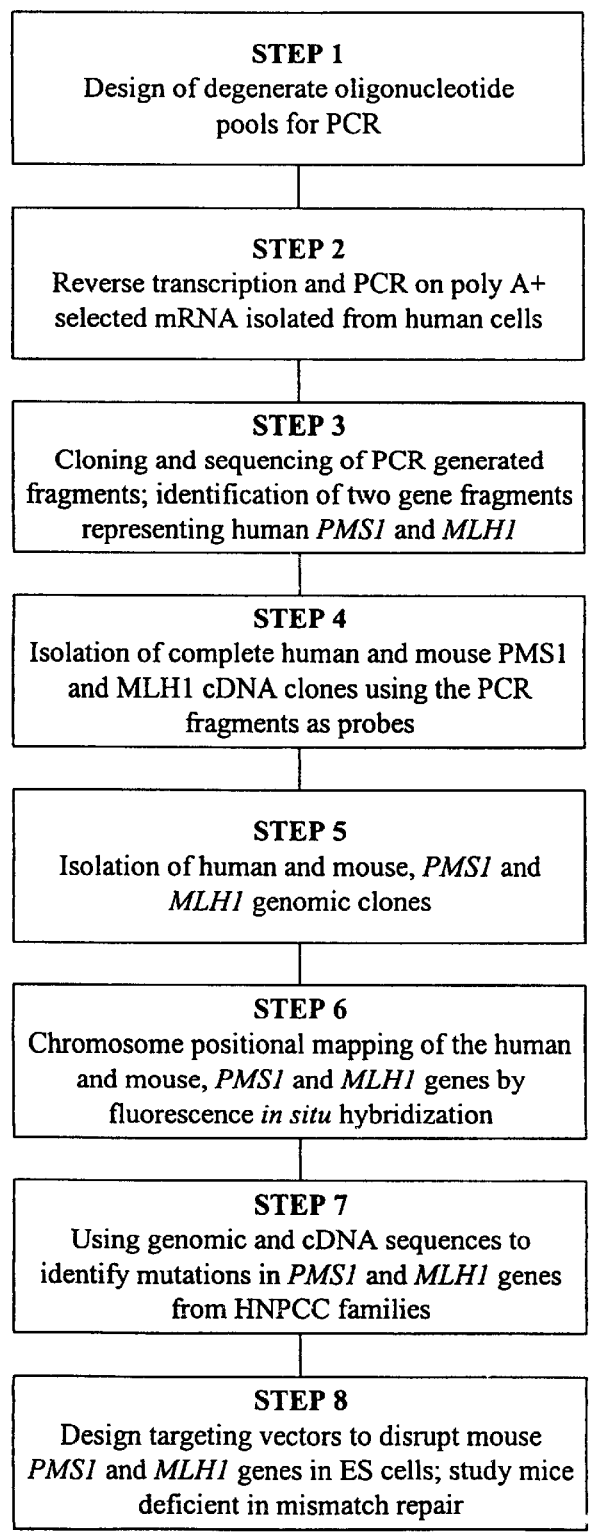
FIG. 1 is a flow chart showing an overview of the sequence of experimental steps we used to isolate, characterize and use human and mouse PMS1 and MLH1 genes.

DEFINITIONS gene—"Gene" means a nucleotide sequence that contains a complete coding sequence. Generally, "genes" also include nucleotide sequences found upstream (e.g. promoter sequences, enhancers, etc.) or downstream (e.g. transcription termination signals, polyadenylation sites, etc.) of the coding sequence that affect the expression of the encoded polypeptide.
gene product—A "gene product" is either a DNA or RNA (mRNA) copy of a portion of a gene, or a corresponding amino acid sequence translated from mRNA.
wild-type—The term "wild-type", when applied to nucleic acids and proteins of the present invention, means a version of a nucleic acid or protein that functions in a manner indistinguishable from a naturally-occurring, normal version of that nucleic acid or protein (i.e. a nucleic acid or protein with wild-type activity). For example, a "wild-type" allele of a mismatch repair gene is capable of functionally replacing a normal, endogenous copy of the same gene within a host cell without detectably altering mismatch repair in that cell. Different wild-type versions of the same nucleic acid or protein may or may not differ structurally from each other.
non-wild-type—The term "non-wild-type" when applied to nucleic acids and proteins of the present invention, means a version of a nucleic acid or protein that functions in a manner distinguishable from a naturally occurring, normal version of that nucleic acid or protein. Non-wild-type alleles of a nucleic acid of the invention may differ structurally from wild-type alleles of the same nucleic acid in any of a variety of ways including, but not limited to, differences in the amino acid sequence of an encoded polypeptide and/or differences in expression levels of an encoded nucleotide transcript of polypeptide product.

For example, the nucleotide sequence of a non-wild-type allele of a nucleic acid of the invention may differ from that of a wild-type allele by, for example, addition, deletion, substitution, and/or rearrangement of nucleotides. Similarly, the amino acid sequence of a non-wild-type mismatch repair protein may differ from that of a wild-type mismatch repair protein by, for example, addition, substitution, and/or rearrangement of amino acids.

Particular non-wild-type nucleic acids or proteins that, when introduced into a normal host cell, interfere with the endogenous mismatch repair pathway, are termed "dominant negative" nucleic acids or proteins.
homologous—The term "homologous" refers to nucleic acids or polypeptides that are highly related at the level of nucleotide or amino acid sequence. Nucleic acids or polypeptides that are homologous to each other are termed "homologues".

The term "homologous" necessarily refers to a comparison between two sequences. In accordance with the invention, two nucleotide sequences are considered to be homologous if the polypeptides they encode are at least about 50–60% identical, preferably about 70% identical, for at least one stretch of at least 20 amino acids. Preferably, homologous nucleotide sequences are also characterized by the ability to encode a stretch of at least 4–5 uniquely specified amino acids. Both the identity and the approximate spacing of these amino acids relative to one another must be considered for nucleotide sequences to be considered to be homologous. For nucleotide sequences less than 60 nucleotides in length, homolog is determined by the ability to encode a stretch of at least 4–5 uniquely specified amino acids.
upstream/downstream—The terms "upstream" and "downstream" are art-understood terms referring to the position of an element of nucleotide sequence. "Upstream" signifies an element that is more 5' than the reference element. "Downstream" refers to an element that is more 3' than a reference element.
intron/exon—The terms "exon" and "intron" are art-understood terms referring to various portions of genomic gene sequences. "Exons" are those portions of a genomic gene sequence that encode protein. "Introns" are sequences of nucleotides found between exons in genomic gene sequences.
affected—The term "affected", as used herein, refers to those members of a kindred that either have developed a characteristic cancer (e.g. colon cancer in an HNPCC lineage) and/or are predicted, on the basis of, for example, genetic studies, to carry an inherited mutation that confers susceptibility to cancer.
unique—A "unique" segment, fragment or portion of a gene or protein means a portion of a gene or protein which is different sequentially from any other gene or protein segment in an individual's genome. As a practical matter, a unique segment or fragment of a gene will typically be a nucleotide of at least about 13 bases in length and will be sufficiently different from other gene segments so that oligonucleotide primers may be designed and used to selectively and specifically amplify the segment. A unique segment of a protein is typically an amino acid sequence which can be translated from a unique segment of a gene.

References

The following publications are referred to by number in the text of the application. Each of the publications is incorporated here by reference.

1. Fishel, R., et al. Cell 75, 1027–1038 (1993).
2. Leach, F., et al. Cell 75, 1215–1225 (1993).
3. Lindblom, A., Tannergard, Pl, Werelius, B. & Nordenskjold, M. Nature Genetics 5, 279–282 (1993).
4. Prolla, T. A, Christie, D. M. & Liskay, R. M. Molec. and Cell. Biol. 14, 407–415 (1994).
5. Strand, M. Prolla, T. A., Liskay, R. M. & Petes, T. D. Nature 365, 274–276 (1993).
6. Aaltonen, L. A., et al. Science 260, 812–816 (1993).
7. Han, H. J., Yanagisawa, A., Kato, Y., Park, J. G. & Nakamura, Y. Cancer 53, 5087–5089 (1993).
8. Ionov, Y., Peinado, M. A., Malkhosyan, S., Shibata, D. & Perucho, M. Nature 363, 558–561(1993).
9. Risinger, J. I. et al. Cancer 53, 5100–5103 (1993).
10. Thibodeau, S. N., Bren, G. & Shaid, D. Science 260, 816–819 (1993).
11. Levinson, G. & Gutman, G. A. Nucleic Acids Res. 15, 5323–5338 (1987).
12. Parsons, R, et al. Cell 75, 1227–1236 (1993).
13. Modrich, P. Ann. Rev. of Genet. 25, 229–53 (1991).
14. Reenan, R. A. & Kolodner, R. D. Genetics 132, 963–73 (1992).
15. Bishop, D. K., Anderson, J. & Kolodner, R. D. PNAS 86, 3713–3717 (1989).
16. Kramer, W., Kramer, B., Williamson, M. S. & Fogel, S. J. Bacteriol. 171, 5339–5346 (1989).
17. Williamson, M. S., Game, J. C. & Fogel, S., Genetics 110, 609–646 (1985).
18. Prudhomme, M., Martin, B., Mejean, V. & Claverys, J. J. Bacteriol. 171, 5332–5338 (1989).
19. Mankovich, J. A., McIntyre, C. A. & Walker, G. C. J Bacteriol. 171, 5325–5331 (1989).
20. Lichter, P., et al. Science 247, 64–69 (1990).
21. Boyle, A., Feltquite, D. M., Dracopoli, N., Housman, D. & Ward, D. C. Genornics 12, 106–115 (1992).
22. Lyon, M. F. & Kirby, M. C., Mouse Genome 91,40–80 (1993).
23. Reenan, R. A. & Kolodner, R. D. Genetics 132,975–85 (1992).
24. Latif, F. et al. Cancer Research 52, 1451–1456 (1992).
25. Naylor, S. L., Johnson, B. E., Minna, J. D. & Sakaguchi, A. Y. Nature 329, 451–454 (1987).
26. Ali, L. U., Lidereau, R. & Callahan, R. Journal of the National Cancer Institute 81, 1815–1820 (1989).
27. Higgins, D., Bleasby, A. & Fuchs, R. Comput. Apple Biosci. 8, 189–191 (1992).
28. Fields, S. & Song, O. K. Nature 340, 245–246 (1989).
29. Lynch, H. T., et al. Gastroenterology 104, 1535–1549 (1993).
30. Elledge, S. J., Mulligan, J. T., Ramer, S. W., Spottswood, M. & Davis, R. W. Proc. Natl. Acad. Sci. U.S.A. 88, 1731–1735 (1991).
31. Frohman, M. Amplifications, a forum for PCR users 1, 11–15 (1990).
32. Powell, S. M., et al. New England Journal of Medicine 329, 1982–1987 (1993).
33. Wu, D. Y., Nozari, G. Schold, M., Conner, B. J. & Wallace, R. B. DNA 8, 135–142 (1989).
34. Mullis, K. E. B. & Faloona, F. A. Methods in Enzymology 155, 335–350 (1987).
35. Bishop, T. D., Thomas, H. Cancer Sur. 9, 585–604 (1990).
36. Capecchi, M. R. Scientific American 52–59 (March 1994).
37. Erlich, H. A. PCR Technology, Principles and Applications for DNA Amplification (1989).
38. Papadopoulos et al. Science 263, 1625–1629 (March 1994).
39. Nicolaides et al. Nature 371, 75–80 (September 1994).
40. Tong et al. Anal. Chem. 64, 2672–2677 (1992).
41. Debuire et al. Clin. Chem. 39, 1682–5 (1993).
42. Wahlberg et al. Electrophoresis 13, 547–551 (1992).
43. Kaneoka et al. Biotechniques 10, 30, 32, 34 (1991).
44. Huhman et al. Biotechniques 10, 84–93 (1991).
45. Hultman et al. Nuc. Acid. Res. 17,493746(1989).
46. Zu et al. Mutn. Res. 288, 232–248 (1993).
47. Espelund et al. Biotechniques 13, 74–81 (1992).
48. Prolla et al. Science 265, 1091–1093 (1994).
49. Bishop et al. Mol. Cell. Biol. 6, 3401–3409 (1986).
50. Folger et al. Mol. Cell. Biol. 5, 70–74 (1985).
51. T. C. Brown et al. Cell 54, 705–711 (1988).
52. T. C. Brown et al. Genome 31, 578–583 (1989).
53. C. Muster-Nassal et al. Proc. Natl. Acad. Sci. U.S.A. 83, 7618–7622 (1986).
54. I. Varlet et al. Proc. Natl. Acad. Sci. U.S.A. 87, 7883–7887 (1990).
55. D. C. Thomas et al. J. Biol. Chem. 266, 3744–3751 (1991).
56. J. J. Holmes et al. Proc. Natl. Acad. Sci. U.S.A. 87, 5837–5841 (1990).
57. P. Branch et al. Nature 362, 652–654 (1993).
58. A. Kat et al. Proc. Natl. Acad. Sci. U.S.A. 90, 6424–6428 (1993).
59. K. Wiebauer et al. Nature 339, 234–236 (1989).
60. K. Wiebauer et al. Proc. Natl. Acad. Sci. U.S.A. 87, 5842–5845 (1990).
61. P. Neddermann et al. J. Biol. Chem. 268, 21218–24 (1993).
62. Kramer et al. Mol. Cell Biol. 9:4432–40 (1989).
63. Kramer et al. J. Bacteriol. 171:5339–5346 (1989).
64. Herman et al. Proc. Natl. Acad. Sci. U.S.A. 95 (12): 6870–6875 (June 1998).
65. Kane et al. Cancer Res. 57 (5): 808–811 (March 1997).

DESCRIPTION OF THE INVENTION

We have discovered mammalian genes which are involved in DNA mismatch repair. One of the genes, hPMS1, encodes a protein which is homologous to the yeast DNA mismatch repair protein PMS1. We have mapped the locations of hPMS1 to human chromosome 7 and the mouse PMS1 gene to mouse chromosome 5, band G. Another gene, hMLH1 (MutL Homolog) encodes a protein which is homologous to the yeast DNA mismatch repair protein MLH1. We have mapped the locations of hMLH1 to human chromosome 3p21.3-23 and to mouse chromosome 9, band E.

Studies[1,2] have demonstrated involvement of a human DNA mismatch repair gene homolog, hMSH2, on chromosome 2p in HNPCC. Based upon linkage data, a second HNPCC locus has been assigned to chromosome 3p21-23.[3] Examination of tumor DNA from the chromosome 3-linked kindreds revealed dinucleotide repeat instability similar to that observed for other HNPCC families[6] and several types of sporadic tumors.[7-10] Because dinucleotide repeat instability is characteristic of a defect in DNA mismatch repair,[5, 11, 12] we reasoned that HNPCC linked to chromosome 3p21-23 could result from a mutation in a second DNA mismatch repair gene.

Repair of mismatched DNA in *Escherichia coli* requires a number of genes including mutS, mutL and mutH, defects in any one of which result in elevated spontaneous mutation rates.[13] Genetic analysis in the yeast *Saccharomyces cerevisiae* has identified three DNA mismatch repair genes: a mutS homolog, MSH2,[14] and two mutL homologs, PMS1[16] and MLH1.[4] Each of these three genes play an indispensable role in DNA replication fidelity, including the stabilization of dinucleotide repeats.[5]

We believe that hMLH1 is the HNPCC gene previously linked to chromosome 3p based upon the similarity of the hMLH1 gene product to the yeast DNA mismatch repair protein, MLH1,[4] the coincident location of the hMLH1 gene and the HNPCC locus on chromosome 3, and hMLH1 missense mutations which we found in affected individuals from chromosome 3-linked HNPCC families.

Our knowledge of the human and mouse MLH1 and PMS1 gene structures has many important uses. The gene sequence information can be used to screen individuals for cancer risk. Knowledge of the gene structures makes it possible to easily design PCR primers which can be used to selectively amplify portions of hMLH1 and hPMS1 genes for subsequent comparison to the normal sequence and cancer risk analysis. This type of testing also makes it possible to search for and characterize hMLH1 and hPMS1 cancer-linked mutations for the purpose of eventually focusing the cancer screening effort on specific gene loci. Specific characterization of cancer-linked mutations in hMLH1 and hPMS1 makes possible the production of other valuable diagnostic tools such as allele specific probes which may be used in screening tests to determine the presence or absence of specific gene mutations.

Additionally, the gene sequence information for hMLH1 and/or hPMS1 can be used, for example, in a two hybrid system, to search for other genes of related function which are candidates for cancer involvement.

The hMLH1 and hPMS1 gene structures are useful for making proteins which are used to develop antibodies directed to specific portions or the complete hMLH1 and hPMS1 proteins. Such antibodies can then be used to isolate the corresponding protein and possibly related proteins for research and diagnostic purposes.

The mouse MLH1 and PMS1 gene sequences are useful for producing mice that have mutations in the respective gene. The mutant mice are useful for studying the gene's function, particularly its relationship to cancer.

Methods for Isolating and Characterizing Mammalian MLH1 and PMS1 Genes

We have isolated and characterized four mammalian genes, i.e., human MLH1 (hMLH1), human PMS1 (hPMS1), mouse MLH1 (mPMS1) and mouse PMS1 (mPMS1). Due to the structural similarity between these genes, the methods we have employed to isolate and characterize them are generally the same. FIG. 1 shows in broad terms, the experimental approach which we used to isolate and characterize the four genes. The following discussion refers to the step-by-step procedure shown in FIG. 1.

Step 1 Design of Degenerate Oligonucleotide Pools for PCR

Earlier reports indicated that portions of three mutL-like proteins, two from bacteria, mutL and HexB, and one from yeast, PMS1 are highly conserved.[16,18,19] After inspection of the amino acid sequences of HexB, mutL and PMS1 proteins, as shown in FIG. 2, we designed pools of degenerate oligonucleotide pairs corresponding to two highly-conserved regions, KELVEN and GFRGEA, of the mutL-like proteins. The sequences (SEQ ID NOS: 139 and 140, respectively) of the degenerate oligonucleotides which we used to isolate the four genes are:

5'-CTTGAT<u>TCTAGA</u>GC(T/C)TCNCCNC(T/G)(A/G)A ANCC-3' and

5'-AGGTCG<u>GAGCTC</u>AA(A/G)GA(A/G)(T/C)TNGTN GANAA-3'.

The underlined sequences within the primers are XbaI and SacI restriction endonuclease sites respectively. They were introduced in order to facilitate the cloning of the PCR-amplified fragments. In the design of the oligonucleotides, we took into account the fact that a given amino acid can be coded for by more than one DNA triplet (codon). The degeneracy within these sequences are indicated by multiple nucleotides within parentheses or N, for the presence of any base at that position.

Step 2 Reverse Transcription and PCR on Poly A+ Selected mRNA Isolated from Human Cells We isolated messenger (poly A+ enriched) RNA from cultured human cells, synthesized double-stranded cDNA from the mRNA, and performed PCR with the degenerate oligonucleotides.[4] After trying a number of different PCR conditions, for example, adjusting the annealing temperature, we successfully amplified a DNA of the size predicted (~210 bp) for a mutL-like protein.

Step 3 Cloning and Sequencing of PCR-generated Fragments; Identification of Two Gene Fragments Representing Human PMS1 and MLH1

We isolated the PCR amplified material (~210 bp) from an agarose gel and cloned this material into a plasmid (pUC19). We determined the DNA sequence of several different clones. The amino acid sequence inferred from the DNA sequence of two clones showed strong similarity to other known mutL-like proteins.[4,16,18,19] The predicted amino acid sequence for one of the clones was most similar to the yeast PMS1 protein. Therefore we named it hPMS1, for human PMS1. The second clone was found to encode a polypeptide that most closely resembles yeast MLH1 protein and was named, hMLH1, for human MLH1.

Step 4 Isolation of Complete Human and Mouse PMS1 and MLH1 cDNA Clones Using the PCR Fragments as Probes We used the 210 bp PCR-generated fragments of the hMLH1 and hPMS1 cDNAs, as probes to screen both human and mouse cDNA libraries (from Stratagene, or as described in reference 30). A number of cDNAs were isolated that corresponded to these two genes. Many of the cDNAs were truncated at the 5' end. Where necessary, PCR techniques[31] were used to obtain the 5'-end of the gene in addition to further screening of cDNA libraries. Complete composite cDNA sequences were used to predict the amino acid sequence of the human and mouse, MLH1 and PMS1 proteins.

Step 5 Isolation of Human and Mouse, PMS1 and MLH1 Genomic Clones

Information on genomic and cDNA structure of the human MLH1 and PMS1 genes are necessary in order to thoroughly screen for mutations in cancer prone families. We have used human cDNA sequences as probes to isolate the genomic sequences of human PMS1 and MLH1. We have isolated four cosmids and two P1 clones for hPMS1, that together are likely to contain most, if not all, of the cDNA (exon) sequence. For hMLH1 we have isolated four overlapping-phage clones containing 5'-MLH1 genomic sequences and four P1 clones (two full length clones and two which include the 5' coding end plus portions of the promoter region) P1 clone. PCR analysis using pairs of oligonucleotides specific to the 5' and 3' ends of the hMLH1 cDNA, clearly indicates that the P1 clone contains the complete hMLH1 cDNA information. Similarly, genomic clones for mouse PMS1 and MLH1 genes have been isolated and partially characterized (described in Step 8).

Step 6 Chromosome Positional Mapping of the Human and Mouse, PMS1 and MLH1 Genes by Fluorescence in situ Hybridization We used genomic clones isolated from human and mouse PMS1 and MLH1 for chromosomal localization by fluorescence in situ hybridization (FISH).[20,21] We mapped the human MLH1 gene to chromosome 3p21.3-23, shown in FIG. 7 as discussed in more detail below. We mapped the mouse MLH1 gene to chromosome 9 band E, a region of synteny between mouse and human.[22] In addition to FISH techniques, we used PCR with a pair of hMLH1-specific oligonucleotides to analyze DNA from a rodent/human somatic cell hybrid mapping panel (Coriell Institute for Medial Research, Camden, N.J.). Our PCR results with the panel clearly indicate that hMLH1 maps to chromosome 3. The position of hMLH1 3p21.3-23 is coincident to a region known to harbor a second locus for HNPCC based upon linkage data.

We mapped the hPMS1 gene, as shown in FIG. 12, to the long (q) arm of chromosome 7 (either 7q11 or 7q22) and the mouse PMS1 to chromosome 5 band G, two regions of synteny between the human and the mouse.[22] We performed PCR using oligonucleotides specific to hPMS1 on DNA from a rodent/human cell panel. In agreement with the FISH data, the location of hPMS1 was confirmed to be on chromosome 7. These observations assure us that our human map position for hPMS1 to chromosome 7 is correct. The physical localization of hPMS1 is useful for the purpose of identifying families which may potentially have a cancer linked mutation in hPMS1.

Step 7 Using Genomic and cDNA Sequences to Identify Mutations in hPMS1 and hMLH1 Genes from HNPCC Families We have analyzed samples collected from individuals in HNPCC families for the purpose of identifying mutations in hPMS1 or hMLH1 genes. Our approach is to design PCR primers based on our knowledge of the gene structures, to obtain exon/intron segments which we can compare to the known normal sequences. We refer to this approach as an "exon-screening".

Using cDNA sequence information we have designed and are continuing to design hPMS1 and hMLH1 specific oligonucleotides to delineate exon/intron boundaries within genomic sequences. The hPMS1 and hMLH1 specific oligonucleotides were used to probe genomic clones for the presence of exons containing that sequence. Oligonucleotides that hybridized were used as primers for DNA sequencing from the genomic clones. Exon-intron junctions were identified by comparing genomic with cDNA sequences.

Amplification of specific exons from genomic DNA by PCR and sequencing of the products is one method to screen HNPCC families for mutations.[1,2] We have identified genomic clones containing hMLH1 cDNA information and have determined the structures of all intron/exon boundary regions which flanks the 19 exons of HMCH1.

We have used the exon-screening approach to examine the MLH1 gene of individuals from HNPCC families showing linkage to chromosome 3.[3] As will be discussed in more detail below, we identified a mutation in the MLH1 gene of one such family, consisting of a C to T substitution. We predict that the C to T mutation causes a serine to phenylalanine substitution in a highly-conserved region of the protein. We are continuing to identify HNPCC families from whom we can obtain samples in order to find additional mutations in hMLH1 and hPMS1 genes.

We are also using a second approach to identify mutations in hPMS1 and hMLH1. The approach is to design hPMS1 or hMLH1 specific oligonucleotide primers to produce first-strand cDNA by reverse transcription off RNA. PCR using gene-specific primers will allow us to amplify specific regions from these genes. DNA sequencing of the amplified fragments will allow us to detect mutations.

Step 8 Design Targeting Vectors to Disrupt Mouse PMS1 and MLH1 Genes in ES Cells; Study Mice Deficient in Mismatch Repair.

We constructed a gene targeting vector based on our knowledge of the genomic mouse PMS1 DNA structure. We used the vector to disrupt the PMS1 gene in mouse embryonic stem cells.[36] The cells were injected into mouse blastocysts which developed into mice that are chimeric (mixtures) for cells carrying the PMS1 mutation. The chimeric animals will be used to breed mice that are heterozygous and homozygous for the PMS1 mutation. These mice will be useful for studying the role of the PMS1 gene in the whole organism.

Human MLH1

The following discussion is a more detailed explanation of our experimental work relating to hMLH1. As mentioned above, to clone mammalian MLH genes, we used PCR techniques like those used to identify the yeast MSH1, MSH2 and MLH1 genes and the human MSH2 gene.[1,2,4,14] As template in the PCR, we used double-stranded cDNA synthesized from poly (A+) enriched RNA prepared from cultured primary human fibroblasts. The degenerate oligonucleotides were targeted at the N-terminal amino acid sequences KELVEN and GFRGEA (see FIG. 3), two of the most conserved regions of the mutL family of proteins previously described for bacteria and yeast.[16,18,19] Two PCR products of the predicted size were identified, cloned and shown to encode a predicted amino acid sequence with homolog to mutL-like proteins. These two fragments generated by PCR were used to isolate human cDNA and genomic DNA clones.

The oligonucleotide primers which we used to amplify human mutL-related sequences were 5'-CTTGATTCTA GAGC(T/C)TCNCCNC(T/G)(A/G)AANCC-3' (SEQ ID NO: 139) and 5'-AGGTCGGAGCTCAA(A/G)GA(A/G)(T/C)TNGTNGANAA-3' (SEQ ID NO: 140). PCR was carried out in 50 μL reactions containing cDNA template, 1.0 μM each primer, 5 IU of Taq polymerase (C) 50 mM KCl, 10 mM Tris buffer pH 7.5 and 1.5 mM MgCl. PCR was carried out for 35 cycles of 1 minute at 94 C , 1 minute at 43 C and 1.5 minutes at 62 C . Fragments of the expected size, approximately 212 bp, were cloned into pUC19 and sequenced. The cloned MLH1 PCR products were labeled with a random primer labeling kit (RadPrime, Gibco BRL) and used to probe human cDNA and genomic cosmid libraries by standard procedures. DNA sequencing of double-stranded plasmid DNAs was performed as previously described.[1]

The hMLH1 cDNA nucleotide sequence as shown in FIG. 3 encodes an open reading frame of 2268 bp. Also shown in FIG. 3 is the predicted protein sequence encoded for by the hMLH1 cDNA. The underlined DNA sequences are the regions of cDNA that correspond to the degenerate PCR primers that were originally used to amplify a portion of the MLH1 gene (nucleotides 118–135 and 343–359).

FIG. 4A shows 19 nucleotide sequences corresponding to portions of hMLH1. Each sequence includes one of the 19 exons, in its entirety, surrounded by flanking intron sequences. Target PCR primer cites are underlined. More details relating to the derivation and uses of the sequences shown in FIG. 4A, are set forth below.

Figure 5:
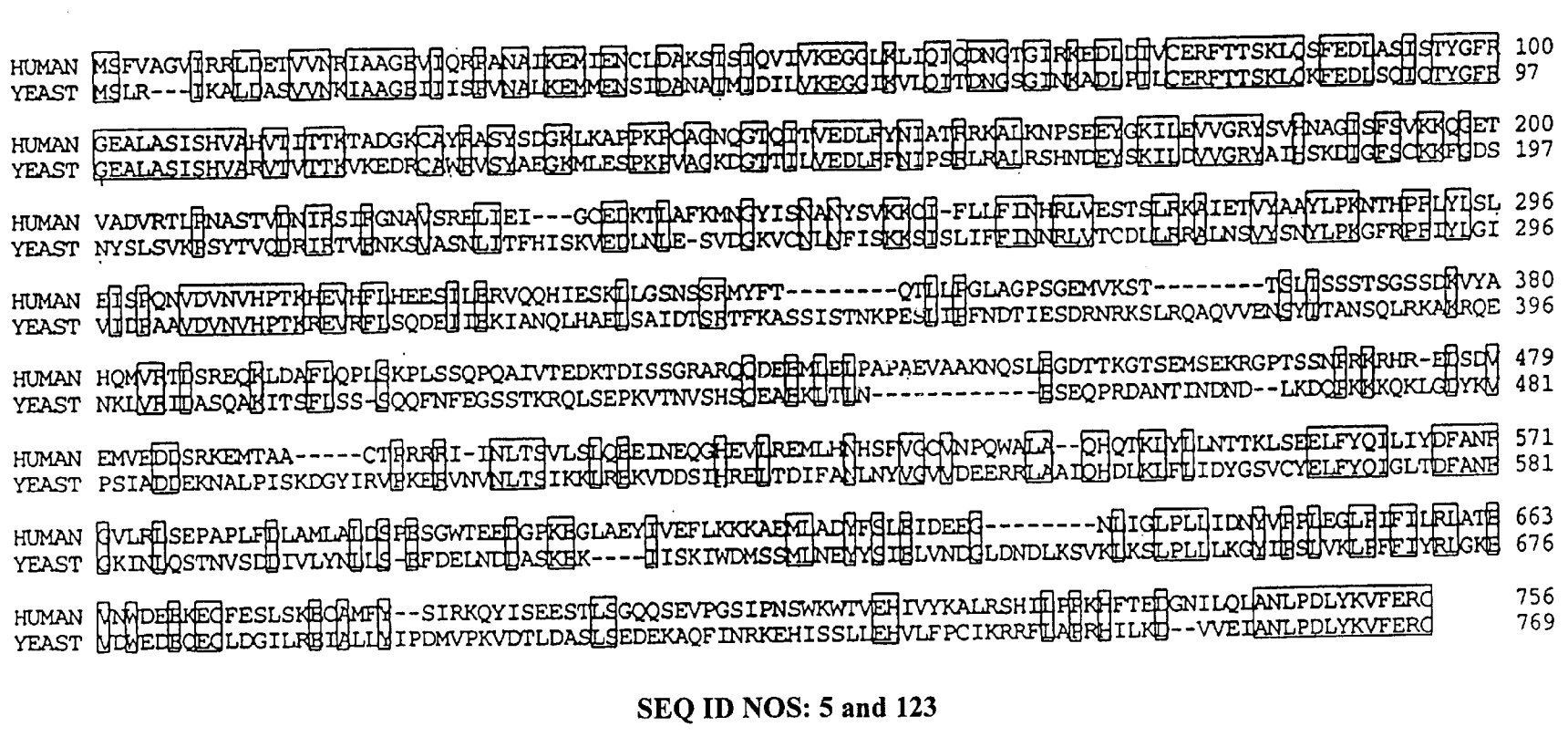

As shown in FIG. 5, the hMLH1 protein is comprised of 756 amino acids and shares 41% identity with the protein product of the yeast DNA mismatch repair gene, MLH1.[4] The regions of the hMLH1 protein most similar to yeast MLH1 correspond to amino acids 11 through 317, showing 55% identity, and the last 13 amino acids which are identical between the two proteins. FIG. 5 shows an alignment of the predicted human MLH1 and *S. cerevisiae* MLH1 protein sequences. Amino acid identities are indicated by boxes, and gaps are indicated by dashes. The pair wise protein sequence alignment was performed with DNAStar MegAlign using the clustal method.[27] Pair wise alignment parameters were a ktuple of 1, gap penalty of 3, window of 5 and diagonals of 5. Furthermore, as shown in FIG. 13, the predicted amino acid sequences of the human and mouse MLH1 proteins show at least 74% identity.

Figure 6:
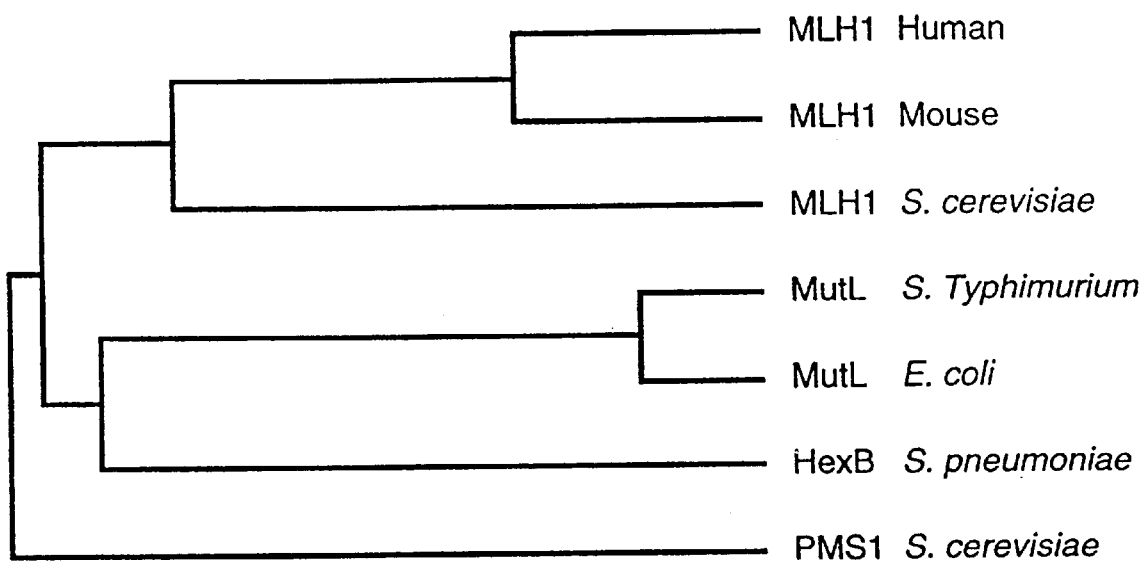
FIG. 6 is a phylogenetic tree of mutL-related proteins.

FIG. 6 shows a phylogenetic tree of mutL-related proteins. The phylogenetic tree was constructed using the predicted amino acid sequences of 7 mutL-related proteins: human MLH1; mouse MLH1; *S. cerevisiae* MLH1; *S. cerevisiae* PMS1; *E. coli*; mutL; *S. typhimurium* mutL and *S. pneumoniae* HexB. Required sequences were obtained from GenBank release 7.3. The phylogenetic tree was generated with the PILEUP program of the Genetics Computer Group software using a gap penalty of 3 and a length penalty of 0.1. The recorded DNA sequences of hMLH1 and hPMS1 have been submitted to GenBank.

hMLH1 Intron Location and Intron/Exon Boundary Structures

In our previous U.S. patent application Ser. No. 08/209,521, we described the nucleotide sequence of a complimentary DNA (cDNA) clone of a human gene, hMLH1. The cDNA sequence of hMLH1 (SEQ ID NO: 4) is presented in this application in FIG. 3. We note that there may be some variability between individuals hMLH1 cDNA structures, resulting from polymorphisms within the human population, and the degeneracy of the genetic code.

In the present application, we report the results of our genomic sequencing studies. Specifically, we have cloned the human genomic region that includes the hMLH1 gene, with specific focus on individual exons and surrounding intron/exon boundary structures. Toward the ultimate goal of designing a comprehensive and efficient approach to identify and characterize mutations which confer susceptibility to cancer, we believe it is important to know the wild-type sequences of intron structures which flank exons in the hMLH1 gene. One advantage of knowing the sequence of introns near the exon boundaries, is that it makes it possible to design primer pairs for selectively amplifying entire individual exons. More importantly, it is also possible that a mutation in an intron region, which, for example, may cause a mRNA splicing error, could result in a defective gene product, i.e., susceptibility to cancer, without showing any abnormality in an exon region of the gene. We believe a comprehensive screening approach requires searching for mutations, not only in the exon or cDNA, but also in the intron structures which flank the exon boundaries.

We have cloned the human genomic region that includes hMLH1 using approaches which are known in the art, and other known approaches could have been used. We used PCR to screen a P1 human genomic library for the hMLH1 gene. We obtained four clones, two that contained the whole gene and two which lacked the C-terminus. We characterized one of the fill length clones by cycle sequencing, which resulted in our definition of all intron/exon junction sequences for both sides of the 19 hMLH1 exons. We then designed multiple sets of PCR primers to amplify each individual exon (first stage primers) and verified the sequence of each exon and flanking intron sequence by amplifying several different genomic DNA samples and sequencing the resulting fragments using an ABI 373 sequencer. In addition, we have determined the sizes of each hMLH1 exon using PCR methods. Finally, we devised a set of nested PCR primers (second stage primers) for reamplification of individual exons. We have used the second stage primers in a multi-plex method for analyzing HNPCC families and tumors for hMLH1 mutations. Generally, in the nested PCR primer approach, we perform a first multi-plex amplification with four to eight sets of "first stage" primers, each directed to a different exon. We then reamplify individual exons from the product of the first amplification step, using a single set of second stage primers. Examples and further details relating to our use of the first and second stage primers are set forth below.

Through our genomic sequencing studies, we have identified all nineteen exons within the hMLH1 gene, and have mapped the intron/exon boundaries. One aspect of the invention, therefore, is the individual exons of the hMLH1 gene. Table 1 presents the nucleotide coordinates (i.e., the point of insertion of each intron within the coding region of the gene) of the hMLH1 exons (SEQ ID NOS: 25–43). The presented coordinates are based on the hMLH1 cDNA sequence, assigning position "1" to the "A" of the start "ATG" (which A is nucleotide 1 in SEQ ID NO: 4.

TABLE 1

| Intron Number | cDNA Sequence Coordinates |
| --- | --- |
| intron 1 | 116 & 117 |
| intron 2 | 207 & 208 |
| intron 3 | 306 & 307 |
| intron 4 | 380 & 381 |
| intron 5 | 453 & 454 |
| intron 6 | 545 & 546 |
| intron 7 | 592 & 593 |
| intron 8 | 677 & 678 |
| intron 9 | 790 & 791 |
| intron 10 | 884 & 885 |
| intron 11 | 1038 & 1039 |
| intron 12 | 1409 & 1410 |
| intron 13 | 1558 & 1559 |
| intron 14 | 1667 & 1668 |
| intron 15 | 1731 & 1732 |
| intron 16 | 1896 & 1897 |
| intron 17 | 1989 & 1990 |
| intron 18 | 2103 & 2104 |

We have also determined the nucleotide sequence of intron regions which flank exons of the hMLH1 gene. SEQ ID NOS: 6–24 are individual exon sequences bounded by their respective upstream and downstream intron sequences. The same nucleotide structures are shown in FIG. 4A, the exons are numbered from N-terminus to C-terminus with respect to the chromosomal locus. The 5-digit numbers indicate the primers used to amplify the exon. All sequences are numbered assuming the A of the ATG codon is nucleotide 1. The numbers in ( ) are the nucleotide coordinates of the coding sequence found in the indicated exon. Uppercase is intron. Lowercase is exon or non-translated sequences found in the mRNA/cDNA clone. Lowercase and underlined sequences correspond to primers. The stop codon at 2269–2271 is in italics and underlined.

Table 2 presents the sequences of primer pairs ("first stage" primers) which we have to amplify individual exons together with flanking intron structures.

TABLE 2

| EXON NO. | PRIMER LOCATION | PRIMER NO. | PRIMER SEQ ID NO | PRIMER NUCLEOTIDE SEQUENCE |
|---|---|---|---|---|
| 1 | upstream | 18442 | 44 | 5'aggcactgaggtgattggc |
| 1 | downstream | 19109 | 45 | 5'cgtagcccttaagtgagc |
| 2 | upstream | 19689 | 46 | 5'aatatgtacattagagtagttg |
| 2 | downstream | 19688 | 47 | 5'cagagaaggtcctgactc |
| 3 | upstream | 19687 | 48 | 5'agagatttggaaatgagtaac |
| 3 | downstream | 19786 | 49 | 5'acacatgtcatcacaggagg |
| 4 | upstream | 18492 | 50 | 5'aacctttcccttggtgagg |
| 4 | downstream | 18421 | 51 | 5'gattactctgagacctaggc |
| 5 | upstream | 18313 | 52 | 5'gattttctcttttcccttggg |
| 5 | downstream | 18179 | 53 | 5'caaacaaagcttcaacaatttac |
| 6 | upstream | 18318 | 54 | 5'gggttttattttcaagtacttctatg |
| 6 | downstream | 18317 | 55 | 5'gctcagcaactgttcaatgtatgagc |
| 7 | upstream | 19009 | 56 | 5'ctagtgtgtgttttggc |
| 7 | downstream | 19135 | 57 | 5'cataaccttatctccacc |
| 8 | upstream | 18197 | 58 | 5'ctcagccatgagacaataaatcc |
| 8 | downstream | 18924 | 59 | 5'ggttcccaaataatgtgatgg |
| 9 | upstream | 18765 | 60 | 5'caaaagcttcagaatctc |
| 9 | downstream | 18198 | 61 | 5'ctgtgggtgtttcctgtgagtgg |
| 10 | upstream | 18305 | 62 | 5'catgactttgtgtgaatgtacacc |
| 10 | downstream | 18306 | 63 | 5'gaggagagcctgatagaacatctg |
| 11 | upstream | 18182 | 64 | 5'gggcttttctccccctccc |
| 11 | downstream | 19041 | 65 | 5'aaaatctgggctctcacg |

TABLE 2-continued

| EXON NO. | PRIMER LOCATION | PRIMER NO. | PRIMER SEQ ID NO | PRIMER NUCLEOTIDE SEQUENCE |
|---|---|---|---|---|
| 12 | upstream | 18579 | 66 | 5'aattatacctcatactagc |
| 12 | downstream | 18178 | 67 | 5'gttttattacagaataaaggagg |
| 12 | downstream | 19070 | 68 | 5'aagcaaaagttagaaggca |
| 13 | upstream | 18420 | 69 | 5'tgcaacccacaaaatttggc |
| 13 | downstream | 18443 | 70 | 5'ctttctccatttccaaaacc |
| 14 | upstream | 19028 | 71 | 5'tggtgtctctagttctgg |
| 14 | downstream | 18897 | 72 | 5'cattgttgtagtagctctgc |
| 15 | upstream | 19025 | 73 | 5'cccatttgtcccaactgg |
| 15 | downstream | 18575 | 74 | 5'cggtcagttgaaatgtcag |
| 16 | upstream | 18184 | 75 | 5'catttggatgctccgttaaagc |
| 16 | downstream | 18314 | 76 | 5'cacccggctggaaattttatttg |
| 17 | upstream | 18429 | 77 | 5'ggaaaggcactggagaaatggg |
| 17 | downstream | 18315 | 78 | 5'ccctccagcacacatgcatgtaccg |
| 18 | upstream | 18444 | 79 | 5'taagtagtctgtgatctccg |
| 18 | downstream | 18581 | 80 | 5'atgtatgaggtcctgtcc |
| 19 | upstream | 18638 | 81 | 5'gacaccagtgtatgttgg |
| 19 | downstream | 18637 | 82 | 5'gagaaagaagaacacatccc |

Additionally, we have designed a set of "second stage" amplification primers, the structures of which are shown below in Table 3. We use the second stage primers in conjunction with the first stage primers in a nested amplification protocol, as described below.

TABLE 3

| EXON NO. | PRIMER LOCATION | PRIMER NO. | PRIMER SEQ ID NO | PRIMER NUCLEOTIDE SEQUENCE |
|---|---|---|---|---|
| 1 | upstream | 19295 | 83 | 5'tgtaaaacgacggccagtcactgaggtgattggctgaa |
| 1 | downstream | 19446 | 84 | *5'tagcccttaagtgagcccg |
| 2 | upstream | 18685 | 85 | 5'tgtaaaacgacggccagttacattagagtagttgcaga |
| 2 | downstream | 19067 | 86 | *5'aggtcctgactcttccatg |
| 3 | upstream | 18687 | 87 | 5'tgtaaaacgacggccagtttggaaatgagtaacatgatt |
| 3 | downstream | 19068 | 88 | *5'tgtcatcacaggaggatat |
| 4 | upstream | 19294 | 89 | 5'tgtaaaacgacggccagtctttcccttggtgaggtga |
| 4 | downstream | 19077 | 90 | *5'tactctgagacctaggccca |
| 5 | upstream | 19301 | 91 | 5'tgtaaaacgacggccagttctcttttcccttgggattag |
| 5 | downstream | 19046 | 92 | *5'acaaagcttcaacaatttactct |
| 6 | upstream | 19711 | 93 | 5'tgtaaaacgacggccagtgttttattttcaagtacttctatgaatt |
| 6 | downstream | 19079 | 94 | *5'cagcaactgttcaatgtatgagcact |
| 7 | upstream | 19293 | 95 | 5'tgtaaaacgacggccagtgtgtgtgttttttggcaac |
| 7 | downstream | 19435 | 96 | *5'aaccttatctccaccagc |
| 8 | upstream | 19329 | 97 | 5'tgtaaaacgacggccagtagccatgagacaataaatccttg |
| 8 | downstream | 19450 | 98 | *5'tcccaaataatgtgatggaatg |
| 9 | upstream | 19608 | 99 | 5'tgtaaaacgacggccagtaagcttcagaatctctttt |
| 9 | downstream | 19449 | 100 | *5'tgggtgtttcctgtgagtggatt |
| 10 | upstream | 19297 | 101 | 5'tgtaaaacgacggccagtactttgtgtgaatgtacacctgtg |
| 10 | downstream | 19081 | 102 | *5'gagagcctgatagaacatctgttg |
| 11 | upstream | 19486 | 103 | 5'tgtaaaacgacggccagtcttttctcccccctcccacta |
| 11 | downstream | 19455 | 104 | *5'tctgggctctcacgtct |
| 12 | upstream | 20546 | 105 | *5'cttattctgagtctctcc |
| 12 | upstream | 20002 | 106 | 5'tgtaaaacgacggccagtgttttgctcagaggctgc |
| 12 | upstream | 19829 | 107 | *5'gatggttcgtacagattcccg |
| 12 | dowrstream | 19385 | 108 | 5'tgtaaaacgacggccagtttattacagaataaaggaggtag |
| 13 | upstream | 19300 | 109 | 5'tgtaaaacgacggccagtaacccacaaaatttggctaag |
| 13 | downstream | 19078 | 110 | *5'tctccatttccaaaaccttg |
| 14 | upstream | 19456 | 111 | *5'tgtctctagttctggtgc |
| 14 | downstream | 19472 | 112 | 5'tgtaaaacgacggccagtgttgtagtagctctgcttg |
| 15 | upstream | 19697 | 113 | *5'atttgtcccaactggttgta |
| 15 | downstream | 19466 | 114 | 5'tgtaaaacgacggccagtcagttgaaatgtcagaaagtg |
| 16 | upstream | 19269 | 115 | 5'tgtaaaacgacggccagt |
| 16 | downstream | 19047 | 116 | *5'ccggctggaaattttat#ggag |
| 17 | upstream | 19298 | 117 | 5'tgtaaaacgacggccagtaggcactggagaaatgggatttg |
| 17 | downstream | 19080 | 118 | *5'tccagcacacatgcatgtaccg#t |
| 18 | upstream | 19436 | 119 | *5'gtagtctgtgatctccgttt |
| 18 | downstream | 19471 | 120 | 5'tgtaaaacgacggccagttatgaggtcctgtcctag |
| 19 | upstream | 19447 | 121 | *5'accagtgtatgttgggatg |
| 19 | downstream | 19330 | 122 | 5'tgtaaaacgacggccagtgaaagaagaacacatcccaca |

In Table 3 an asteric (*) indicates that the 5' nucleotide is biotinylated. Exons 1–7, 10, 13 and 16–19 can be specifically amplified in PCR reactions containing either 1.5 mM or 3 mM MgCl$_2$. Exons 11 and 14 can only be specifically amplified in PCR reactions containing 1.5 mM MgCl$_2$ and exons 8, 9, 12 and 15 can only be specifically amplified in PCR reactions containing 3 mM MgCL$_2$. With respect to exon 12, the second stage amplification primers have been designed so that exon 12 is reamplified in two halves. The 20546 and 20002 primer set amplifies the N-terminal half The primer set 19829 and 19835 amplifies the C-terminal half. An alternate primer for 18178 is 19070.

The hMLH1 sequence information provided by our studies and disclosed m this application and preceding related applications, may be used to design a large number of different oligonucleotide primers for use in identifying hMLH1 mutations that correlate with cancer susceptibility and/or with tumor development in an individual, including primers that will amplify more than one exon (and/or flanking intron sequences) in a single product band.

One of ordinary skill in the art would be familiar with considerations important to the design of PCR primers for use to amplify the desired fragment or gene.[37] These considerations may be similar, though not necessarily identical to those involved in design of sequencing primers, as discussed above. Generally it is important that primers hybridize relatively specifically (i.e. have a $T_m$ of greater than about 55-degrees C., and preferably around 60-degrees C.). For most cases, primers between about 17 and 25 nucleotides in length work well. Longer primers can be useful for amplifying longer fragments. In all cases, it is desirable to avoid using primers that are complementary to more than one sequence in the human genome, so that each pair of PCR primers amplifies only a single, correct fragment. Nevertheless, it is only absolutely necessary that the correct band be distinguishable from other product bands in the PCR reaction.

The exact PCR conditions (e.g. salt concentration, number of cycles, type of DNA polymerase, etc.) can be varied as known in the art to improve, for example, yield or specificity of the reaction. In particular, we have found it valuable to use nested primers in PCR reactions in order to reduce the amount of required DNA substrate and to improve amplification specificity.

Two examples follow. The first example illustrates use of a first stage primer pair (SEQ ID NOS: 69 and 70) to amplify intron/exon segment (SEQ ID NO: 18). The second example illustrates use of second stage primers to amplify a target intron/exon segment from the product of a first PCR amplification step employing first stage primers.

EXAMPLE 1

Amplification of hMLH1 genomic clones from a P1 phage library 25 ng genomic DNA (or 1 ng of a P1 phage can be used) was used in PCR reactions including:

0.05 mM dNTPs 50 mM KCl 3 mM Mg 10 mM Tris-HCl pH 8.5

0.01% gelatin

5 µM primers

Reactions were performed on a Perkin-Elmer Cetus model 9600 thermal cycler. Reactions were incubated at 95-degrees C. for 5 minutes, followed by 35 cycles (30 cycles from a P1 phage) of:

94-degrees C. for 30 seconds 55-degrees C. for 30 seconds 72-degrees C. for 1 minute.

A final 7 minute extension reaction was then performed at 72 -degrees C. Desirable P1 clones were those from which an approximately bp product band was produced.

EXAMPLE 2

Amplification of hMLH1 Sequences from Genomic DNA Using Nested PCR Primers

We performed two-step PCR amplification of hMLH1 sequences from genomic DNA as follows. Typically, the first amplification was performed in a 25 microliter reaction including:

25 ng of chromosomal DNA

Perkin-Elmer PCR buffer II (any suitable buffer could be used)

3 mM MgCl$_2$

50 M each dNTP

Taq DNA polymerase

5 M primers (SEQ ID NOS: 69, 70) and incubated at 95-degrees C. for 5 minutes, followed by 20 cycles of:

94-degrees C. for 30 seconds 55-degrees C. for 30 seconds.

The product band was typically small enough (less than an approximately 500 bp) that separate extension steps were not performed as part of each cycle. Rather, a single extension step was performed, at 72-degrees C. for 7 minutes, after the 20 cycles were completed. Reaction products were stored at 4-degrees C.

The second amplification reaction, usually 25 or 50 microliters in volume, included:

1 or 2 microliters (depending on the volume of the reaction) of the first amplification reaction product Perkin-Elmer PCR buffer II (any suitable buffer could be used)

3 mM or MgCl$_2$

50 M each dNTP

Taq DNA polymerase

5 M nested primers (SEQ ID NOS: 109, 110), and was incubated at 95-degrees C. for 5 minutes, followed by 20–25 cycles of:

94-degrees C. for 30 seconds 55-degrees C. for 30 seconds a single extension step was performed, at 72-degrees C. for 7 minutes, after the cycles were completed. Reaction products were stored at 4-degrees C.

Any set of primers capable of amplifying a target hMLH1 sequence can be used in the first amplification reaction. We have used each of the primer sets presented in Table 2 to amplify an individual hMLH1 exon in the first amplification reaction. We have also used combinations of those primer sets, thereby amplifying multiple individual hMLH1 exons in the first amplification reaction.

The nested primers used in the first amplification step were designed relative to the primers used in the first amplification reaction. That is, where a single set of primers is used in the first amplification reaction, the primers used in the second amplification reaction should be identical to the primers used in the first reaction except that the primers used in the second reaction should not include the 5'-most nucleotides of the first amplification reaction primers, and should extend sufficiently more at the 3' end that the $T_m$ of the second amplification primers is approximately the same as the $T_m$ of the first amplification reaction primers. Our second reaction primers typically lacked the 3 5'-most nucleotides of the first amplification reaction primers, and extended approximately 3–6 nucleotides farther on the 3' end. SEQ ID NOS: 109, 110 are examples of nested primer pairs that could be used in a second amplification reaction when SEQ ID NOS: 69 and 70 were used in the first amplification reaction.

We have also found that it can be valuable to include a standard sequence at the 5' end of one of the second amplification reaction primers to prime sequencing reactions. Additionally, we have found it useful to biotinylate that last nucleotide of one or both of the second amplification reaction primers so that the product band can easily be purified using magnetic beads[40] and then sequencing reactions can be performed directly on the bead-associated products.[41-45]

For additional discussion of multiplex amplification and sequencing methods, see References by Zu et al. and Espelund et al.[46,47]

hMLH1 Link to Cancer

As a first step to determine whether hMLH1 was a candidate for the HNPCC locus on human chromosome 3p21-23,[3] we mapped hMLH1 by fluorescence in situ hybridization (FISH).[20,21] We used two separate genomic fragments (data not shown) of the hMLH1 gene in FISH analysis. Examination of several metaphase chromosome spreads localized hMLH1 to chromosome 3p21.3-23.

Figure 7:
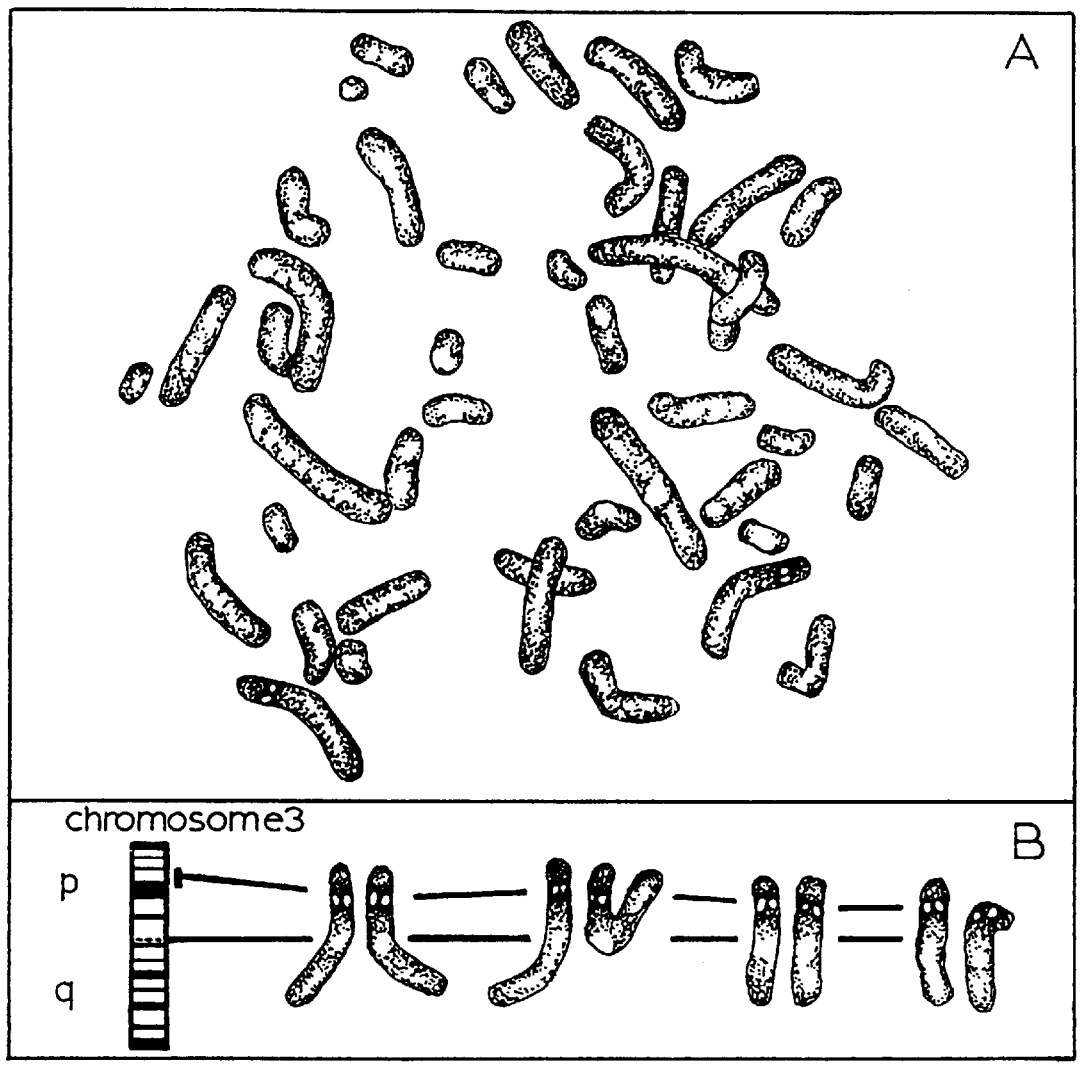
FIG. 7 is a two-panel photograph. The first panel (A) is a metaphase spread showing hybridization of the hMLH1 gene of chromosome 3. The second panel (B) is a composite of chromosome 3 from multiple metaphase spreads aligned with a human chromosome 3 ideogram. The region of hybridization is indicated in the ideogram by a vertical bar.

Panel A of FIG. 7 shows hybridization of hMLH1 probes in a metaphase spread. Biotinylated hMLH1 genomic probes were hybridized to banded human metaphase chromosomes as previously described.[20,21] Detection was performed with fluorescein isothiocyanate (FITC)-conjugated avidin (green signal); chromosomes, shown in blue, were counterstained with 4'6-diamino-2-phenylindole (DAPI). Images were obtained with a cooled CCD camera, enhanced, pseudocoloured and merged with the following programs: CCD Image Capture; NIH Image 1.4; Adobe Photoshop and Genejoin Maxpix respectively. Panel B of FIG. 7 shows a composite of chromosome 3 from multiple metaphase spreads aligned with the human chromosome 3 ideogram. Region of hybridization (distal portion of 3p21.3-23) is indicated in the ideogram by a vertical bar.

As independent confirmation of the location of hMLH1 on chromosome 3, we used both PCR with a pair of hMLH1-specific oligonucleotides and Southern blotting with a hMLH1-specific probe to analyze DNA from the NIGMS2 rodent/human cell panel (Coriell Inst. for Med. Res., Canden, N.J., USA). Results of both techniques indicated chromosome 3 linkage. We also mapped the mouse MLH1 gene by FISH to chromosome 9 band E. This is a position of synteny to human chromosome 3p.[22] Therefore, the hMLH1 gene localizes to 3p21.3-23, within the genomic region implicated in chromosome 3-linked HNPCC families.[3]

Next, we analyzed blood samples from affected and unaffected individuals from two chromosome-3 candidate HNPCC families[3] for mutations. One family, Family 1, showed significant linkage (lod score=3.01 at recombination fraction of 0) between HNPCC and a marker on 3p. For the second family, Family 2, the reported lod score (1.02) was below the commonly accepted level of significance, and thus only suggested linkage to the same marker on 3p. Subsequent linkage analysis of Family 2 with the microsatellite marker D3S1298 on 3p21.3 gave a more significant lod score of 1.88 at a recombination fraction of 0. Initially, we screened for mutations in two PCR-amplified exons of the hMLH1 gene by direct DNA sequencing (FIG. 4). We examined these two exons from three affected individuals of Family 1, and did not detect any differences from the expected sequence. In Family 2, we observed that four individuals affected with colon cancer are heterozygous for a C to T substitution in an exon encoding amino acids 41–69, which corresponds to a highly-conserved region of the protein (FIG. 9). For one affected individual, we screened PCR-amplified cDNA for additional sequence differences. The combined sequence information obtained from the two exons and cDNA of this one affected individual represents 95% (i.e. all but the first 116 bp) of the open reading frame. We observed no nucleotide changes other than the C to T substitution. In addition, four individuals from Family 2, predicted to be carriers based upon linkage data, and as yet unaffected with colon cancer, were found to be heterozygous for the same C to T substitution. Two of these predicted carriers are below and two are above the mean age of onset (50 years) in this particular family. Two unaffected individuals examined from this same family, both predicted by linkage data to be non carriers, showed the expected normal sequence at this position. Linkage analysis that includes the C to T substitution in Family 2 gives a lod score of 2.23 at a recombination fraction 0. Using low stringency cancer diagnostic criteria, we calculated a lod score of 2.53. These data indicate the C to T substitution shows significant linkage to the HNPCC in Family 2.

Figure 8:
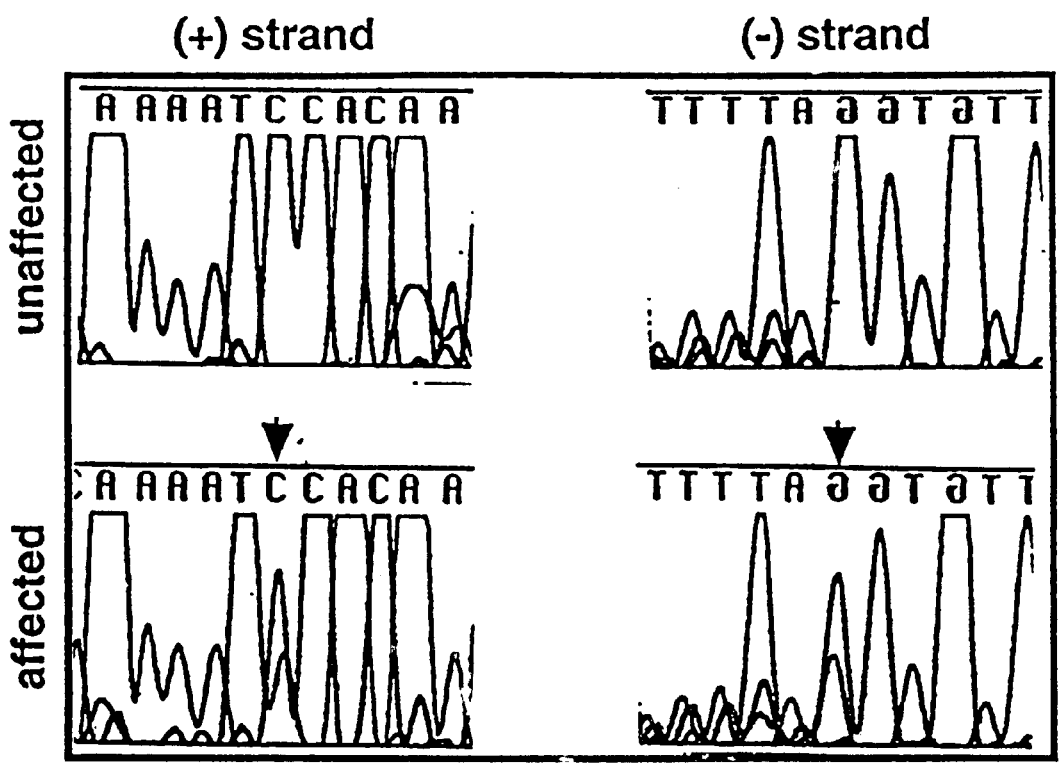
FIG. 8 is a comparison of sequence chromatograms from affected and unaffected individuals showing identification of a C to T transition mutation that produces a non-conservative amino acid substitution at position 44 of the hMLH1 protein.

FIG. 8 shows sequence chromatograms indicating a C to T transition mutation that produces a non-conservative amino acid substitution at position 44 of the hMLH1 protein. Sequence analysis of one unaffected (top panels, plus and minus strands) and one affected individual (lower panels, plus and minus strands) is presented. The position of the heterozygous nucleotide is indicated by an arrow. Analysis of the sequence chromatographs indicates that there is sufficient T signal in the C peak and enough A signal in the G peak for the affected individuals to be heterozygous at this site.

To determine whether this C to T substitution was a polymorphism, we sequenced this same exon amplified from the genomic DNA from 48 unrelated individuals and observed only the normal sequence. We have examined an additional 26 unrelated individuals using allele specific oligonucleotide (ASO) hybridization analysis.[33] The ASO sequences (SEQ ID NOS: 141 and 142, respectively) which we used are:

5'-ACTTGTGGATTTTGC-3' and 5'-ACTTGTGAAT TTTGC-3'.

Based upon direct DNA sequencing and ASO analysis, none of these 74 unrelated individuals carry the C to T substitution. Therefore, the C to T substitution observed in Family 2 individuals is not likely to be a polymorphism. As mentioned above, we did not detect this same C to T substitution in affected individuals from a second chromosome 3-linked family, Family 1.[3] We are continuing to study individuals of Family 1 for mutations in hMLH1.

Table 4 below summarizes our experimental analysis of blood samples from affected and unaffected individuals from Family 2 and unrelated individuals.

TABLE 4

| FAMILY 2 Status | Number of Individuals with C to T Mutation/ Number of Individuals Tested |
|---|---|
| Affected | 4/4 |
| Predicted Carriers | 4/4 |
| Predicted Non-carriers | 0/2 |
| Unrelated Individuals | 0/74 |

Based on several criteria, we suggest that the observed C to T substitution in the coding region of hMLH1 represents the mutation that is the basis for HNPCC in Family 2.[3] First, DNA sequence and ASO analysis did not detect the C to T substitution in 74 unrelated individuals. Thus, the C to T substitution is not simply a polymorphism. Second, the observed C to T substitution is expected to produce a serine to phenylalanine change at position 44 (See FIG. 9). This amino acid substitution is a non-conservative change in a conserved region of the protein (FIGS. 3 and 9). Secondary structure predictions using Chou-Fasman parameters suggest a helix-turn-beta sheet structure with position 44 located in the turn. The observed Ser to Phe substitution, at position 44 lowers the prediction for this turn considerably, suggesting that the predicted amino acid substitution alters the conformation of the hMLH1 protein. The suggestion that the Ser to Phe substitution is a mutation which confers cancer susceptibility is further supported by our experiments which show that an analogous substitution (alanine to phenylalanine) in a yeast MLH1 gene results in a nonfunctional mismatch repair protein. In bacteria and yeast, a mutation affecting DNA mismatch repair causes comparable increases in the rate of spontaneous mutation including additions and deletions within dinucleotide repeats.[4,5,11,13,14,15,16] In humans, mutation of hMSH2 is the basis of chromosome-2 HNPCC,[1,2] tumors which show microsatellite instability and an apparent defect in mismatch repair.[12] Chromosome 3-linked HNPCC is also associated with instability of dinucleotide repeats.[3] Combined with these observations, the high degree of conservation between the human MLH1 protein and the yeast DNA mismatch repair protein hMLH1 suggests that hMLH1 is likely to function in DNA mismatch repair. During isolation of the hMLH1 gene, we identified the hPMS1 gene. This observation suggests that mammalian DNA mismatch repair, like that in yeast,[4] may require at least two mutL-like proteins.

It should be noted that it appears that different HNPCC families show different mutations in the MLH1 gene. As explained above, affected individuals in Family 1 showed "tight linkage" between HNPCC and a locus in the region of 3p21-23. However, affected individuals in Family 1 do not have the C to T mutation found in Family 2. It appears that the affected individuals in Family 1 have a different mutation in their MLH1 gene. Further, we have used the structure information and methods described in this application to find and characterize another hMLH1 mutation which apparently confers cancer susceptibility in heterozygous carriers of the mutant gene in a large English HNPCC family. The hMLH1 mutation in the English family is a +1 T frameshift which is predicted to lead to the synthesis of a truncated hMLH1 protein. Unlike, for example, sickle cell anemia, in which essentially all known affected individuals have the same mutation multiple hMLH1 mutations have been discovered and linked to cancer. Therefore, knowledge of the entire cDNA sequence for hMLH1 (and probably hPMS1), as well as genomic sequences particularly those that surround exons, will be useful and important for characterizing mutations in families identified as exhibiting a high frequency of cancer.

Subsequent to our discovery of a cancer conferring mutation in hMLH1, studies by others have resulted in the characterization of at least 5 additional mutations in hMLH1, each of which appears to have conferred cancer susceptibility to individuals in at least one HNPCC family. For example, Papadopoulos et al. indentified such as a mutation, characterized by an in-frame deletion of 165 base pairs between codons 578 to 632. In another family, Papadopoulos et al. observed an hMLH1 mutation, characterized by a frame shift and substitution of new amino acids, namely, a 4 base pair deletion between codons 727 and 728. Papadopoulos et al. also reports an hMLH1 cancer linked mutation, characterized by an extension of the COOH terminus, namely, a 4 base pair insertion between codons 755 and 756.[38]

In summary, we have shown that DNA mismatch repair gene hMLH1 which is likely to be the hereditary nonpolyposis colon cancer gene previously localized by linkage analysis to chromosome 3p21-23.[3] Availability of the hMLH1 gene sequence will facilitate the screening of HNPCC families for cancer-linked mutations. In addition, although loss of heterozygosity (LOH) of linked markers is not a feature of either the 2p or 3p forms of HNPCC,[3,6] LOH involving the 3p21.3-23 region has been observed in several human cancers.[24,26] This suggests the possibility that hMLH1 mutation may play some role in these tumors.

Human PMS1

Figure 10:
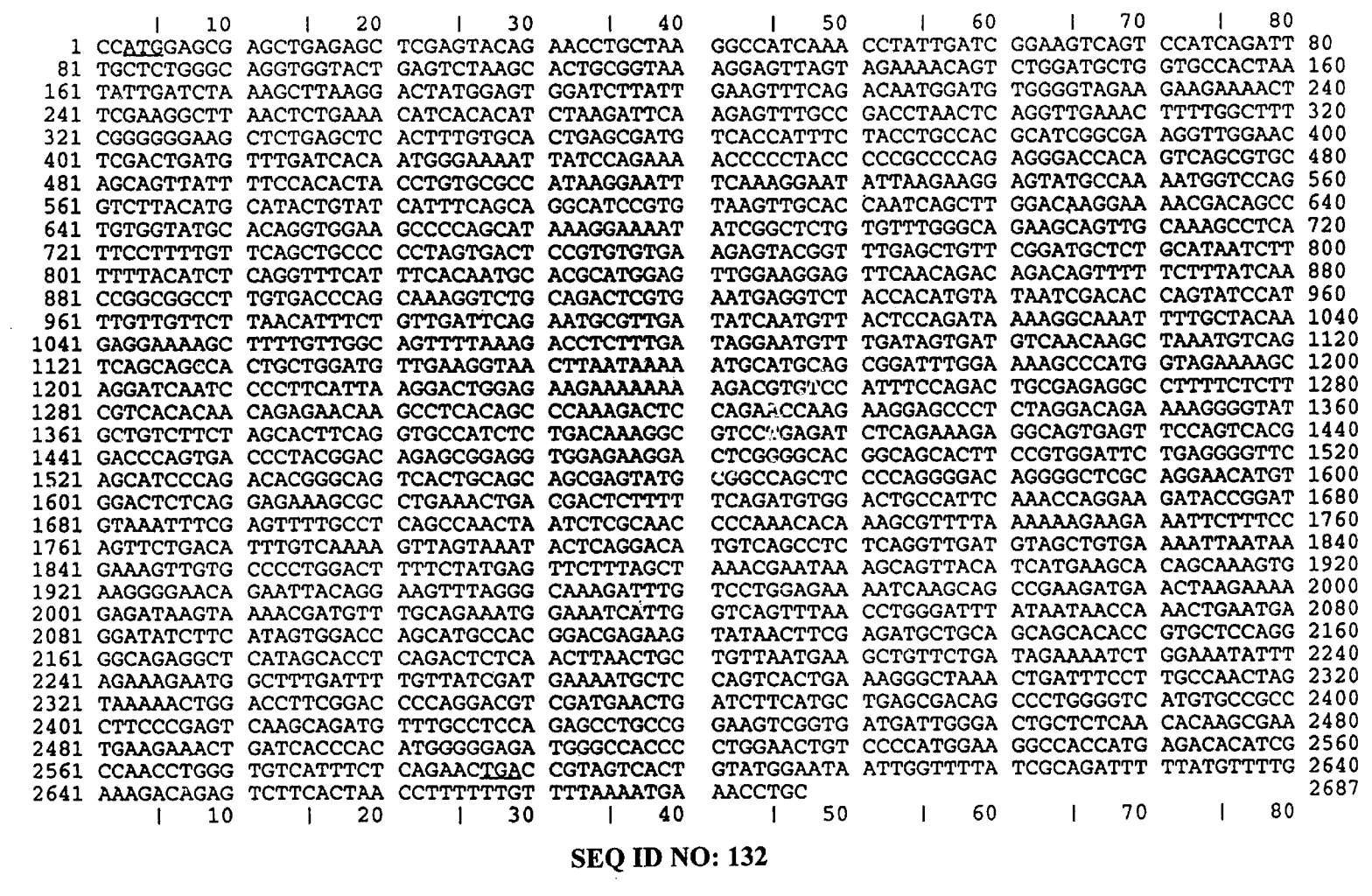
Figure 11:
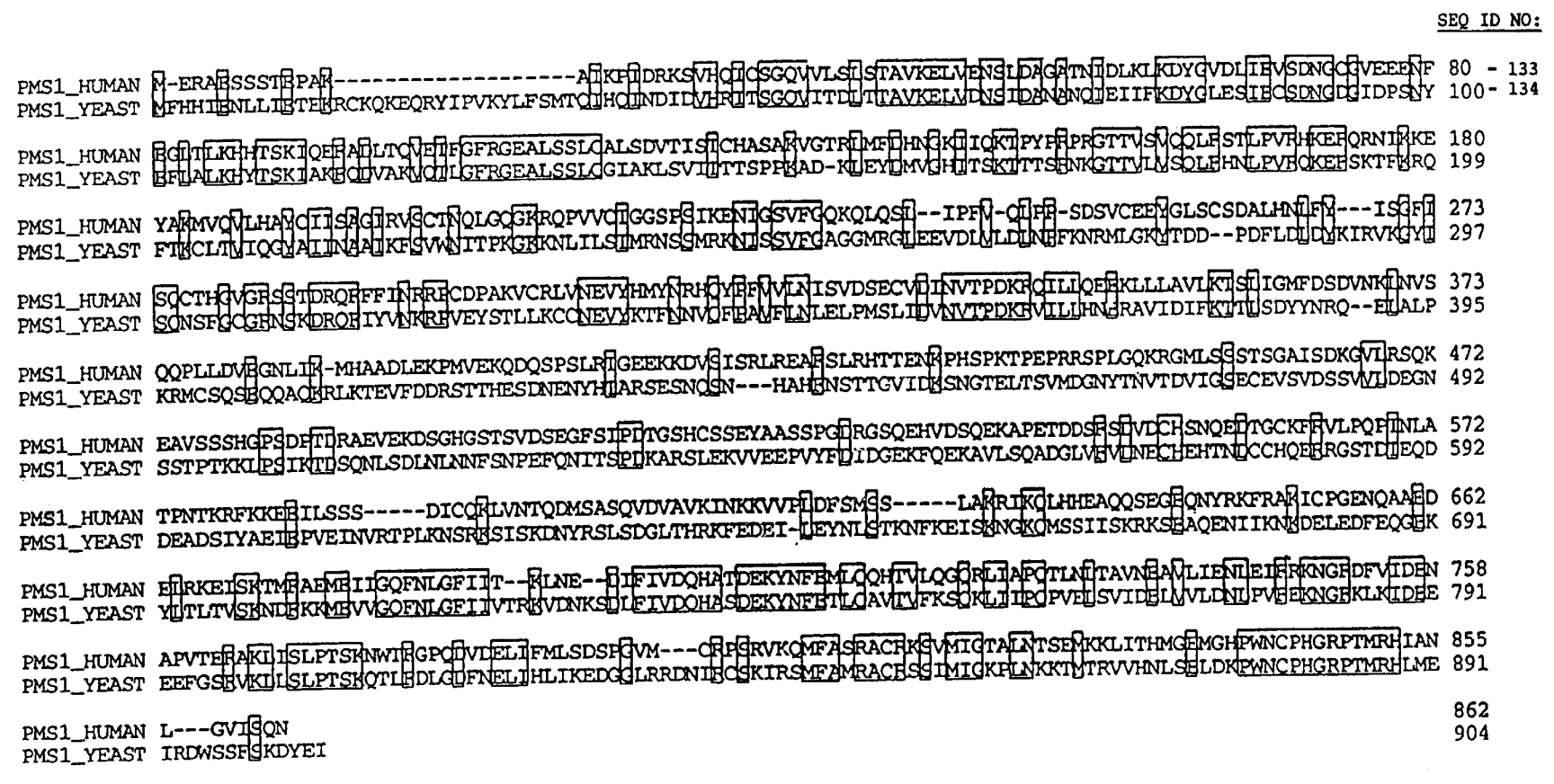

Human PMS1 was isolated using the procedures discussed with reference to FIG. 1. FIG. 10 shows the entire hPMS1 cDNA nucleotide sequence. FIG. 11 shows an alignment of the predicted human and yeast PMS 1 protein sequences. We determined by FISH analysis that human PMS1 is located on chromosome 7. Subsequent to our discovery of hPMS1, others have identified mutations in the gene which appear to confer HNPCC susceptibility.[39]

Mouse MLH1

Using the procedure outlined above with reference to FIG. 1, we have determined a partial nucleotide sequence of mouse MLH1 cDNA, as shown in FIG. 12 (SEQ ID NO: 135). FIG. 13 shows the corresponding predicted amino acid sequence for mMLH1 protein (SEQ ID NO: 136) in comparison to the predicted hMLH1 protein sequence (SEQ ID NO: 5). Comparison of the mouse and human MLH1 proteins as well as the comparison of hMLH1 with yeast MLH1 proteins, as shown in FIG. 9, indicate a high degree of conservation.

Mouse PMS1

Using the procedures discussed above with reference to FIG. 1, we isolated and sequenced the mouse PMS1 gene, as shown in FIG. 14 (SEQ ID NO: 137). This cDNA sequence encodes a predicted protein of 864 amino acids (SEQ ID NO: 138), as shown in FIG. 15, where it is compared to the predicted amino acid sequence for HPMS1 (SEQ ID NO: 133). The degree of identity between the predicted mouse and human PMS1 proteins is high, as would be expected between two mammals. Similarly, as noted above, there is a strong similarity between the human PMS1 protein and the yeast DNA mismatch repair protein PMS 1, as shown in FIG. 11. The fact that yeast PMS1 and MLH1 function in yeast to repair DNA mismatches, strongly suggests that human and mice PMS1 and MLH1 are also mismatch repair proteins.

Uses for Mouse MLH1 and PMS1

We believe our isolation and characterization of mMLH1 and mPMS1 genes will have many research applications. For example, as already discussed above, we have used our knowledge of the mPMS1 gene to produce antibodies which react specifically with hPMS1. We have already explained that antibodies directed to the human proteins, MLH1 or PMS1 may be used for both research purposes as well as diagnostic purposes.

We also believe that our knowledge of mPMS1 and mMLH1 will be useful for constructing mouse models in order to study the consequences of DNA mismatch repair defects. We expect that mPMS1 or mMLH1 defective mice will be highly prone to cancer because chromosome 2p and 3p-associated HNPCC are each due to a defect in a mismatch repair gene.[1,2] As noted above, we have already produced chimeric mice which carry an mPMS1 defective gene. We are currently constructing mice heterozygous for mPMS1 or mMLH1 mutation. These heterozygous mice should provide useful animal models for studying human cancer, in particular HNPCC. The mice will be useful for analysis of both intrinsic and extrinsic factors that determine cancer risk and progression. Also, cancers associated with mismatch repair deficiency may respond differently to conventional therapy in comparison to other cancers. Such animal models will be useful for determining if differences exist, and allow the development of regimes for the effective treatment of these types of tumors. Such animal models may also be used to study the relationship between hereditary versus dietary factors in carcinogenesis.

Distinguishing Mutations From Polymorphisms

For studies of cancer susceptibility and for tumor identification and characterization, it is important to distinguish "mutations" from "polymorphisms". A "mutation" produces a "non-wild-type allele" of a gene. A non-wild-type allele of a gene produces a transcript and/or a protein product that does not function normally within a cell. "Mutations" can be any alteration in nucleotide sequence including insertions, deletions, substitutions, and rearrangements.

"Polymorphisms", on the other hand, are sequence differences that are found within the population of normally-functioning (i.e., "wild-type") genes. Some polymorphisms result from the degeneracy of the nucleic acid code. That is, given that most amino acids are encoded by more than one triplet codon, many different nucleotide sequences can encode the same polypeptide. Other polymorphisms are simply sequence differences that do not have a significant effect on the function of the gene or encoded polypeptide. For example, polypeptides can often tolerate small insertions or deletions, or "conservative" substitutions in their amino acid sequence without significantly altering function of the polypeptide.

"Conservative" substitutions are those in which a particular amino acid is substituted by another amino acid of similar chemical characteristics. For example, the amino acids are often characterized as "non-polar (hydrophobic)" including alanine, leucine, isoleucine, valine, proline, phenylaline, tryptophan, and methionine; "polar neutral", including glycine, serine, threonine, cysteine, tyrosine, asparagine, and glutamine; "positively charged (basic)", including arginine, lysine, and histidine; and "negatively charged (acidic)", including aspartic acid and glutamic acid. A substitution of one amino acid for another amino acid in the same group is generally considered to be "conservative", particularly if the side groups of the two relevant amino acids are of a similar size.

The first step in identifying a mutation or polymorphism in a mismatch repair gene sequence involves identification, using available techniques including those described herein, of a mismatch repair gene, (or gene fragment) sequence that differs from a known, normal (e.g. wild-type) sequence of the same mismatch repair gene (or gene fragment). For example, a hMLH1 gene (or gene fragment) sequence could be identified that differs in at least one nucleotide position from a known normal (e.g. wild-type) hMLH1 sequence such as any of SEQ ID NOS: 6–24.

Mutations can be distinguished from polymorphisms using any of a variety of methods, perhaps the most direct of which is data collection and correlation with tumor development. That is, for example, a subject might be identified whose hMLH1 gene sequence differs from a sequence reported in SEQ ID. NOS: 6–24, but who does not have cancer and has no family history of cancer. Particularly if other, preferably senior, members of that subject's family have hMLH1 gene sequences that differ from SEQ ID NOS: 6–24 in the same way(s), it is likely that subject's hMLH1 gene sequence could be categorized as a "polymorphism". If other, unrelated individuals are identified with the same hMLH1 gene sequence and no family history of cancer, the categorization may be confirmed.

Mutations that are responsible for conferring genetic susceptibility to cancer can be identified because, among other things, such mutations are likely to be present in all tissues of an affected individual and in the germ line of at least one of that individual's parents, and are not likely to be found in unrelated families with no history of cancer.

When distinguishing mutations from polymorphisms, it can sometimes be valuable to evaluate a particular sequence difference in the presence of at least one known mismatch repair gene mutation. In some instances, a particular sequence change will not have a detectable effect (i.e., will appear to be a polymorphism) when assayed alone, but will, for example, increase the penetrance of a known mutation, such that individuals carrying both the apparent polymorphism difference and a known mutation have higher probability of developing cancer than do individuals carrying only the mutation. Sequence differences that have such an effect are properly considered to be mutations, albeit weak ones.

As discussed above and previously (U.S. patent application Ser. Nos. 08/168,877 and 08/209,521), mutations in mismatch repair genes or gene products produced non-wild-type versions of those genes or gene products. Some mutations can therefore be distinguished from polymorphisms by their functional characteristics in vivo or in vitro mismatch repair assays. Any available mismatch repair assay can be used to analyze these characteristics.[49-63] It is generally desirable to utilize more than one mismatch repair assay before classifying a sequence change as a polymorphism, since some mutations will have effects that will not be observed in all assays.

For example, a mismatch repair gene containing a mutation would not be expected to be able to replace an endogenous copy of the same gene in a host cell without detectably affecting mismatch repair in that cell; whereas a mismatch repair gene containing a sequence polymorphism would be expected to be able to replace an endogenous copy of the same gene in a host cell without detectably affecting mismatch repair in that cell. We note that for such "replacement" studies, it is generally desirable to introduce the gene to be tested into a host cell of the same (or at least closely related) species as the cell from which the test gene was derived, to avoid complications due to, for example, the inability of a gene product from one species to interact with other mismatch repair gene products from another species. Similarly, a mutant mismatch repair protein would not be expected to function normally in an in vitro mismatch repair system (preferably from a related organism); whereas a polymorphic mismatch repair protein would be expected to function normally.

The methods described herein and previously allow identification of different kinds of mismatch repair gene mutations. The following examples illustrate protocols for distinguishing mutations from polymorphisms in DNA mismatch repair genes.

EXAMPLE 3

We have developed a system for testing in yeast, *S. cerevisiae* the functional significance of mutations found in either the hMLH1 or hPMS1 genes. The system is described in this application using as an example, the serine (SER) to phenylalanine (PHE) causing mutation in hMLH1 that we found in a family with HNPCC, as described above. We have derived a yeast strain that it is essentially deleted for its MLH1 gene and hence is a strong mutator (i.e., 1000 fold above the normal rate in a simple genetic marker assay involving reversion from growth dependence on a given amino acid to independence (reversion of the hom3-10 allele, Prolla, Christie and Liskay, Mol Cell Biol, 14:407–415, 1994). When we placed the normal yeast MLH1 gene (complete with all known control regions) on a yeast plasma that is stably maintained as a single copy into the MLH1-deleted strain, the mutator phenotype is fully corrected using the reversion to amino acid independence assay. However, if we introduce a deleted copy of the yeast MLH1 there is no correction. We next tested the mutation that in the HNPCC family caused a SER to PHE alteration. We found that the resultant mutant yeast protein cannot correct the mutator phenotype, strongly suggesting that the alteration from the wild-type gene sequence probably confers cancer susceptibility, and is therefore classified as a mutation, not a polymorphism. We subsequently tested proteins engineered to contain other amino acids at the "serene" position and found that most changes result in a fully mutant, or at least partially mutant phenotype.

As other "point" mutations in MLH1 and PMS1 genes are found in cancer families, they can be engineered into the appropriate yeast homolog gene and their consequence on protein function studied. In addition, we have identified a number of highly conserved amino acids in both the MLH1 and PMS1 genes. We also have evidence that hMLH1 interacts with yeast PMS1. This finding raises the possibility that mutations observed in the hMLH1 gene can be more directly tested in the yeast system. We plan to systematically make mutations that will alter the amino acid at these conserved positions and determine what amino acid substitutions are tolerated and which are not. By collecting mutation information relating to hMLH1 and hPMS1, both by determining and documenting actual found mutations in HNPCC families, and by artificially synthesizing mutants for testing in experimental systems, it may be eventually possible to practice a cancer susceptibility testing protocol which, once the individuals hMLH1 or hPMS1 structure is determined, only requires comparison of that structure to known mutation versus polymorphism data.

EXAMPLE 4

Another method which we have employed to study physical interactions between hMLH1 and hPMS1, can also be used to study whether a particular alteration in a gene product results in a change in the degree of protein-protein interaction. Information concerning changes in protein-protein interaction may demonstrate or confirm whether a particular genomic variation is a mutation or a polymorphism. Following our labs findings on the interaction between yeast MLH1 and PMS1 proteins in vitro and in vivo, U.S. patent application Ser. No. 08/168,877), the interaction between the human counterparts of these two DNA mismatch repair proteins was tested. The human MLH1 and human PMS1 proteins were tested for in vitro interaction using maltose binding protein (MBP) affinity chromatography. hMLH1 protein was prepared as an MBP fusion protein, immobilized on an amylose resin column via the MBP, and tested for binding to hPMS1, synthesized in vitro. The hPMS1 protein bound to the MBP-hMLH1 matrix, whereas control proteins showed no affinity for the matrix. When the hMLH1 protein, translated in vitro, was passed over an MBP-hPMS1 fusion protein matrix, the hMLH1 protein bound to the MBP-hPMS1 matrix, whereas control proteins did not.

Potential in vivo interactions between hMLH1 and hPMS1 were tested using the yeast "two hybrid" system.[28] Our initial results indicate that hMLH1 and hPMS1 interact in vivo in yeast. The same system can also be used to detect changes in protein-protein interaction which result from changes in gene or gene product structure and which have yet to be classified as either a polymorphism or a mutation which confers cancer susceptibility.

Detection of HNPCC Families and Their Mutation(s)

It has been estimated that approximately 1,000,000 individuals in the United States carry (are heterozygous for) an HNPCC mutant gene.[29] Furthermore, estimates suggest that 50–60% of HNPCC families segregate mutations in the MSH2 gene that resides on chromosome 2p.[1,2] Another significant fraction appear to be associated with the HNPCC gene that maps to chromosome 3p21-22, presumably due to hMLH1 mutations such as the C to T transition discussed above. Identification of families that segregate mutant alleles of either the hMSH2 or hMLH1 gene, and the determination of which individuals in these families actually have the mutation will be of great utility in the early intervention into the disease. Such early intervention will likely include early detection through screening and aggressive follow-up treatment of affected individuals. In addition, determination of the genetic basis for both familial and sporadic tumors could direct the method of therapy in the primary tumor, or in recurrences.

Initially, HNPCC candidate families will be diagnosed partly through the study of family histories, most likely at the local level, e.g., by hospital oncologists. One criterion for BNPCC is the observation of microsatellite instability in individual's tumors.[3,6] The presenting patient would be tested for mutations in hMSH2, hMLH1, hPMS1 and other genes involved in DNA mismatch repair as hey are identified. This is most easily done by sampling blood from the individual. Also highly useful would be freshly frozen tumor tissue. It is important to note for the screening procedure, that affected individuals are heterozygous for the offending mutation in their normal tissues.

The available tissues, e.g., blood and tumor, are worked up for PCR-based mutation analysis using one or both of the following procedures:

1) Linkage analysis with a microsatellite marker tightly linked to the hMLH1 gene.

One approach to identify cancer prone families with a hMLH1 mutation is to perform linkage analysis with a highly polymorphic marker located within or tightly linked to hMLH1. Microsatellites are highly polymorphic and therefore are very useful as markers in linkage analysis. Because we possess the hMLH1 gene on a single large genomic fragment in a P1 phage clone (~100 kbp), it is very likely that one or more microsatellites, e.g., tracts of dinucleotide repeats, exist within, or very close to, the hMLH1 gene. At least one such microsatellite has been reported.[38] Once such markers have been identified, PCR primers will be designed to amplify the stretches of DNA containing the microsatellites. DNA of affected and unaffected individuals from a family with a high frequency of cancer will be screened to determine the segregation of the MLH1 markers and the presence of cancer. The resulting data can be used to calculate a lod score and hence determine the likelihood of linkage between hMLH1 and the occurrence of cancer. Once linkage is established in a given family, the same polymorphic marker can be used to test other members of the kindred for the likelihood of their carrying the hMLH1 mutation.

2) Sequencing of reverse transcribed cDNA.

a) RNA from affected individuals, unaffected and unrelated individuals is reverse transcribed (RT'd), followed by PCR to amplify the cDNA in 4–5 overlapping portions.[34,37] It should be noted that for the purposes of PCR, many different oligonucleotide primer pair sequences may potentially be used to amplify relevant portions of an individual's hMLH1 or hPMS1 gene for genetic screening purposes. With the knowledge of the cDNA structures for the genes, it is a straight-forward exercise to construct primer pairs which are likely to be effective for specifically amplifying selected portions of the gene. While primer sequences are typically between 20 to 30 bases long, it may be possible to use shorter primers, potentially as small as approximately 13 bases, to amplify specifically selected gene segments. The principal limitation on how small a primer sequence may be is that it must be long enough to hybridize specifically to the targeted gene segment. Specificity of PCR is generally improved by lengthening primers and/or employing nested pairs of primers.

The PCR products, in total representing the entire cDNA, are then sequenced and compared to known wild-type sequences. In most cases a mutation will be observed in the affected individual. Ideally, the nature of mutation will indicate that it is likely to inactivate the gene product. Otherwise, the possibility that the alteration is not simply a polymorphism must be determined.

b) Certain mutations, e.g., those affecting splicing or resulting in translation stop codons, can destabilize the messenger RNA produced from the mutant gene and hence comprise the normal RT-based mutation detection method. One recently reported technique can circumvent this problem by testing whether the mutant cDNA can direct the synthesis of normal length protein in a coupled in vitro transcription/translation system.[32]

3) Direct sequencing of genomic DNA.

A second route to detect mutations relies on examining the exons and the intron/exon boundaries by PCR cycle sequencing directly off a DNA template.[1,2] This method requires the use of oligonucleotide pairs, such as those described in Tables 2 and 3 above, that amplify individual exons for direct PCR cycle sequencing. The method depends upon genomic DNA sequence information at each intron/exon boundary (50 bp, or greater, for each boundary). The advantage of the technique is two fold. First, because DNA is more stable than RNA, the condition of the material used for PCR is not as important as it is for RNA-based protocols. Second, most any mutation within the actual transcribed region of the gene, including those in an intron affecting splicing, will be detectable.

For each candidate gene, mutation detection may require knowledge of both the entire cDNA structure, and all intron/exon boundaries of the genomic structure. With such information, the type of causal mutation in a particular family can be determined. In turn, a more specific and efficient mutation detection scheme can be adapted for the particular family. Screening for the disease (HNPCC) is complex because it has a genetically heterogeneous basis in the sense that more than one gene is involved, and for each gene, multiple types of mutations are involved.[2] Any given family is highly likely to segregate one particular mutation. However, as the nature of the mutation in multiple families is determined, the spectrum of the most prevalent mutations in the population will be determined. In general, determination of the most frequent mutations will direct and streamline mutation detection.

Because HNPCC is so prevalent in the human population, carrier detection at birth could become part of standardized neonatal testing. Families at risk can be identified and all members not previously tested can be tested. Eventually, all affected kindreds could be determined.

Mode of Mutation Screening and Testing

DNA-based Testing

Initial testing, including identifying likely HNPCC families by standard diagnosis and family history study, will likely be done in local and smaller DNA diagnosis laboratories. However, large scale testing of multiple family members, and certainly population wide testing, will ultimately require large efficient centralized commercial facilities.

Tests will be developed based on the determination of the most common mutations for the major genes underlying HNPCC, including at least the hMSH2 gene on chromosome 2p and the MLH1 gene on chromosome 3p. A variety of tests are likely to be developed. For example, one possibility is a set of tests employing oligonucleotide hybridizations that distinguish the normal vs. mutant alleles.[33] As already noted, our knowledge of the nucleotide structures for hMLH1, hPMS1 and hMSH2 genes makes possible the design of numerous oligonucleotide primer pairs which may be used to amplify specific portions of an individual's mismatch repair gene for genetic screening and cancer risk analysis. Our knowledge of the genes' structures also makes possible the design of labeled probes which can be quickly used to determine the presence or absence of all or a portion of one of the DNA mismatch repair genes. For example, allele-specific oligomer probes (ASO) may be designed to distinguish between alleles. ASOs are short DNA segments that are identical in sequence except for a single base difference that reflects the difference between normal and mutant alleles. Under the appropriate DNA hybridization conditions, these probes can recognize a single base difference between two otherwise identical DNA sequences. Probes can be labeled radioactively or with a variety of non-radioactive reporter molecules, for example, fluorescent or chemiluminescent moieties. Labeled probes are then used to analyze the PCR sample for the presence of the disease-causing allele. The presence or absence of several different disease-causing genes can readily be determined in a single sample. The length of the probe must be long enough to avoid non-specific binding to nucleotide sequences other than the target. All tests will depend ultimately on accurate and complete structural information relating to hMLH1, hMSH2, hPMS1 and other DNA mismatch repair genes implicated in HNPCC.

Protein Detection-Based Screening

Tests based on the functionality of the protein product, per se, may also be used. The protein-examining tests will most likely utilize antibody reagents specific to either the hMLH1, hPMS1 or hMSH2 proteins or other related "cancer" gene products as they are identified.

For example, a frozen tumor specimen can be sectioned and prepared for antibody staining using indirect fluorescence techniques. Certain gene mutations are expected to alter or destabilize the protein structure sufficiently such as to give an altered or reduced signal after antibody staining It is likely that such tests will be performed in cases where gene involvement in a family's cancer has yet to be established. Monoclonal antibodies are developed against the human MLH1 and PMS1 proteins. MLH1 and PMS1 human proteins are overexpressed in bacteria. Proteins are purified and injected into mice. Protein specific monoclonal antibodies are derived which can be used for diagnostic and research purposes. For example, two different monoclonal antibodies directed to hMLH1 are now available from PharMingen under catalog #13271A, clone: G168-15 and #13291A, clone: G168-728. Both of PharMingen's monoclonal antibodies were generated based on purified, recombinant hMLH1 protein, that was provided by applicants to PharMingen in the form of a fusion to bacterial protein.

Recent research suggests that methylation of hMLH1 promoter DNA is involved in mismatch repair gene inactivation in some sporadic tumors.[64,65] In this situation, there is usually no detectable mutation in the hMLH1 cDNA. A screening test for hMLH1 cDNA mutations would not show any abnormality. However, an immunoassay for hMLH1 protein will show presence or absence of the protein. It is believed that 90-percent or more of sporadic colon tumors and endometrial tumors that are DNA mismatch repair defective, do not have mutations in any known gene, but instead are MLH1 protein deficient due to methylation of the promotor region of the gene. It appears that the most reliable method for detecting absence of hMLH1 in sporadic tumors is to use labeled antibodies in an immunohistochemical staining procedure of tumor sections. It is likely that immunohistochemical staining of tumor tissue sections with monoclonal antibodies directed to hMLH1 protein will become a standard diagnostic method at least for colon and endometrial tumors.

Identification and Characterization of DNA Mismatch Repair Tumors

In addition to their usefulness in diagnosing cancer susceptibility in a subject, nucleotide sequences that are homologous to a bacterial mismatch repair gene can be valuable for, among other things, use in the identification and characterization of mismatch-repair-defective tumors. Such identification and characterization is valuable because mismatch-repair-defective tumors may respond better to particular therapy regimens. For example, mismatch-repair-defective tumors might be sensitive to DNA damaging agents, especially when administered in combination with other therapeutic agents.

Defects in mismatch repair genes need not be present throughout an individuals tissues to contribute to tumor formation in that individual. Spontaneous mutation of a mismatch repair gene in a particular cell or tissue can contribute to tumor formation in that tissue. In fact, at least in some cases, a single mutation in a mismatch repair gene is not sufficient for tumor development. In such instances, an individual with a single mutation in a mismatch repair gene is susceptible to cancer, but will not develop a tumor until a secondary mutation occurs. Additionally, in some instances, the same mismatch repair gene mutation that is strictly tumor-associated in an individual will be responsible for conferring cancer susceptibility in a family with a hereditary predisposition to cancer development.

In yet another aspect of the invention, the sequence information we have provided can be used with methods known in the art to analyze tumors (or tumor cell lines) and to identify tumor-associated mutations in mismatch repair genes. Preferably, it is possible to demonstrate that these tumor-associated mutations are not present in non-tumor tissues from the same individual. The information described in this application is particularly useful for the identification of mismatch repair gene mutations within tumors (or tumor cell lines) that display genomic instability of short repeated to DNA elements.

The sequence information and testing protocols of the present invention can also be used to determine whether two tumors are related, i.e., whether a second tumor is the result of metastasis from an earlier found first tumor which exhibits a particular DNA mismatch repair gene mutation.

Isolating Additional Genes of Related Function

Proteins that interact physically with either hMLH1 and/or hPMS1, are likely to be involved in DNA mismatch repair. By analogy to hMLH1 and hMSH2, mutations in the genes which encode for such proteins would be strong candidates for potential cancer linkage. A powerful molecular genetic approach using yeast, referred to as a "two-hybrid system", allows the relatively rapid detection and isolation of genes encoding proteins that interact with a gene product of interest, e.g., hMLH1.[28]

The two-hybrid system involves two plasmid vectors each intended to encode a fusion protein. Each of the two vectors contains a portion, or domain, of a transcription activator. The yeast cell used in the detection scheme contains a "reporter" gene. The activator alone cannot activate transcription. However, if the two domains are brought into close proximity then transcription may occur. The cDNA for the protein of interest, e.g., hMLH1 is inserted within a reading frame in one of the vectors. This is termed the "bait". A library of human cDNAs, inserted into a second plasmid vector so as to make fusions with the other domain of the transcriptional activator, is introduced into the yeast cells harboring the "bait" vector. If a particular yeast cell receives a library member that contains a human cDNA encoding a protein that interacts with hMLH1 protein, this interaction will bring the two domains of the transcriptional activator into close proximity, activate transcription of the reporter gene and the yeast cell will turn blue. Next, the insert is sequenced to determine whether it is related to any sequence in the data base. The same procedure can be used to identify yeast proteins in DNA mismatch repair or a related process. Performing the yeast and human "hunts" in parallel has certain advantages. The function of novel yeast homologs can be quickly determined in yeast by gene disruption and subsequent examination of the genetic consequences of being defective in the new found gene. These yeast studies will help guide the analysis of novel human "hMLH1-or hPMS1-interacting" proteins in much the same way that the yeast studies on PMS1 and MLH1 have influenced our studies of the human MLH1 and PMS1 genes.

Production of Antibodies

By using our knowledge of the DNA sequences for hMLH1 and hPMS1, we can synthesize all or portions of the predicted protein structures for the purpose of producing antibodies. One important use for antibodies directed to hMLH1 and hPMS1 proteins will be for capturing other proteins which may be involved in DNA mismatch repair. For example, by employing coimmuno-precipitation techniques, antibodies directed to either hMLH1 or hPMS1 may be precipitated along with other associated proteins which are functionally and/or physically related. Another important use for antibodies will be for the purpose of isolating hMLH1 and hPMS1 proteins from tumor tissue. The hMLH1 and hPMS1 proteins from tumors can then be characterized for the purpose of determining appropriate treatment strategies.

We are in the process of developing monoclonal antibodies directed to the hMLH1 and hPMS1 proteins.

EXAMPLE 5

We have also used the following procedure to produce polyclonal antibodies directed to the human and mouse forms of PMS1 protein.

We inserted a 3' fragment of the mouse PMS1 cDNA in the bacterial expression plasmid vector, pET (Novagen, Madison, Wis.). The expected expressed portion of the mouse PMS1 protein corresponds to a region of approximately 200 amino acids at the end of the PMS1 protein. This portion of the mPMS1 is conserved with yeast PMS1 but is not conserved with either the human or the mouse MLH1 proteins. One reason that we selected this portion of the PMS1 protein for producing antibodies is that we did not want the resulting antibodies to cross-react with MLH1. The mouse PMS1 protein fragment was highly expressed in $E.$ $coli.$, purified from a polyacrylamide gel and the eluted protein was then prepared for animal injections. Approximately 2 mg of the PMS1 protein fragment was sent to the Pocono Rabbit Farm (PA) for injections into rabbits. Sera from rabbits multiple times was tittered against the PMS1 antigen using standard ELISA techniques. Rabbit antibodies specific to mouse PMS1 protein were affinity-purified using columns containing immobilized mouse PMS1 protein. The affinity-purified polyclonal antibody preparation was tested further using Western blotting and dot blotting. We found that the polyclonal antibodies recognized, not only the mouse PMS1 protein, but also the human PMS1 protein which is very similar. Based upon the Western blots, there is no indication that other proteins were recognized strongly by our antibody, including either the human or mouse MLH1 proteins.

DNA Mismatch Repair Defective Mice

EXAMPLE 6

In order to create a experimental model system for studying DNA mismatch repair defects and resultant cancer in a whole animal system we have derived DNA mismatch repair defective mice using embryonic stem (ES) cell technology. Using genomic DNA containing a portion of the mPMS1 gene we constructed a vector that upon homologous recombination causes disruption of the chromosomal mPMS1 gene. Mouse ES cells from the 129 mouse strain were confirmed to contain a disrupted mPMS1 allele. The ES cells were injected into C57/BL6 host blastocysts to produce animals that were chimeric or a mixture of 129 and C57/BL6 cells. The incorporation of the ES cells was determined by the presence of patches of agouti coat coloring (indicative of ES cell contribution). All male chimeras were bred with C57/BL6 female mice.

Subsequently, twelve offspring ($F_2$) were born in which the agouti coat color was detected indicating the germline transmission of genetic material from the ES cells. Analysis of DNA extracted from the tail tips of the twelve offspring indicated that six of the animals were heterozygous (contained one wild-type and one mutant allele) for the mPMS1 mutation. Of the six heterozygous animals, three were female, (animals $F_2$-8, $F_2$-11 and $F_2$-12) and three were males ($F_2$, $F_2$-10 and $F_2$-13). Four breeding pens were set up to obtain mice that were homozygous for mPMS1 mutation, and additional heterozygous mice. Breeding pen #1 which contained animals $F_2$-11 and $F_2$-10, yielded a total of thirteen mice in three litters, four of which have been genotyped. Breeding pen #2 (animals $F_2$-8 and $F_2$-13) gave twenty-two animals and three litters, three of which have been genotyped. Of the seven animals genotyped, three homozygous female animals have been identified. One animal died at six weeks of age from unknown causes. The remaining homozygous females are alive and healthy at twelve weeks of age. The results indicate that mPMS1 homozygous defective mice are viable.

Breeding pens #3 and #4 were used to backcross the mPMS1 mutation into the C57/BL6 background. Breeding pen #3 (animal $F_2$-12 crossed to a C57/BL6 mouse) produced twenty-one animals in two litters, nine of which have been genotyped. Breeding pen #4 (animal $F_2$-6 crossed with a C57/BL6 mouse) gave eight mice. In addition, the original male chimera (breeding pen #5) has produced thirty-one additional offspring.

To genotype the animals, a series of PCR primers have been developed that are used to identify mutant and wild-type mPMS1 genes. They are: (SEQ ID NOS: 143–148, respectively)

Primer 1: 5'TTCGGTGACAGATTTGTAAATG-3'
Primer 2: 5'TTTACGGAGCCCTGGC-3'
Primer 3: 5'TCACCATAAAAATAGTTTCCCG-3'
Primer 4: 5'TCCTGGATCATATTTTCTGAGC-3'
Primer 5: 5'TTTCAGGTATGTCCTGTTACCC-3'
Primer 6: 5'TGAGGCAGCTTTTAAGAAACTC-3'
Primers 1+2 (5'targeted)
Primers 1+3 (5'untargeted)
Primers 4+5 (3'targeted)
Primers 4+6 (3'untargeted)

The mice we have developed provide an animal model system for studying the consequences of defects in DNA mismatch repair and resultant HNPCC. The long term survival of mice homozygous and heterozygous for the mPMS1 mutation and the types and timing of tumors in these mice will be determined. The mice will be screened daily for any indication of cancer onset as indicated by a hunched appearance in combination with deterioration in coat condition. These mice carrying mPMS1 mutation will be used to test the effects of other factors, environmental and genetic, on tumor formation. For example, the effect of diet on colon and other type of tumors can be compared for normal mice versus those carrying mPMS1 mutation either in the heterozygous or homozygous genotype. In addition, the mPMS1 mutation can be put into different genetic backgrounds to learn about interactions between genes of the mismatch repair pathway and other genes involved in human cancer, for example, p53. Mice carrying mPMS1 mutations will also be useful for testing the efficacy of somatic gene therapy on the cancers that arise in mice, for example, the expected colon cancers. Further, isogenic fibroblast cell lines from the homozygous and heterozygous mPMS1 mice can be established for use in various cellular studies, including the determination of spontaneous mutation rates.

We are currently constructing a vector for disrupting the mouse mMLH1 gene to derive mice carrying mutation in hMLH1. We will compare mice carrying defects in mPMS1 to mice carrying defects in mMLH1. In addition, we will construct mice that carry mutations in both genes to see whether there is a synergistic effect of having mutations in two HNPCC genes. Other studies on the mMLH1 mutant mice will be as described above for the mPMS1 mutant mice.

We claim:

1. A composition comprising purified antibodies that bind specifically to the hMLH1 protein as shown in SEQ ID NO:5.

2. The composition of claim 1 wherein the antibodies are polyclonal.

3. The composition of claim 1 wherein the antibodies are monoclonal.

4. The composition of claim 1, wherein the antibodies are fluorescently labeled.

5. The composition of claim 1 further comprising a human tissue sample in contact with the antibodies.

6. The composition of claim 5, wherein the tissue sample comprises a cross-section of a tumor specimen.

* * * * *